US008404635B2

(12) United States Patent
Fogelman et al.

(10) Patent No.: US 8,404,635 B2
(45) Date of Patent: *Mar. 26, 2013

(54) ORALLY ADMINISTERED PEPTIDES SYNERGIZE STATIN ACTIVITY

(75) Inventors: Alan M. Fogelman, Beverly Hills, CA (US); Gattadahalli M. Anantharamaiah, Birmingham, AL (US); Mohamad Navab, Los Angeles, CA (US)

(73) Assignees: The Regents of the University of California, Oakland, CA (US); The UAB Research Foundation, Birmingham, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/180,309

(22) Filed: Jul. 11, 2011

(65) Prior Publication Data
US 2012/0035095 A1    Feb. 9, 2012

Related U.S. Application Data

(63) Continuation of application No. 11/830,687, filed on Jul. 30, 2007, now Pat. No. 7,994,132, which is a continuation of application No. 11/431,412, filed on May 9, 2006, now Pat. No. 7,531,514, which is a continuation of application No. 10/423,830, filed on Apr. 25, 2003, now Pat. No. 7,199,102, which is a continuation-in-part of application No. 10/273,386, filed on Oct. 16, 2002, now Pat. No. 7,166,578, which is a continuation-in-part of application No. 10/187,215, filed on Jun. 28, 2002, now Pat. No. 7,144,862, which is a continuation-in-part of application No. 09/896,841, filed on Jun. 29, 2001, now Pat. No. 6,933,279, which is a continuation-in-part of application No. 09/645,454, filed on Aug. 24, 2000, now Pat. No. 6,664,230.

(51) Int. Cl.
*A61K 38/10* (2006.01)
(52) U.S. Cl. .......................... 514/1.9; 514/21.4
(58) Field of Classification Search ........................ None
See application file for complete search history.

(56) References Cited

U.S. PATENT DOCUMENTS

| | | | |
|---|---|---|---|
| 3,767,040 A | 10/1973 | Tushaus |
| 4,155,913 A | 5/1979 | Hellerbach et al. |
| 4,428,938 A | 1/1984 | Kisfaludy et al. |
| 4,643,988 A | 2/1987 | Segrest et al. |
| 4,684,520 A | 8/1987 | Bertelli |
| 5,298,490 A | 3/1994 | Heavner et al. |
| 5,344,822 A | 9/1994 | Levine et al. |
| 5,358,934 A | 10/1994 | Borovsky et al. |
| 5,480,869 A | 1/1996 | Wei et al. |
| 5,595,973 A | 1/1997 | Bogden |
| 5,721,138 A | 2/1998 | Lawn |
| 5,733,549 A | 3/1998 | Yamada et al. |
| 5,733,879 A | 3/1998 | Rosseneu et al. |
| 5,814,467 A | 9/1998 | Curtiss et al. |
| 5,854,238 A | 12/1998 | Kempen |
| 6,004,925 A | 12/1999 | Dasseux et al. |
| 6,011,002 A | 1/2000 | Pastan et al. |
| 6,019,739 A | 2/2000 | Rhee et al. |
| 6,037,323 A | 3/2000 | Dasseux et al. |
| 6,040,147 A | 3/2000 | Ridker et al. |
| 6,046,166 A | 4/2000 | Dasseux et al. |
| 6,086,918 A | 7/2000 | Stern et al. |
| 6,191,151 B1 | 2/2001 | Zik |
| 6,228,989 B1 | 5/2001 | Traugh et al. |
| 6,265,377 B1 | 7/2001 | Dasseux et al. |
| 6,273,913 B1 | 8/2001 | Wright et al. |
| 6,287,590 B1 | 9/2001 | Dasseux et al. |
| 6,303,619 B1 | 10/2001 | Linden |
| 6,329,341 B1 | 12/2001 | Dasseux et al. |
| 6,376,464 B1 | 4/2002 | Dasseux et al. |
| 6,383,808 B1 | 5/2002 | Monia et al. |
| 6,444,230 B1 | 9/2002 | Godin et al. |
| 6,444,681 B1 | 9/2002 | Flavahan et al. |
| 6,455,088 B1 | 9/2002 | Dasseux et al. |
| 6,464,975 B2 | 10/2002 | Millis |
| 6,498,038 B1 | 12/2002 | Ghosh et al. |
| 6,518,412 B1 | 2/2003 | Dasseux et al. |
| 6,555,651 B2 | 4/2003 | Stern et al. |
| 6,573,239 B1 | 6/2003 | Dasseux et al. |
| 6,602,854 B1 | 8/2003 | Dasseux et al. |
| 6,630,450 B1 | 10/2003 | Dasseux et al. |
| 6,635,623 B1 | 10/2003 | Hoogeveen et al. |
| 6,664,230 B1 | 12/2003 | Fogelman et al. |
| 6,696,545 B1 | 2/2004 | Buelow et al. |
| 6,716,816 B1 | 4/2004 | Dasseux et al. |
| 6,717,031 B2 | 4/2004 | Games et al. |
| 6,727,063 B1 | 4/2004 | Lander et al. |
| 6,734,169 B2 | 5/2004 | Dasseux et al. |
| 6,753,313 B1 | 6/2004 | Dasseux et al. |
| 6,846,636 B1 | 1/2005 | Argraves et al. |
| 6,849,714 B1 | 2/2005 | Bridon et al. |

(Continued)

FOREIGN PATENT DOCUMENTS

| AU | 2001-286732 | 3/2002 |
|---|---|---|
| AU | 2005-287004 | 3/2006 |

(Continued)

OTHER PUBLICATIONS

U.S. Appl. No. 10/269,755, filed Oct. 11, 2002, Fogelman et al.

(Continued)

*Primary Examiner* — Jeffrey E Russel
(74) *Attorney, Agent, or Firm* — Tom Hunter; Weaver Austin Villeneuve & Sampson LLP

(57) ABSTRACT

This invention provides novel peptides that ameliorate one or more symptoms of atherosclerosis. The peptides are highly stable and readily administered via an oral route. The peptides are effective to stimulate the formation and cycling of prebeta high density lipoprotein-like particles and/or to promote lipid transport and detoxification. This invention also provides a method of tracking a peptide in a mammal. In addition, the peptides inhibit osteoporosis. When administered with a statin, the peptides enhance the activity of the statin permitting the statin to be used at significantly lower dosages and/or cause the statins to be significantly more anti-inflammatory at any given dose.

14 Claims, 10 Drawing Sheets

U.S. PATENT DOCUMENTS

| | | | |
|---|---|---|---|
| 6,869,568 | B2 | 3/2005 | Fogelman et al. |
| 6,887,470 | B1 | 5/2005 | Bridon et al. |
| 6,933,279 | B2 | 8/2005 | Fogelman et al. |
| 6,936,691 | B2 | 8/2005 | Fiscella et al. |
| 6,982,348 | B2 | 1/2006 | Kori et al. |
| 7,144,862 | B2 | 12/2006 | Fogelman et al. |
| 7,148,197 | B2 | 12/2006 | Fogelman et al. |
| 7,166,578 | B2 | 1/2007 | Fogelman et al. |
| 7,199,102 | B2 | 4/2007 | Fogelman et al. |
| 7,291,590 | B2 | 11/2007 | Kisilevsky et al. |
| 7,470,660 | B2 | 12/2008 | Schwartz et al. |
| 7,531,514 | B2 | 5/2009 | Fogelman et al. |
| 7,579,319 | B2 | 8/2009 | Fogelman |
| 7,723,303 | B2 | 5/2010 | Fogelman et al. |
| 7,807,640 | B2 | 10/2010 | Fogelman et al. |
| 7,820,784 | B2 | 10/2010 | Fogelman et al. |
| 7,994,132 | B2 | 8/2011 | Fogelman et al. |
| 8,048,851 | B2 | 11/2011 | Fogelman et al. |
| 8,236,754 | B2 | 8/2012 | Fogelman |
| 2001/0005714 | A1 | 6/2001 | Boffelli et al. |
| 2002/0042441 | A1 | 4/2002 | Acton et al. |
| 2002/0142369 | A1 | 10/2002 | Fersht |
| 2003/0027769 | A1 | 2/2003 | Scialdone et al. |
| 2003/0040505 | A1 | 2/2003 | Fogelman et al. |
| 2003/0045460 | A1 | 3/2003 | Fogelman et al. |
| 2003/0077641 | A1 | 4/2003 | Laskowitz et al. |
| 2003/0083698 | A1 | 5/2003 | Whitehurst et al. |
| 2003/0087819 | A1 | 5/2003 | Bielicki |
| 2003/0125260 | A1 | 7/2003 | Haviv et al. |
| 2003/0171277 | A1 | 9/2003 | Fogelman et al. |
| 2003/0191057 | A1 | 10/2003 | Fogelman et al. |
| 2003/0203842 | A1 | 10/2003 | Dasseux et al. |
| 2003/0229015 | A1 | 12/2003 | Fogelman et al. |
| 2004/0059110 | A1 | 3/2004 | Nakano et al. |
| 2004/0136989 | A1 | 7/2004 | Banerjee et al. |
| 2004/0152623 | A1 | 8/2004 | Varadhachary et al. |
| 2004/0254120 | A1 | 12/2004 | Fogelman et al. |
| 2004/0266663 | A1 | 12/2004 | Schwartz et al. |
| 2004/0266671 | A1 | 12/2004 | Fogelman et al. |
| 2005/0070996 | A1 | 3/2005 | Dinh et al. |
| 2005/0154046 | A1 | 7/2005 | Wang et al. |
| 2005/0197381 | A1 | 9/2005 | Wang et al. |
| 2005/0229015 | A1 | 10/2005 | Van Rens et al. |
| 2005/0239136 | A1 | 10/2005 | Hazen et al. |
| 2005/0272634 | A1 | 12/2005 | Bahlmann et al. |
| 2006/0069030 | A1 | 3/2006 | Bachovchin |
| 2006/0205634 | A1 | 9/2006 | Varadhachary et al. |
| 2006/0205669 | A1 | 9/2006 | Fogelman et al. |
| 2006/0217298 | A1 | 9/2006 | Srivastava |
| 2006/0217307 | A1 | 9/2006 | Takashi et al. |
| 2006/0234908 | A1 | 10/2006 | Fogelman et al. |
| 2007/0032430 | A1 | 2/2007 | Fogelman et al. |
| 2007/0254839 | A1 | 11/2007 | Fogelman et al. |
| 2008/0045459 | A1 | 2/2008 | Fogelman et al. |
| 2008/0095821 | A1 | 4/2008 | Fogelman et al. |
| 2008/0096814 | A1 | 4/2008 | Fogelman et al. |
| 2008/0096815 | A1 | 4/2008 | Fogelman et al. |
| 2008/0096816 | A1 | 4/2008 | Fogelman et al. |
| 2008/0293639 | A1 | 11/2008 | Fogelman et al. |
| 2009/0028925 | A1 | 1/2009 | Erion et al. |
| 2009/0081298 | A1 | 3/2009 | Murase et al. |
| 2009/0286741 | A1 | 11/2009 | Fogelman et al. |
| 2010/0227825 | A1 | 9/2010 | Fogelman et al. |
| 2012/0004720 | A1 | 1/2012 | Fogelman et al. |

FOREIGN PATENT DOCUMENTS

| | | |
|---|---|---|
| CA | 2420222 | 2/2002 |
| CA | 2580501 | 3/2006 |
| CN | 1469754 | 10/2005 |
| CN | 1739787 A | 3/2006 |
| CN | 1943781 | 4/2007 |
| EA | 6488 | 12/2005 |
| EP | 1186299 | 3/2002 |
| EP | 1318828 | 6/2003 |
| EP | 1562624 | 8/2005 |
| EP | 1799242 | 6/2007 |
| JP | 61-126099 | 6/1986 |
| JP | 3-503178 | 7/1991 |
| JP | 7-507554 | 8/1995 |
| JP | 09-505559 | 6/1997 |
| JP | 11-500311 | 1/1999 |
| JP | 11-507376 | 6/1999 |
| JP | 2000-136202 | 5/2000 |
| JP | 2000-509020 | 7/2000 |
| JP | 2004-506693 | 3/2004 |
| JP | 03822167 | 9/2006 |
| JP | 2006-312650 | 11/2006 |
| JP | 2007-277250 | 10/2007 |
| MX | PA2010763 | 3/2003 |
| WO | WO 91/05043 | 4/1991 |
| WO | WO 95/07707 | 3/1995 |
| WO | WO 96/25434 | 8/1996 |
| WO | WO 96/40770 | 12/1996 |
| WO | WO 96/41815 | 12/1996 |
| WO | WO 97/36927 | 10/1997 |
| WO | WO 98/09602 | 3/1998 |
| WO | WO 99/16408 | 4/1999 |
| WO | WO 99/16409 | 4/1999 |
| WO | WO 99/16409 | 4/1999 |
| WO | WO 99/47566 | 9/1999 |
| WO | WO 00/06599 | 2/2000 |
| WO | WO 00/34469 | 6/2000 |
| WO | WO 01/75168 | 10/2001 |
| WO | WO 01/75170 | 10/2001 |
| WO | WO 01/81376 | 11/2001 |
| WO | WO 02/15923 | 2/2002 |
| WO | WO 02/22161 | 3/2002 |
| WO | WO 02/098446 | 12/2002 |
| WO | WO 03/017924 | 3/2003 |
| WO | WO 03/038886 | 5/2003 |
| WO | WO 03/086326 | 10/2003 |
| WO | WO 2004/034977 A2 | 4/2004 |
| WO | WO 2004/043396 | 5/2004 |
| WO | WO 2005/000887 | 1/2005 |
| WO | WO 2005/016280 | 2/2005 |
| WO | WO 2005/116643 | 12/2005 |
| WO | WO 2006/020652 | 2/2006 |
| WO | WO 2006/034056 | 3/2006 |
| WO | WO 2006/063132 | 6/2006 |
| WO | WO 2006/118805 | 11/2006 |
| WO | WO 2009/073725 | 6/2009 |

OTHER PUBLICATIONS

U.S. Appl. No. 11/229,042, filed Sep. 16, 2005, Fogelman et al.
U.S. Appl. No. 11/541,481, filed Sep. 26, 2006, Fogelman et al.
U.S. Appl. No. 11/541,482, filed Sep. 26, 2006, Fogelman et al.
U.S. Appl. No. 11/541,494, filed Sep. 26, 2006, Fogelman et al.
U.S. Appl. No. 13/156,269, filed Jun. 8, 2011, Fogelman et al.
International Search Report dated Jan. 3, 2002 issued in WO 2002/015923.
International Written Opinion dated May 20, 2002 issued in WO 2002/015923.
International Preliminary Examination Report dated Sep. 20, 2002 issued in PCT/US01/26497 (WO 2002/015923).
Australian Examiner's First Report dated Jun. 6, 2005 issued in AU 2001286732.
Australian Notice of Acceptance and Allowed Claims dated Sep. 21, 2005 issued in AU 2001286732.
Australian Examiner's Report No. 2 dated Jan. 17, 2007 issued in AU 2006 2000035.
Australian Examiner's First Report dated Feb. 13, 2008 issued in AU 2007237157.
Australian Examiner's First Report dated Mar. 18, 2011 issued in AU 2009202705.
Canadian Office Action dated Feb. 25, 2005 issued in CA2420222.
Canadian Office Action dated Mar. 1, 2006 issued in CA2420222.
Canadian Office Action dated Sep. 19, 2006 issued in CA2420222.
Canadian Office Action dated Jun. 1, 2007 issued in CA2420222.
Canadian Office Action dated Apr. 1, 2008 issued in CA2420222.
Canadian Office Action dated Feb. 12, 2009 issued in CA 2,639,651.
Canadian Office Action dated Feb. 23, 2011 issued in CA 2,718,348.
Chinese First Office Action dated Jul. 9, 2004 issued in CN 01817280.6.

Chinese First Office Action dated Apr. 19, 2007 issued in CN 200510103876.X.
Chinese Second Office Action dated Jun. 19, 2009 issued in CN 200510103876.X.
Chinese First Office Action dated Jun. 2, 2008 issued in CN200610100668.9.
Chinese Second Office Action dated Aug. 28, 2009 issued in CN200610100668.9.
Chinese Third Office Action dated Apr. 9, 2010 issued in CN200610100668.9.
Chinese First Office Action dated Feb. 15, 2008 issued in CN200610100670.6.
Chinese Second Office Action dated Apr. 15, 2010 issued in CN200610100670.6.
Chinese First Office Action dated Nov. 23, 2007 issued in CN 200610100669.3.
Chinese Second Office Action dated Apr. 30, 2010 issued in CN 200610100669.3.
Chinese Office Action (Final Rejection) dated Feb. 24, 2011 issued in CN 200610100669.3.
Chinese First Office Action dated Feb. 2, 2008 issued in CN 200610100667.4.
Chinese Second Office Action dated Nov. 17, 2008 issued in CN 200610100667.4.
Eurasian Office Action dated Mar. 30, 2003 issued in EA 2003 00289/28.
Eurasian Office Action dated Apr. 6, 2007 issued in EA 2005 01744/28.
European Supplementary Partial Search Report dated Sep. 9, 2004 issued in EP0 1966198.2 (EP 1318828).
European Office Action dated Mar. 7, 2005 issued in EP 01966198.2 (EP 1318828).
European Office Action dated Jan. 9, 2007 issued in EP 01966198.2 (EP1318828).
European Office Action dated Nov. 2, 2007 issued in EP 01966198.2 (EP 1318828).
European Search Report dated Nov. 7, 2007 issued in EP 07 007 775.5 (EP1864675).
European Examination Report dated Apr. 29, 2008 issued in EP 07 007 775.5 (EP1864675).
European Office Action dated Jul. 15, 2009 issued in EP 07 007 775.5 (EP1864675).
European Partial Search Report dated May 7, 2010 issued in EP 10 00 2402.5-2401/2198877.
European Extended Search Report dated Nov. 2, 2010 issued in EP 10 00 2402.5-2401/2198877.
European Reminder Concerning Payment of Designation Fee and Examination Fee dated Dec. 6, 2010 issued in EP 10 00 2402.5-2401/2198877.
Israeli Office Action dated Nov. 20, 2007 issued in IL-154545.
Israeli Office Action dated Aug. 7, 2008 issued in IL-154545.
Israeli Office Action dated Nov. 10, 2009 issued in IL-154545.
Israeli Office Action dated Nov. 2, 2010 issued in IL-154545.
Israeli Office Action dated Feb. 13, 2011 issued in IL-206114.
Japanese Office Action dated Jul. 19, 2005 issued in JP2002-520844.
Japanese Office Action dated Nov. 15, 2005 issued in JP2002-520844.
Japanese Office Action dated Feb. 14, 2006 issued in JP 2005-304531.
Japanese Office Action dated May 14, 2008 issued in JP2005-304531.
Japanese Office Action dated Oct. 31, 2006 issued in JP2006-220831.
Japanese Office Action dated May 29, 2007 issued in JP2006-220831.
Japanese Office Action dated Jan. 8, 2009 issued in JP2006-220831.
Japanese Office Action dated Jul. 7, 2010 issued in JP2007-250264.
Japanese Final Office Action dated Oct. 21, 2011 issued in JP2007-250264.
Japanese First Office Action dated May 10, 2010 issued in JP2007-118451.
Japanese Notice of Final Rejection dated Jul. 29, 2011 issued in JP2007-118451.
International Search Report and Written Opinion dated Sep. 8, 2004 issued in WO 2004/034977.
Australian Examination Report dated Sep. 11, 2008 issued in AU 2003284129.
Canadian First Office Action dated May 28, 2010 issued in CA 2,501,943.
Canadian Second Office Action dated Jun. 8, 2011 issued in CA 2,501,943.
Chinese First Office Action dated Sep. 6, 2007 issued in CN 200380106367.1.
Chinese Second Office Action dated Jan. 16, 2009 issued in CN 200380106367.1.
Chinese First Office Action dated Jan. 25, 2011 issued in CN 201010156423.4.
Chinese Second Office Action dated Aug. 16, 2011 issued in CN 201010156423.4.
European Supplementary Search Report dated Jun. 29, 2009 issued in EP 03 77 6360.4-2403 / 1562624.
European Examination Report dated Oct. 7, 2009 issued in EP 03 776 360.4-2403.
European Examination Report dated Oct. 14, 2011 issued in EP 03 776 360.4-2403.
Indian Office Action dated Jun. 3, 2007 issued in in 613/CHENP/2005.
Japanese Office Action dated Jul. 28, 2009 issued in JP 2005-501402.
International Search Report, International Preliminary Report on Patentability and Written Opinion dated Apr. 19, 2006 issued in WO 2006/034056.
Australian Examiner's First Report dated Nov. 10, 2010 issued in AU 2005287004.
Australian Examiner's Second Report dated Feb. 8, 2011 issued in AU 2005287004.
Chinese First Office Action dated Sep. 25, 2009 issued in CN 200580039224.2.
Chinese Second Office Action dated Dec. 1, 2010 issued in CN 200580039224.2.
European Extended Search Report; Supplemental EP Search Report and EP Search Opinion dated Sep. 14, 2009 issued in EP 05803724.3-2405.
European Communication and Search Opinion dated Jan. 20, 2010 issued in EP 05803724.3-2405.
Japanese Office Action (Notices of Reasons for Rejection) dated Jun. 14, 2011 issued in JP 2007-532511.
Russian First Office Action dated Dec. 7, 2010 issued in RU 2007114144 (015354).
Russian Second Office Action dated Feb. 24, 2011 issued in RU 2007114144 (015354).
International Search Report, International Preliminary Report on Patentability and Written Opinion dated Jun. 21, 2006 issued in WO 2006/063132.
Australian Examiner's First Report dated Feb. 15, 2011 issued in AU 2005314043.
Chinese First Office Action dated Jan. 8, 2010 issued in CN 200580047756.0.
Chinese Second Office Action dated Mar. 2, 2011 issued in CN 200580047756.0.
Indonesian Office Action dated Oct. 26, 2010 issued in Indonesian Patent Application No. W-00200701762.
Israeli Office Action (description) dated Oct. 26, 2009 issued in IL 183689.
Indian First Examination Report dated Mar. 24, 2011 issued in IN Appln No. 2439/KOLN/2007.
Japanese Office Action dated Jul. 28, 2011 issued in JP 2007-544634.
Malaysian Examination and Search Report dated Jun. 30, 2010 issued in PI 20070907.
New Zealand Examination Report dated May 23, 2008 issued in NZ 555826.
New Zealand Examination Report dated Jul. 3, 2009 issued in NZ 555826.
New Zealand Examination Report dated Nov. 2, 2009 issued in NZ 580650.
Russian First Office Action dated Apr. 26, 2010 issued in RU 2007125589/15 (027875).

Singapore Search Report and Written Opinion dated Sep. 22, 2008 issued in SG 200703988-6.
Singapore Second Written Opinion dated May 12, 2009 issued in SG 200703988-6.
Trinidad & Tobago Office Action dated Apr. 27, 2011 issued in TT/A/2007/00132.
Vietnamese Office Action date Oct. 2, 2007 issued in VN 1-2007-01344.
Vietnamese Office Action dated Feb. 21, 2008 issued in VN 1-2007-01344.
International Search Report dated Apr. 18, 2007 issued in WO 2006/118805.
International Preliminary Report on Patentability and Written Opinion dated Apr. 18, 2007 issued in WO 2006/118805.
Australian Examiner's first report dated Sep. 26, 2011 issued in AU 2006242651.
Chinese First Office Action dated May 20, 2010 issued in CN200680023011.5.
Eurasian Search Report dated May 26, 2010 issued in EA 200900786.
European Extended Search Report; Supplementary European Search Report and the European Search Opinion dated Sep. 30, 2009 issued in EP 06 750 791.3-2403.
European Examination Report dated Jun. 7, 2010 issued in EP 06 750 791.3-2403.
European Result of Consultation dated Aug. 6, 2010 issued in EP 06 750 791.3-2403.
European Examination Report dated Dec. 17, 2010 issued in EP 06 750 791.3-2403.
European Examination Report dated Oct. 14, 2011 issued in EP 06 750 791.3-2403.
European Extended Search Report and Written Opinion dated Nov. 24, 2010 issued in EP 10 177 858.7-2403.
European Examination Report dated Aug. 25, 2011 issued in EP 10 177 858.7-2403.
European Extended Search Report dated Aug. 23, 2011 issued in EP 11 15 5927.4-2403.
Israeli Office Action (description) dated Mar. 2, 2009 issued in IL 186959.
Israeli First Substantive Examination Report (translation) dated Mar. 15, 2010 issued in IL 186959 (138784).
Mexican Office Action dated Jan. 19, 2008 issued in MX/a/2007/013430.
Mexican Office Action dated Oct. 10, 2011 issued in MX/a/2007/013430.
New Zealand Examination Report dated Jan. 20, 2009 issued in NZ 563187.
New Zealand Examination Report dated Nov. 20, 2009 issued in NZ 563187.
New Zealand Examination Report dated Nov. 10, 2009 issued in NZ 580954.
New Zealand Examination Report dated Feb. 18, 2011 issued in NZ 580954.
Philippines Office Action dated Jan. 25, 2011 issued in PH 1-2007-502394.
Singapore Search Report and Written Opinion dated Mar. 12, 2009 issued in SG 2007171077.
Singapore Second Written Opinion dated Oct. 29, 2009 issued in SG 200717107-7.
Singapore Examination Report dated Sep. 1, 2010 issued in SG 200717107-7.
Vietnamese Examination as to Form dated Feb. 28, 2008 issued in Appln No. 1-2007-02543.
Vietnamese First Office Action dated May 26, 2010 issued in Appln No. 1-2007-02543.
Declaration of Non-Establishment of International Search Report and Written Opinion dated Apr. 24, 2009 issued in WO 2009/073725 (PCT/US2008/085409).
US Office Action dated Apr. 23, 2008 issued in U.S. Appl. No. 11/431,412.
US Notice of Allowance dated Dec. 11, 2008 issued in U.S. Appl. No. 11/431,412.
US Office Action dated Nov. 26, 2008 issued in U.S. Appl. No. 11/689,037.
US Office Action Final dated Jun. 23, 2009 issued in U.S. Appl. No. 11/689,037.
US Office Action (and Interview Summary) dated Sep. 28, 2009 issued in U.S. Appl. No. 11/689,037.
US Office Action (Examiner Interview Summary) dated Nov. 17, 2009 issued in U.S. Appl. No. 11/689,037.
US Office Action (Advisory Action Before the Filing of an Appeal Brief) dated Dec. 9, 2009 issued in U.S. Appl. No. 11/689,037.
US Notice of Allowance dated Apr. 8, 2010 issued in U.S. Appl. No. 11/689,037.
US Office Action dated May 1, 2009 issued in U.S. Appl. No. 11/830,664.
US Office Action Final dated Nov. 10, 2009 issued in U.S. Appl. No. 11/830,664.
US Office Action (Notice of Abandonment) dated Jun. 18, 2010 issued in U.S. Appl. No. 11/830,664.
US Office Action (Examiner's Interview Summary) dated Apr. 27, 2009 issued in U.S. Appl. No. 11/830,675.
US Office Action dated Jun. 5, 2009 issued in U.S. Appl. No. 11/830,675.
US Office Action Final dated Dec. 18, 2009 issued in U.S. Appl. No. 11/830,675.
US Notice of Allowance dated Jun. 18, 2010 issued in U.S. Appl. No. 11/830,675.
US Office Action dated Sep. 9, 2009 issued in U.S. Appl. No. 11/830,687.
US Office Action Final dated Feb. 26, 2010 issued in U.S. Appl. No. 11/830,687.
US Office Action dated Jul. 1, 2010 issued in U.S. Appl. No. 11/830,687.
US Office Action Final dated Jan. 11, 2011 issued in U.S. Appl. No. 11/830,687.
US Notice of Allowance dated Mar. 29, 2011 issued in U.S. Appl. No. 11/830,687.
US Office Action dated Sep. 12, 2002 issued in U.S. Appl. No. 09/645,454.
US Office Action dated Jan. 23, 2003 issued in U.S. Appl. No. 09/645,454.
US Notice of Allowance dated Jun. 25, 2003 issued in U.S. Appl. No. 09/645,454.
US Office Action dated Oct. 21, 2003 issued in U.S. Appl. No. 09/896,841.
US Final Office Action dated May 7, 2004 issued in U.S. Appl. No. 09/896,841.
US Notice of Allowance dated Dec. 20, 2004 issued in U.S. Appl. No. 09/896,841.
US Office Action dated Jan. 8, 2004 issued in U.S. Appl. No. 10/187,215.
US Office Action dated Aug. 26, 2004 issued in U.S. Appl. No. 10/187,215.
US Final Office Action dated Apr. 11, 2005 issued in U.S. Appl. No. 10/187,215.
US Office Action dated Oct. 28, 2005 issued in U.S. Appl. No. 10/187,215.
US Notice of Allowance dated May 1, 2006 issued in U.S. Appl. No. 10/187,215.
US Office Action dated Jun. 21, 2004 issued in U.S. Appl. No. 10/273,386.
US Final Office Action dated Feb. 2, 2005 issued in U.S. Appl. No. 10/273,386.
US Office Action dated Sep. 7, 2005 issued in U.S. Appl. No. 10/273,386.
US Final Office Action dated Mar. 31, 2006 issued in U.S. Appl. No. 10/273,386.
US Notice of Allowance dated Aug. 2, 2006 issued in U.S. Appl. No. 10/273,386.
US Office Action dated Apr. 18, 2005 issued in U.S. Appl. No. 10/423,830.
US Final Office Action dated Nov. 15, 2005 issued in U.S. Appl. No. 10/423,830.

US Notice of Allowance dated Nov. 21, 2006 issued in U.S. Appl. No. 10/423,830.
US Office Action dated Aug. 17, 2007 issued in U.S. Appl. No. 11/229,042.
US Final Office Action dated Apr. 30, 2008 issued in U.S. Appl. No. 11/229,042.
US Office Action dated Jan. 26, 2009 issued in U.S. Appl. No. 11/229,042.
US Office Action Final dated Oct. 5, 2009 issued in U.S. Appl. No. 11/229,042.
US Office Action dated Mar. 23, 2011 issued in U.S. Appl. No. 11/229,042.
US Office Action dated Apr. 4, 2007 issued in U.S. Appl. No. 11/296,582.
US Final Office Action dated Feb. 5, 2008 issued in U.S. Appl. No. 11/296,582.
US Notice of Allowance dated Mar. 9, 2009 issued in U.S. Appl. No. 11/296,582.
US Office Action dated Jan. 13, 2011 issued in U.S. Appl. No. 12/478,593.
US Office Action dated Aug. 10, 2011 issued in U.S. Appl. No. 12/478,593.
US Office Action dated Jan. 17, 2008 issued in U.S. Appl. No. 11/407,390.
US Final Office Action dated Sep. 11, 2008 issued in U.S. Appl. No. 11/407,390.
US Office Action (Ex Parte Quayle) dated Aug. 14, 2009 issued in U.S. Appl. No. 11/407,390.
US Office Action (Examiner Interview Summary) dated Sep. 23, 2009 issued in U.S. Appl. No. 11/407,390.
US Notice of Allowance dated Dec. 2, 2009 issued in U.S. Appl. No. 11/407,390.
US Office Action dated Aug. 6, 2009 issued in U.S. Appl. No. 11/830,497.
US Office Action Final dated Feb. 9, 2010 issued in U.S. Appl. No. 11/830,497.
US Office Action dated Nov. 1, 2010 issued in U.S. Appl. No. 11/830,497.
US Office Action (Ex Parte Quayle) dated Apr. 14, 2011 issued in U.S. Appl. No. 11/830,497.
US Notice of Allowance dated Jun. 21, 2011 issued in U.S. Appl. No. 11/830,497.
US Office Action dated Nov. 24, 2009 issued in U.S. Appl. No. 11/950,315.
US Office Action Final dated Jun. 16, 2010 issued in U.S. Appl. No. 11/950,315.
US Office Action dated Feb. 9, 2011 issued in U.S. Appl. No. 11/950,315.
US Office Action Final Sep. 12, 2011 issued in issued in U.S. Appl. No. 11/950,315.
Anantharamaiah and Garber, (1996) "Chromatographic Methods for Quantitation of Apolipoprotein A-I", *Meth Enzymol* 263: 267-282.
Anantharamaiah et al., (1985) "Studies of Synthetic Peptide Analogs of the Amphipathic Helix", *The Journal of Biological Chemistry*, 260(18):10248-10255.
Anantharamaiah et al., (1990) "Use of Synthetic Peptide Analogues to Localize Lecithin: Cholesterol Acyltransferase Activating Domain in Apolipoprotein A-I", *Arteriosclerosis* 10:95-105.
Anantharamaiah et al. (1993) "An Atlas of the Amphipathic Helical Domains of Human Exchangeable Plasma Apolipoproteins", Chapter 6:109-142 In: The Amphipathic Helix (Epand, R. M., ed), *CRC Press*, Boca Raton, FL.
Anantharamaiah (1986) "Synthetic Peptide Analogs of Apolipoproteins", *Methods in Enzymology*, 128:627-647.
Anantharamaiah et al. (2007) "Structural requirements for antioxidative and anti-inflammatory properties of apolipoprotein A-1 Mimetic peptides", *Journal of Lipid Research*, 48:1915-1923.
Anderson et al. (1989) "Structure of Human Lactoferrin: Crystallographic Structure Analysis and Refinement at 2.8 Å Resolution", *J Mol Biol*, 209:711-734.
Aoyagi et al. (1988) "Synthesis of antibacterial peptides-gramicidin S analogs and designed amphiphilic oligopeptides", *Tetrahedron*; 44:877-886.

Aravinda et al., (2003) "Aromatic-Aromatic Interactions in Crystal Structures of Helical Peptide Scaffolds Containing Projecting Phenylalinine Residues", *J Am Chem Soc*, 125(18):5308-5315.
Armstrong et al., (1993) "D-Amino Acid Levels in Human Physiological Fluids", *Chirality*, 5: 375-378.
Ashby et al., (2001) "Lack of effect of serum amyloid A (SAA) on the ability of high-density lipoproteins to inhibit endothelial cell adhesion molecule expression", *Atherosclerosis*, 154:113-121.
Ashby et al., (1998) "Factors Influencing the Ability of HDL to Inhibit Expression of Vascular Cell Adhesion Molecule-1 in Endothelial Cells", *Arteriosclerosis, Thrombosis and Vascular Biology*, 18:1450-1455.
Asokan et al. (1989) "Separation and evaluation of changing pattern of glycosaminoglycans in 3-methyl cholanthrene induced fibrosarcoma", *Neoplasma* 36(3):273-9.
Asokan et al., (Apr. 21, 1993) "Purification and characterization of collagens from rat fibrosarcoma induced by 3-methylcholanthrene", *Mol Cell Biochem*, 121(2):99-107.
Badimon et al., (1990) "Regression of Atherosclerotic Lesions by High Density Lipoprotein Plasma Fraction in the Cholesterol-fed Rabbit", *J Clinical Investigation*, 85:1234-1241.
Baker et al., (1999) "Ability of reconstituted high density lipoproteins to inhibit cytokine-induced expression of vascular cell adhesion molecule-1 in human umbilical vein endothelial cells", *Journal of Lipid Research*, 40:345-353.
Baker et al., (2000) "Phospholipid composition of reconstituted high density lipoproteins influences their ability to inhibit endothelial cell adhesion molecule expression", *J Lipid Res*, 41:1261-1267.
Barter et al., (2002) "Effect of high-density lipoproteins on the expression of adhesion molecules in endothelial cells", *Current Opinion in Lipidology*, 13:285-288.
Barter et al., (1996) "High density lipoproteins and coronary heart disease", *Atherosclerosis*, 121:1-12.
Bauer et al., (1982) "SMS 201-995: A Very Potent and Selective Octapeptide Analogue of Somatostatin with Prolonged Action", *Life Sciences*, 31:1133-1140.
Baumbach et al., (2002) "Structure of Cerebral Arterioles in Cystathionine 13Synthase-Deficient Mice", *Circulation Res.*, 91:931-937.
Baumbach et al., (2003) "Cerebral Arteriolar Structure in Mice Overexpressing Human Renin and Angiotensinogen", *Hypertension*, 41:50-55.
Bergt et al. (Feb. 27, 2004) "Lysine Residues Direct the Chlorination of Tyrosines in YXXK Motifs of Apolipoprotein A-I When Hypochlorous Acid Oxidizes High Density Lipoprotein", *The Journal of Biological Chemistry*, 279(9):7856-7866.
Bisoendial et al., (2003) "Restoration of Endothelial Function by Increasing High-Density Lipoprotein in Subjects With Isolated Low High-Density Lipoprotein", *Circulation* 107:2944-2948.
Blankenberg et al., (2001) "Circulating Cell Adhesion Molecules and Death in Patients with Coronary Artery Disease", *Circulation*, 104:1336-1342.
Boffelli et al., (1997) "Reconstitution and Further Characterization of the Cholesterol Transport Activity of the Small-Intestinal Brush Border Membrane", *Biochemistry*, 36:10784-10792.
Boffelli et al., (1997) "The uptake of cholesterol at the small-intestinal brush border membrane is inhibited by apolipoproteins", *FEBS Letters*, 411:7-11.
Borhani et al., (1997) "Crystal structure of truncated human apolipoprotein A-I suggests a lipid-bound conformation", Biochemistry, *PNAS* USA, 94:12291-12296.
Bourdillon et al., (2000) " ICAM-1 Deficiency Reduces Atherosclerotic Lesions in Double-Knockout Mice (ApoE$^{-/-}$ /ICAM-1$^{-/-}$) Fed a Fat or a Chow Diet", *Arterioscler Thromb Vasc Biol*, 20:2630-2635.
Bowry et al., (1992) "High density lipoprotein is the major carrier of lipid hydroperoxides in human blood plasma from fasting donors", *PNAS* USA, 89:1031610320.
Brouillette and Anantharamaiah, (1995) "Structural models of human apolipoprotein A-I" *Biochim Biophys Acta*, 1256: 103-129.
Brouillette et al., (2001) "Structural Models of Human Apolipoprotein A-I: A Critical Analysis and Review", *Biochemica et Biophysica Acta*, 1531:4-46.

Burger et al., (2002) "High-density lipoprotein-associated apolipoprotein A-I: the missing link between infection and chronic inflammation?", *Autoimmunity Reviews*, 1:111-117.

Calabresi et al., (1997) "Inhibition of VCAM-1 Expression in Endothelial Cells by Reconstituted High Density Lipoproteins", *Biochem and Biophys Res Commun*, 238:61-65.

Calabresi et al., (2002) "Elevated Soluble Cellular Adhesion Molecules in Subjects With Low HDL-Cholesterol", *Arterioscler Thromb Vasc Biol*, 22:656-661.

Campbell EJ, (1982) "Human leukocyte elastase, cathepesin G and lactoferrin: Family of neutrophil granule glycoproteins that bind to an alveolar macrophage receptor", *PNAS* USA; 79:6941-6945.

Canadian Pharmacists Association, Starlix® $^{Pr}$ General Monograph (2002), 12 pages http://cpha.infinetcomm.com/content/hcp/tools/cps_cnp_updates/starlix.cfm.

Carlos et al., (1990) "Vascular cell adhesion molecule-1 mediates lymphocyte adherence to cytokine-activated cultured human endothelial cells", *Blood*, 76(5):965-970.

Carr et al., (2000) "Oxidation of LDL by myeloperoxidase and reactive nitrogen species", *Arterioscler Thromb Vasc Biol*, 20:1716-1723.

Casserly and Topol (2004) "Convergence of atherosclerosis and Alzheimer's disease: inflammation, cholesterol, and misfolded proteins", *Lancet* 363: 1139-1146.

Castelli et al., (1986) "Incidence of coronary heart disease and lipoprotein cholesterol levels. The Framingham Study", *JAMA*, 256(20):2835-2838.

Charles-Schoeman et al., (2008) "Treatment with an apolipoprotein A-1 mimetic peptide in combination with pravastatin inhibits collagen-induced arthritis", *Clinical Immunology*, 127:234-244.

Chiesa et al., (2002) "Recombinant Apolipoprotein A-I $_{Milano}$ Infusion Into Rabbit Carotid Artery Rapidly Removes Lipid from Fatty Streaks", *Circ Res*, 90:974-980.

Chillon and Baumbach (1999) "Effects of an Angiotensin-Converting Enzyme Inhibitor and a β-Blocker on Cerebral Arterioles in Rats", *Hypertension* 33: 856-861.

Christison et al., (1996) "Rapid reduction and removal of HDL-but not LDL-associated cholesteryl ester hydroperoxides by rat liver perfused in situ", *Biochem J*, 314:739-742.

Chung et al. (1985) "Studies of Synthetic Peptide Analogs of the Amphipathic Helix" *J Biol Chem*, 260(18):10256-10262.

Clay et al., (2001) "Time sequence of the inhibition of endothelial adhesion molecule expression by reconstituted high density lipoproteins", *Atherosclerosis*, 157:23-29.

Cockerill et al., (2001) "Elevation of Plasma High-Density Lipoprotein Concentration Reduces Interleukin-1-Induced Expression of E-Selectin in an in Vivo Model of Acute Inflammation", *Circulation*, 103:108-112.

Cockerill et al., (1995) "High-Density Lipoproteins Inhibit Cytokine-Induced Expression of Endothelial Cell Adhesion Molecules", *Arterioscler Thromb Vasc Biol*, 15:1987-1994.

Cockerill et al., (1999) "High-Density Lipoproteins Differentially Modulate Cytokine-Induced Expression of E-Selectin and Cyclooxygenase-2", *Arterioscler Thromb Vasc Biol*, 19:910-917.

Coyne et al. (2002) "Methods for isolation and characterization of intracerebral arterioles in the C57/BL6 wild-type mouse", *J. Neurosci. Meth.*, 120: 145-153.

Cybulsky et al., (2001) "A major role for VCAM-1, but not ICAM-1, in early atherosclerosis", *Journal of Clinical Investigation*, 107(10):1255-1262.

Cyrus et al., (2001) "Absence of 12/15-Lipoxygenase Expression Decreases Lipid Peroxidation and Atherogenesis in Apolipoprotein E-Deficient Mice", *Circulation*, 103:2277-2282.

Dansky et al., (2001) "Adhesion of Monocytes to Arterial Endothelium and Initiation of Atherosclerosis are Critically Dependent on Vascular Cell Adhesion Molecule-1 Gene Dosage", *Arterioscler Thromb Vasc Biol*, 21:1662-1667.

Dansky et al., (1999) "Apo A-I inhibits foam cell formation in Apo E-deficient mice after monocyte adherence to endothelium", *J Clin Invest*, 104:31-39.

Datta et al., (Jan. 1, 2001) "Effects of increasing hydrophobicity on the physical-chemical and biological properties of a class A amphipathic helical peptide", *J Lipid Research*, 42:1096-1104.

Datta et al. (2004) "Aromatic Residue Position on the Nonpolar Face of Class A Amphipathic Helical Peptides Determines Biological Activity", *Journal of Biological Chemistry*, 279(24):26509-26517.

Davenport et al. (2003) "The Role of Interleukin-4 and Interleukin-12 in the Progression of Atherosclerosis in Apolipoprotein E-Deficient Mice", *Am J Pathol*, 163(3):1117-1125.

Davidson et al. (1994) "The Influence of Apolipoprotein Structure on the Efflux of Cellular Free Cholesterol to High Density Lipoprotein", *J Biol Chem*, 269(37):22975-22982.

Davies et al., (1993) "The expression of the adhesion molecules ICAM-1, VCAM-1, PECAM, and E-selectin in human atherosclerosis", *J Pathol*, 171(3):223-229.

De Caterina et al., (1998) "Structural requirements for inhibition of cytokine-induced endothelial activation by unsaturated fatty acids", *J Lipid Res*, 39:1062-1070.

de la Tone and Mussivand (1993) "Can disturbed brain microcirculation cause Alzheimer's disease?", *Neurol. Res.*, 15(3): 146-153.

Diederich et al., (2001) "Apolipoprotein A1 and HDL3 Inhibit Spreading of Primary Human Monocytes through a Mechanism that Involves Cholesterol Depletion and Regulation C160 of CD42", *Atherosclerosis*, 159:313-324.

Dimayuga et al., (1999) "Reconstituted HDL Containing Human Apolipoprotein A-1 Reduces VCAM-1 Expression and Neointima Formation Following Periadventitial Cuff-Induced Carotid Injury in apoE Null Mice", *Biochem Biophys Res Commun*, 264(2):465-468.

Dooley et al., (1994) "An All D-Amino Acid Opioid Peptide with Central Analgesic Activity from a Combinatorial Library", *Science*, 266:2019-2022.

Drouet L et al., (1990) "The antithrombotic effect of KRDS, a lactotransferrin peptide, compared RGDS", *Nouv. Rev. fr. Hematol*, 32:59-62.

Dunlop and Neidle and Neidle, (1997) "The Origin and Turnover of D-Serine in Brain," *Biochemical and Biophysical Research Communication*, 235:26-30.

Ehara et al., (2001) "Elevated Levels of Oxidized Low Density Lipoprotein Show a Positive Relationship With the Severity of Acute Coronary Syndromes", *Circulation*, 103:1955-1960.

Epand et al., (1987) "Studies of Synthetic Peptide Analogs of the Amphipathic Helix", *Journal of Biological Chemistry*, 262(19):9389-9396.

Epand RM, Stafford A, Leon B, Lock PE, Tytler EM, Segrest JP, Anantharamaiah GM, (1994) "HDL and apolipoprotein A-I protect erythrocytes against the generation of procoagulant activity", *Arterioscler Thromb*, 14(11):1775-1783.

Field et al., (2001) "Gene expression of sterol regulatory element-binding proteins in hamster small intestine", *Journal of Lipid Research*, 42:1-9.

Fielding and Fielding (1995) "Molecular physiology of reverse cholesterol transport", *Journal of Lipid Res*, 36: 211-228.

Fielding et al., (1972) "A Protein Cofactor of Lecithin: Cholesterol Acyltransferase", *Biochemical and Biophysical Research Comm*, 46(4):1493-1498.

Flaherty et al., (Feb. 1999) "Acute pancreatitis as a complication of polyarteritis Nodosa", *Intnl Jnl of Panc.*, 25(1):53-57.

Fleisher LN, Tall AR, Witte LD, Miller RW, Cannon PJ, (1982) "Stimulation of Arterial Endothelial Cell Prostacyclin Synthesis by High Density Lipoproteins", *Journal of Biol Chem*, 257:6653-6655.

Fogelman (retrieved from http://www.ekatius.com/i/presentations/details/050406/05A on Jan. 13, 2009 corresponding transcription (pp. 2-7 of the document) and powerpoint presentation (pp. 8-68) total of 68 pages).

Fogelman AM, (2004) "When good cholesterol goes bad", *Nat Med*, 10(9):902-903.

Fogelman AM, Shechter I, Seager J, Hokom M, Child JS, Edwards PA, (1980) "Malondialdehyde alteration of low density lipoproteins leads to cholesteryl ester accumulation in human monocyte-macrophages", *PNAS* USA, 77(4):2214-2218.

Forte TM, Subbanagounder G, Berliner JA, Blanche PJ, Clermont AO, Jia Z, Oda MN, Krauss RM, Bielicki JK, (2002) "Altered activities of anti-atherogenic enzymes LCAT, paraoxonase, and platelet-activating factor acetylhydrolase in atherosclerosis-susceptible mice", *J Lipid Res*, 43:477-485.

Fricker et al., (1995) "Enteral Absorption of Octreotide: Modulation of Intestinal Permeability Distinct Carbohydrates", *The Journal of Pharmacology and Experimental Therapeutics*, 274(2): 826-832.
Fuessl et al., (1987) "Oral absorption of the somatostatin analogue Sms 201-995: theoretical and practical implications", *Clinical Science*, 72:255-257.
Fukuda et al., (1990) "Bilayer forming ion-pair amphi-philes from single chain surfactants"; *J Am Chem Soc.*, 112:1635-1637.
Futterman, et al., (May 2004) "Statin Pleiotropy: Fact or Fiction?", *Am J Crit Care*, 13(3):244-249.
Gabay C, Kushner I, (1999) "Acute-Phase Proteins and Other Systemic Responses to Inflammation", *N Engl J. Med*, 340(6):448-454.
Garber et al., (1992) "Turnover of Synthetic Class a Amphipathic Peptide Analogues of Exchangeable Apolipoproteins in Rats, Correlation with Physical Properties", *Arteriosclerosis and Thrombosis*, 12(8):886-894.
Garber et al., (1997) "Anti -Atherogenic Properties of a Model Amphipathic Helical Peptide: Studies in Transgenic Mice", *Supplement to Circulation*, 96(8): No. 2744.
Garber et al., (1999) "Protection against Atherosclerosis in Mice by a Synthetic Class a Amphipathic Peptide Analog of Apolipoprotein A-I", *Circulation*, 100(18):2838.
Garber et al., (2001) "A new synthetic class a amphipathic peptide analogue protects mice from diet-induced atherosclerosis", *Journal of Lipid Research*, 42:545-552.
Garner et al., (1998) "Oxidation of High Density Lipoproteins. II. Evidence for Direct Reduction of Lipid Hydroperoxides by Methionine Residues of Apolipoproteins AI and AII", *J Biol Chem*, 273(11):6088-6095.
Garner et al., (1998) "Oxidation of high density lipoproteins. I. Formation of methionine sulfoxide in apolipoproteins at and an is an early event that accompanies lipid peroxidation and can be enhanced by α-tocopherol", *J Biol Chem*, 273(11):6080-6087.
Gaut et al., (2002) "Myeloperoxidase produces nitrating oxidants in vivo", *J Clin Invest* 109(10):1311-1319.
George et al., (2001) "12/15-Lipoxygenase Gene Disruption Attenuates Atherogenesis in LDL Receptor-Deficient Mice", *Circulation*, 104:1646-1650.
Getz et al., (2009) "Apoprotein A-1 mimetic peptides and their potential anti-atherogenic mechanisms of action", *Current Opinion in Lipidology*, 20:1-5.
Ghersi-Egea et al., (1996) "Fate of Cerebrospinal Fluid-Borne Amyloid B-Peptide: Rapid Clearance into Blood and Appreciable Accumulation by Cerebral Arteries", *J. Neurochem*, 67: 880-883.
Glomset, (1968) "The Plasma lecithin: cholesterol acyltransferase reaction", *J Lipid Res* 9:155-167.
Gong et al., (1994) "Structural and functional properties of human and mouse apolipoprotein A-I", *Biochim Biophys Acta*, 1213:335-342.
Gordon et al., (1977) "High density lipoprotein as a protective factor against coronary heart disease. The Framingham Study", *Am J Med*, 62(5):707-714.
Graf et al., (Oct. 1996) "Random circular permutation of genes and expressed polypeptide chains: Application of the method to the catalytic chains of aspartate transcarbamoylase", *Proc. Natl. Acad. Sci. USA, Biochemistry*, 93:11591-11596.
Gurfinkel et al., (2002) "Influenza Vaccine Pilot Study in Acute Coronary Syndromes and Planned Percutaneous Coronary Interventions. The FLU Vaccination Acute Coronary Syndromes (FLUVACS) Study", *Circulation*, 105:2143-2147.
Hamase et al. (2001) "Determination of Free D-Proline and D-Leucine in the Brains of Mutant Mice Lacking D-Amino Acid Oxidase Activity", *Analytical Biochemistry* 298:253-258.
Harats et al., (2000) "Overexpression of 15-Lipoxygenase in Vascular Endothelium Accelerates Early Atherosclerosis in LDL Receptor-Deficient Mice", *Arterioscler Thromb Vasc Biol*, 20:2100-2105.
Hardy et al., (2001) "An Automated High-Performance Liquid Chromatography Procedure for the Quantitation of L- and D-Amino Acids by Means of Stepwise Precolumn Derivatization", *Analytical Biochemistry*, 291:297-299.
Harkin et al. (1997) the Effects of hyper-and hypocarbia on intraparenchymal arterioles in rat brain slices, *Neuroreport*, 8:1841-1844.

Hashimoto et al., (2000) "Improvement of intestinal absorption of peptides: absorption of B1-Phe monoglucosylated insulin to rat intestinal brush-border membrane vesicles", *European Journal of Pharmaceutics & Biopharmaceutics*, 50:197-204.
Hauser et al., (1998) "Identification of a Receptor Mediating Absorption of Dietary Cholesterol in the Intestine", *Biochemistry*, 37(51):17843-17850.
Hayry et al., (1995) "Stabile D-peptide analog of insulin-like growth factor-1 inhibits smooth muscle cell proliferation after carotid ballooning injury in the rat", *FASEB J*, 9(13):1336-1344.
Hein et al., (2001) "Integrin-binding peptides containing Rgd produce coronary arteriolar dilation via cyclooxygenase activation", *Am J Physiol Heart Circ Physiol*, 281:H2378-H2384.
Hemachander et al., (Mar. 1, 2000) "Lipase from *Ralstonia pickettii* as an additive in laundry detergent formulations", *Process Biochem.* 35(8):809-814.
Henricksen et al., (1981) "Enhanced macrophage degradation of low density lipoprotein previously incubated with cultured endothelial cells: Recognition by receptor for acetylated low density lipoproteins", *PNAS* USA, 78(10):6499-6503.
Hessler et al., (1979) "LDL-induced cytotoxicity and its inhibition by HDL in human vascular smooth muscle and endothelial cells in culture", *Atherosclerosis*, 32(3):213-229.
Hoffman et al., (1997) "Isoprostanes: Free Radical-Generated Prostaglandins with constrictor Effects on cerebral Arterioles", *Stroke*, 28:844-849.
Hwang et al., (1997) "Circulating Adhesion Molecules VCAM-1, ICAM-1, and Eselectin in Carotid Atherosclerosis and Incident Coronary Heart Disease Cases. The Atherosclerosis Risk in Communities (ARIC) Study", *Circulation*, 96:4219-4225.
Hyka et al., (2001) "Apolipoprotein A-I Inhibits the Production of Interleukin-4 1β and Tumor Necrosis Factor-α by Blocking Contact-Mediated Activation of Monocytes by T Lymphocytes", *Blood*, 97(8):2381-2389.
Israelachvili et al. (1980) "Physical principles of membrane organization", *Q Rev Biophys*, 13:121-200.
Jamaluddin, et al. (1987) "Aggregatory reactions of blood platelets in unstirred dilute suspensions and their monitoring by spectrophotometry", *Curr Sci*, 56:254-256.
Jamieson et al., (2001) "Detection of Lipoprotein (a) in Intraparenchymal Cerebral Vessels: Correlation with Vascular Pathology and Clinical History", *Exp. Mol. Pathol.*, 71: 99-105.
Jin et al., (2003) "Inhibition of endothelial lipase causes increased HDL cholesterol levels in vivo", *J Clin Invest*, 111(3):357-362.
Johnson et al., (1991) "Cholesterol transport between cells and high-density lipoproteins", *Biochem Biophys Acta*, 1085:273-298.
Jonas, (1991) "Lecithin-cholesterol acyltransferase in the metabolism of high-density lipoproteins", *Biochim Biophys Acta*, 1084:205-220.
Jonas, (2000) "Lecithin cholesterol acyltransferase", *Biochem Biophys Acta*, 1529:245-256.
Jones et al., (1992) "Computer Programs to Identify and Classify Amphipathic α Helical Domains", *Journal of Lipid Research*, 33:287-296.
Kaler et al., (1989) "Spontaneous vesicle formation in aqueous mixtures of single-tailed surfactants", *Science*, 245:1371-1374.
Karle et al., (2003) "Crystal structure of hydrophobic 19-residue peptide helix containing three centrally located D amino acids", *PNAS*, 100(24):13946-13951.
Karle et al., (2004) "A combined extended and helical backbone for Boc-(Ala-Leu-Ac7c-)2-OMe", *J Peptide Res*, 63:175-180.
Kigasawa et al., (1995) "Inhibition of corneal ulceration by tetrapeptidyl hydroxamic acid", *Japanese Journal Ophthamology*, 39(1):35-42.
Ko et al., (1993) "High-density lipoprotein reduces epidermal growth factor-induced DNA synthesis in vascular smooth muscle cells", *Atherosclerosis*, 99(2):253-259.
Kontos and Wei, (1998) "Cerebral arteriolar dilations by $K_{ATP}$ channel activators need L-lysine or L-arginine" *Am. J. Physiol.* 274 (*Heart Circ. Physiol.* 43): H974-H981.
Kreiger, (1999) "Charting the Fate of the "Good Cholesterol": Identification and Characterization of the High-Density Lipoprotein Receptor SR-Bi", *Annu Rev Biochem*, 68:523-558.

Kruger et al. (2005) "D-4F Induces Heme Oxygenase-1 and Extracellular Superoxide Dismutase, Decreases Endothelial Cell Sloughing, and Improves Vascular Reactivity in Rat Model of Diabetes", *Circulation*, 111(23):3126-3134.

Kuller et al. (1991) "The Relation between Serum Albumin Levels and Risk of Coronary Heart Disease in the Multiple Risk Factor Intervention Trial", *American Journal of Epidemiology*, 134(11):1266-1277.

Kullman et al., (1999) "Evaluation of the Enantiomeric Composition of Amino Acids in Tobacco", *Chirality* 11:669-673.

Kumar et al., (Jan. 2002) "A novel peptide derivative exhibits anti-inflammatory and antioxidant activity in adjuvant induced arthritis in rats", *Mol Cell Biochem*, 229(1-2):9-17.

Kume et al., (1992) "Lysophosphatidylcholine, a Component of Atherogenic Lipoproteins, Induces Mononuclear Leukocyte Adhesion Molecules in Cultured Human and Rabbit Arterial Endothelial Cells", *Journal of Clinical Investigation*, 90:1138-1144.

Langer et al., (1992) "Somatic cell mapping of the bovine interferon-alpha receptor", *Mamm Genome*, 3(4):237-40.

Latimer et al., (1977) "Application of light scattering theory to the optical effects associated with the morphology of blood platelets", *Arch Biochem Biophys*, 180:151-159.

Lawrence et al., (1991) "Leukocytes roll on a selectin at physiologic flow rates: distinction from and prerequisite for adhesion through integrins", *Cell*, 65(5):859-873.

Lee et al., (2001) "Vitamin C-Induced Decomposition of Lipid Hydroperoxides to Endogenous Genotoxins", *Science*, 292:2083-2086.

Legrand et al., (1992) "Molecular Interactions between Human Lactotransferrin and the Phytohemagglutinin-Activated Human Lymphocyte Lactotransferrin Receptor Lie in Two Loop-Containing Regions of the N-Terminal Domain I of Human Lactotransferrin", *Biochemistry*, 31:9243-9251.

Levi et al., (2000) "A Retro-Inverso Miniantibody with Anti-HIV Activity", *Aids Res & Human Retroviruses*, 16(1):59-65.

Levine et al., (1993) "In vivo protection against endotoxin by plasma high density lipoprotein", *PNAS USA*, 90:12040-12044.

Li et al., (1993) "An atherogenic diet rapidly induces VCAM-1, a cytokine-regulatable mononuclear leukocyte adhesion molecule, in rabbit aortic endothelium", *Arterioscler Thrombosis*, 13(2):197-204.

Libby et al., (2002) "Inflammation and Atherosclerosis", *Circulation*, 105:1135-1143.

Lumsden et al., (1997) "Anti-VLA-4 antibody reduces intimal hyperplasia in the endarterectomized carotid artery in nonhuman primates", *J Vasc Surg*, 26(1):87-93.

Lundin et al., (1986) "Absorption of Intragastrically Administered DDAVP in Conscious Dogs", *Life Sciences*, 38(8):703-709.

Mach et al., (1998) "Reduction of atherosclerosis in mice by inhibition of CD40 signalling", *Nature*, 394:200-203.

Mala, John Geraldine Sandana et al., (Aug. 2001) "Strain improvement of *Aspergillus niger* for enhanced lipase production", *J Gen Appl Microbiol*, 47(4):181-186.

Man et al., (1987) "D-Aspartate in Human Brain", *J of Neurochem*, 48(2):510-515.

Manikandan et al. (2002) "Antioxidant Potential of a Novel Tetrapeptide Derivative in Isoproterenol-Induced Myocardial Necrosis in Rats", *Pharmacology*, 65:103-109.

Mato et al., (Apr. 1996) "Involvement of specific macrophage-lineage cells surrounding arterioles in barrier and scavenger function in brain cortex", *PNAS USA*, 93:3269-3274.

Mazoyer et al., (1990) "KRDS, a new peptide derived from human lactotransferrin, inhibits platelet aggregation and release reaction", *Eur J Biochem* 194:43-49.

Meera et al. (Sep. 1999) "Inhibition of neutrophil derived lysosomal enzymes and reactive oxygen species by a novel tetrapeptide", *Inflamm Res*, 48(9):479-484.

Mehrabian et al., (2002) "Identification of 5-Lipoxygenase as a Major Gene Contributing to Atherosclerosis Susceptibility in Mice", *Circ Res*, 91:120-126.

Merrifield et al., (1995) "Retro and Retroenantio Analogs of Cecropin-Melittin Hybrids", *PNAS USA*, 92:3449-3453.

Meyrier et al. (1998) "Ischemic renal diseases: New insights into old entities", *Kidney International*, 54:2-13.

Mishra et al., (1994) "Interaction of Synthetic Peptide Analogs of the Class A", *J Biol Chem*, 269(10):7185-7191.

Mishra et al., (1995) "Effect of the Arrangement of Tandem Repeating Units of Class a Amphipathic alpha-Helixes on Lipid Interaction", *J Biol Chem*, 270(4):1602-1611.

Mishra et al., (1998) "Studies of Synthetic Peptides of Human Apolipoprotein A-I Tandem Amphipathic alpha-Helixes", *Biochemistry*, 37:10313-10324.

Moody et al., (Sep. 1997) "Cerebral Microvascular Alterations in Aging, Leukoaraiosis, and Alzheimer's Disease", *Annals of the New York Academy of Sciences*, 826:103-116.

Mor et al. (1992) "Enter a new post-translational modification: D-amino acids in gene-encoded peptides", *TIBS*, 17:481-485.

Moro and Rodriguez (1991) "Application of Phase Separation and Mass Action Models to Low Aggregation No. Micelles: A Comparative Study", *Langmuir*, 7:2017-2020.

Mulder et al. (2004) "Low-density lipoprotein receptor-knockout mice display impaired spatial memory associated with a decreased synaptic density in the hippocampus", *Neurobiology of Disease* 16: 212-219.

Murugesan G, Sa G, Fox PL, (1994) "High-density lipoprotein stimulates endothelial cell movement by a mechanism distinct from basic fibroblast growth factor", *Circ Res*, 74(6):1149-1156.

Nag (1996) "Immunohistochemical Localization of Extracellular Matrix Proteins in Cerebral Vessels in Chronic Hypertension", *J. Neuropath. Exp. Neurol.*, 55(3):381-388.

Nag et al. (1997) "Cerebrovascular Changes in Chronic Hypertension, Protective Effects of Enalapril in Rats", *Stroke*, 28:1028-1034.

Nagata et al. (1995) "Free D-Serine Concentration in Normal and Alzheimer Human Brain", *Brain Res. Bull.*, 38(2):181-183.

Nagata et al. (2002) "Hemodynamic Aspects of Alzheimer's Disease", *Ann. N.Y. Acad. Sci.*, 977: 391-402.

Nagata et al., (1994) "Distribution of free D-serine in vertebrate brains", *Brain Res*, 634: 291-295.

Naghavi et al., (2003) "Influenza Infection Exerts Prominent Inflammatory and Thrombotic Effects on the Atherosclerotic Plaques of Apolipoprotein E-Deficient Mice", *Circulation*, 107:762-768.

Nakamura et al., (1997) "Deposition of amyloid β protein (Aβ) subtypes [Aβ40 and Aβ42(43)] in canine senile plaques and cerebral amyloid angiopathy", *Acta Neuropathol*. 94:323-328.

Nanjee et al., (2001) "Intravenous apoA-I/lecithin discs increase pre-β-HDL concentration in tissue fluid and stimulate reverse cholesterol transport in humans", *J Lipid Res*, 42:1586-1593.

Nanjee et al., (1999) "Acute Effects of Intravenous Infusion of ApoAI/Phosphatidylcholine Discs on Plasma Lipoproteins in Humans", *Arterioscler Thromb Vasc Biol*, 19:979-989.

Navab et al. (Aug. 22, 2005) "Oral Small Peptides Render HDL Antiinflammatory in Mice, and Monkeys and Reduce Atherosclerosis in ApoE Null Mice", *Circ. Res.*(http://circres.ahajournals.org) 97:524-532.

Navab et al., (2000) "Normal high-density lipoprotein inhibits three steps in the formation of mildly oxidized low density lipoprotein: step 1", *J Lipid Res*, 41:1481-1494.

Navab et al., (2000) "Normal high-density lipoprotein inhibits three steps in the formation of mildly oxidized low density lipoprotein: steps 2 and 3", *J Lipid Res*, 41:1495-1508.

Navab et al., (Jan. 22, 2002) "Oral Administration of an Apo A-I Mimetic Peptide Synthesized from D-Amino Acids Dramatically Reduces Atherosclerosis in Mice Independent of Plasma Cholesterol", *Circulation*, 105(3):290-292.

Navab et al., (2004) "Oral D-4F Causes Formation of Pre-β High-Density Lipoprotein and Improves High-Density Lipoprotein-Mediated Cholesterol Efflux and Reverse Cholesterol Transport From Macrophages in Apolioprotein E-Null Mice", *Circulation*, 109:r120-r125.

Navab et al., (2004) "The oxidation hypothesis of artherogenesis: the role of oxidized phospholipids and HDL", *Journal Lipid Res*, 45:993-1007.

Navab et al. (2001) "HDL and the Inflammatory Response Induced by LDL-Derived Oxidized Phospholipids", *Arterioscler Thromb Vasc Biol*, 21:481-488.

Navab et al., (2003) "Oral Synthetic Phospholipids (DMPC) Raises High-Density Lipoprotein Cholesterol Levels, Improves High-Density Lipoprotein Function, and Markedly Reduces Atherosclerosis in Apolipoprotein E-Null Mice", *Circulation*, 108:1735-1739.

Navab et al., (2001) "A cell-free assay for detecting HDL that is dysfunctional in preventing the formation of or inactivating oxidized phospholipids", *Journal Lipid Res*, 42(8):1308-1317.

Navab et al., (1997) "Mildly Oxidized LDL Induces an Increased Apolipoprotein J/Paraoxonase Ratio", *J Clin Invest*, 99(8):2005-2019.

Navab et al., (1991) "Monocyte Transmigration Induced by Modification of Low Density Lipoprotein in Cocultures of Human Aortic Wall Cells is due to Induction of Monocyte Chemotactic Protein 1 Synthesis and is Abolished by High Density Lipoprotein", *Journal of Clinical Investigation*, 88:2039-2046.

Nievelstein et al., (1991) "Lipid accumulation in rabbit aortic intima two hours after bolus infusion of low density lipoprotein: A deep-etch and immuno-localization study of ultra-rapidly frozen tissue", *Arteriosclerosis and Thrombosis*, 11(6):1795-1805.

Nirmala and Puvanakrishnan, (1996) "Effect of Curcumin on Certain Lysosomal Hydrolases in Isoproterenol-Induced Myocardial Infarction in Rats", *Biochem Pharmacol.*, 51(1):47-51.

Nirmala and Puvanakrishnan (1996) "Protective role of curcumin against isoproterenol induced myocardial infarction in rats", *Mol Cell Biochem.*, 159(2):85-93.

Nirmala and Puvanakrishnan (Aug. 1998) Collagen profile in isoproterenol induced myocardial necrosis in rats, *Indian J Exp Biol.*, 36:763-767.

Nirmala et al. (1999) "Curcumin treatment modulates collagen metabolism in isoproterenol induced myocardial necrosis in rats", *Mol Cell Bioche*, 197:31-37.

Nomoto et al., (1998) "Improvement of Intestinal Absorption of Peptide Drugs by Glycosylation: Transport of Tetrapeptide by the Sodium Ion-Dependent D-Glucose Transporter", *J Phannaceutical Science*, 87(3):326-332.

O'Brien et al., (1996) "Neovascular Expression of E-Selectin, Intercellular Adhesion Molecule-1, and Vascular Cell Adhesion Molecule-1 in Human Atherosclerosis and their Relation to Intimal Leukocyte Content", *Circulation*, 93:672-82.

O'Connell BJ, Genest J Jr., (2001) "High-Density Lipoproteins and Endothelial Function", *Circulation*, 104:1978-1983.

Oguchi et al., (2000) "Monoclonal Antibody Against Vascular Cell Adhesion Molecule-1 Inhibits Neointimal Formation After Periadventitial Carotid Artery Injury in Genetically Hypercholesterolemic Mice", *Arterioscler Thromb Vasc Biol*, 20:1729-1736.

Ohkuma et al. (1997) "Morphological Changes of Intraparenchymal Arterioles After Experimental Subarachnoid Hemorrhage in Dogs", *Neurosurgery*, 41(1): 230-236.

Ohtani et al. (1995) "Age-related changes in D-aspartic acid of rat teeth", *Growth Develop & Aging*, 59:55-61.

Opeskin (1996) "Cerebral Amyloid Angiopathy", *Am. J. Forensic Med. & Pathol.*, 17(3): 248-254.

Oram and Yokoyama, (1996) "Apolipoprotein-mediated removal of cellular cholesterol and phospholipids", *J Lipid Res*, 37: 2473-2491.

Ou et al. (2005) "Effects of D-4F on Vasodilation and Vessel Wall Thickness in Hyperholesterolemic LDL Receptor—Null and LDL Receptor/Apolipoprotein A-I Double-Knockout Mice on Western Diet", *Circ. Res.* 97:1190-1197.

Ou et al., (2003) "AP-4F, antennapedia peptide linked to an amphipathic α helical peptide, increases the efficiency of Lipofectamine-mediated gene transfection in endothelial cells", *Biochem Biophys Res Commun*, 305:605-610.

Ou et al., (2003) "L-4F, an Apolipoprotein A-I Mimetic, Dramatically Improves Vasodilation in Hypercholesterolemia and Sickle Cell Disease", *Circulation*, 107(18):2337-2341.

Ou et al., (2003) "L-4F, an Apolipoprotein A-I Mimetic, Restores Nitric Oxide and Superoxide Anion Balance in Low-Density Lipoprotein-Treated Endothelial Cells", *Circulation*, 107:1520-1524.

Owens et al., (1990) "Apolipoprotein A-I and its Amphipathic Helix Peptide Analogues Inhibit Human Immunodeficiency Virus-induced Syncytium Formation", *J Clin Invest*, 86:1142-1150.

Paigen et al., (1990) "Atherosclerosis Susceptibility Differences among Progenitors of Recombinant Inbred Strains of Mice", *Arteriosclerosis*, 10:316-323.

Palgunachari et al., (1996) "Only the Two End Helixes of Eight Tandem Amphipathic Helical Domains of Human Apo A-I Have Significant Lipid Affinity. Implications for HDL Assembly", *Arteriosclerosis, Thrombosis, & Vascular Biology*, 16:328-338.

Panizzutti et al., (2001) "A new strategy to decrease N-methyl-D-aspartate (NMDA) receptor coactivation. Inhibition of D-serine synthesis by converting serine racemase into an eliminase", *PNAS* 98(9):5294-5299.

Papo et al., (2002) "The Consequence of Sequence Alteration of an Amphipathic α-Helical Antimicrobial Peptide and its Diastereomers", *J Biol Chem*, 277(37): 33913-33921.

Pappenheimer et al., (1994) "Intestinal absorption and excretion of octapeptides composed of D amino acids", *PNAS USA* 91:1942-1945.

Pappenheimer et al., (1997) "Absorption and Excretion of Undegradable Peptides: Roles of Lipid Solubility and Net Charge", *J Pharmacology & Experimental Therapeutics*, 280(1):292-300.

Parthasarathy et al., (1994) "Mechanisms of oxidation antioxidants, and atherosclerosis", *Curr Opin Lipidol*, 5(5):371-375.

Pasqui et al., (2005) "Structural and functional abnormality of systemic microvessels in cardiac syndrome X", *Nutrition, Metabolism and Cardiovascular Diseases*, 15:56-64.

Pasceri et al., (2001) "Modulation of C-Reactive Protein-Mediated Monocyte Chemoattractant Protein-1 Induction in Human Endothelial cells by Anti-Atherosclerosis Drugs", *Circulation*, 103:2531-2534.

Pasceri V, Willerson JT, Yeh ET, (2000) "Direct Proinflammatory Effect of C-Reactive Protein on Human Endothelial Cells", *Circulation*, 102:2165-2168.

Paterno et al. (2004) "Reconstituted High-Density Lipoprotein Exhibits Neuroprotection in Two Rat Models of Stroke", *Cerebrovasc Dis.* 17(2-3):204-211, Epub Dec. 29, 2003.

Patszty et al., (1994) "Apolipoprotein AI Transgene Corrects Apolipoprotein E Deficiency-induced Atherosclerosis in Mice", *J Clinical Investigation*, 94:899-903.

Peng et al., (2001) "Effects of L-glutamate, D-aspartate, and monensin on glycolytic and oxidative glucose metabolism in mouse astrocyte cultures: further evidence that glutamate uptake is metabolically driven by oxidative metabolism", *Neurochemistry International*, 38:437-443.

Peterson et al. (2009) "The L-4F mimetic peptide prevents insulin resistance through increased levels of HO-1, pAMPK, and pAKT in obese mice", *J. Lipid Res.*, 50:1293-1304.

Pharmalicensing (Jan. 27, 2001) "Esperion Builds a Novel Peptides Program", 2 pages http://www.pharmalicensing.com/news/adisp/947888001_387f9f817c602.

Pharmalicensing (Jan. 28, 2001) "Multiple Peptide Systems Forms Joint Venture with Elan", 2 pages http://www.pharmalicensing.com/news/adisp/923742761_370f3229db152.

Pharmalicensing (Jan. 28, 2001) "Unigene to Receive Patent for Delivery of Peptide Pharmaceuticals" 2 pages http://www.pharmalicensing.com/news/adisp/952906240 38cc32009528f.

Philips et al., (1993) "Plasma Lipoproteins and Progression of Coronary Artery Disease Evaluated by Angiography and Clinical Events", *Circulation*, 88: 2762-2770.

Pilone, (2000) "D-amino acid oxidase: new findings", *CMLS, Cell Mol Life Sci*, 57:1732 1747.

Plump et al., (1994) "Human apolipoprotein A-I gene expression increases high density lipoprotein and suppresses atherosclerosis in the apolipoprotein E-deficient mouse", *PNAS USA*, 91:9607-9611.

Purdue News (Oct. 2000) 'Microspheres' Offer Promise for Oral Drug Delivery (3 pages).

Purdue News (Sep. 12, 1997) New Oral Insulin Delivery System Shows Promise (3 pages).

Puvanakrishnan and Bose, (Oct. 1984) "Immobilization of Pepsin on Sand: Preparation, Characterization and Application", *Indian J Biochem Biophys*, 21(5):323-6.

Puvanakrishnan and Langer (Jun. 1990) "Detection and Analysis of Interferon-alpha Receptors on Plasma Membranes and in Detergent Extracts", *J Interferon Res.*, 10(3):299-307.

Qian et al. (1995) "Isolation and characterization of sheep lactoferrin, an inhibitor of platelet aggregation and comparison with human lactoferrin", Biochim Biophys Acta, 1243:25-32.

Raha et al., (1988) "KRDS a Tetrapeptide Derived From Lactotransferrin Inhibits Binding of Monoclonal Antibody Against Glycoprotein IIb-IIIa on ADP-Stimulated Platelets and Megakaryocytes", Blood 72(1):172-178.

Rajashree and Puvanakrishnan (Jan. 1996) "Alterations in certain lysosomal glycohydrolases and cathepsins in rats on dexamethasone administration", Mol Cell Biochem, 154(2):165-70.

Rajashree and Puvanakrishnan, (Apr 1998) "Dexamethasone induced alterations in enzymatic and nonenzymatic antioxidant status in heart and kidney of rats", Mol Cell Biochem, 181(1-2):77-85.

Rajashree and Puvanakrishnan (Jul. 1999) "Dexamethasone induced alterations in the levels of proteases involved in blood pressure homeostasis and blood coagulation in rats", Mol Cell Biochem, 197(1-2):203-8.

Rajashree and Puvanakrishnan (Nov. 2000) "Alterations in collagen metabolism in heart and kidney on dexamethasone administration in rats", Indian J Exp Biol, 38(11):1117-23.

Ramesh et al. (Apr. 1995) "In vitro studies on a novel micelle-forming peptide with anticoagulant activity", Int J Pept Protein Res.,45(4):386-90.

Ramesh et al., (1998) "A Novel Surface-active Peptide Derivative Exhibits in vitro Inhibition of Platelet Aggregation", Peptides,19:1695-1702.

Ramesh et al. (Oct. 1998) "Effect of a novel tetrapeptide derivative in a model of isoproterenol induced myocardial necrosis", Mol Cell Biochem, 187(1-2):173-82.

Ranganathan et al., (2000) "Channel forming, self-assembling, bishelical amphiphilic peptides: design, synthesis and crystal structure of Py(Aib$_n$)$_2$, n=2, 3, 4", J Peptide Res, 56:416-426.

Ravichandran and Puvanakrishnan (Jun. 1991) "In vivo labeling studies on the biosynthesis and degradation of collagen in experimental myocardial infarction", Biochem Int, 24(3):405-14.

Ravichandran and Puvanakrishnan, (Oct. 1993) "Collagen levels in isoproterenol induced myocardial infarction in rats", Indian J Exp Bio, 31(10):825-30.

Ravichandran et al. (Oct. 1990) "Alterations in the heart lysosomal stability in isoproterenol induced myocardial infarction in rats", Biochem Int, 22(2):387-96.

Ravichandran et al. (Feb. 1991) "Influence of Isoproterenol-Induced Myocardial Infarction on Certain Glycohydrolases and Cathepsins in Rats", Biochem Med Metab Biol, 45(1):6-15.

Reape et al., (1999) "Chemokines and atherosclerosis", Atherosclerosis, 147:213-225.

Reddy et al., (2004) "Potential Role for Mitogen-Activated Protein Kinase Phosphatase-1 in the Development of Atherosclerotic Lesions in Mouse Models", Arterioscler Thromb Vasc Biol, 24:1676-1681.

Reddy et al., (2001) "Human Paraoxonase-3 is an HDL Associated Enzyme with Biological Activity Similar to Paraoxonase-1 Protein but is not Regulated by Oxidized Lipids", Arterioscler Thromb Vasc Biol, 21:542-547.

Reubsaet et al., (1999) "Qualitative and quantitative aspects of the degradation of several tripeptides derived from the antitumour peptide antagonist [Arg$^6$, D-Trp$^{7,9}$, MePhe$^8$] substance P {6-11} ", J Pharmaceut & Biomed Analysis, 19(3-4):277-284.

Ridker PM, (2002) "On Evolutionary Biology, Inflammation, Infection, and the Causes of Atherosclerosis", Circulation, 105:2-4.

Roher et al., (1993) "β-Amyloid-(1-42) is a major component of cerebrovascular amyloid deposits: Implications for the pathology of Alzheimer disease", PNAS, USA, 90:10836-10840.

Román et al., (2002) "Subcortical ischaemic vascular dementia", Lancet Neurol., 1:426-436.

Rong et al., (2001) "Elevating High-Density Lipoprotein Cholesterol in Apolipoprotein E-Deficient Mice Remodels Advanced Atherosclerotic Lesions by Decreasing Macrophage and Increasing Smooth Muscle Cell Content", Circulation, 104:2447-2452.

Rubin et al., (1991) "Inhibition of early atherogenesis in transgenic mice by human apolipoprotein A1", Nature, 353:265-267.

Sabbatini et al., (2001) "Microanatomical changes of intracerebral arteries in spontaneously hypertensive rats: a model of cerebrovascular disease of the elderly", Mech. Ageing & Dev., 122: 1257-1268.

Sankaranarayanan et al., (Dec. 1987) "Affinity purification of hexosaminidases", J Biochem Biophys Methods, 15(3-4):207-14.

Sattler et al., (1993) "Greater selective uptake by Hep G2 cells of high-density lipoprotein cholesteryl ester hydroperoxides than of unoxidized cholesteryl esters", Biochem J, 294(Pt 3):771-778.

Schönbeck and Libby, (2004) "Inflammation, Immunity, and Hmg-CoA Reductase Inhibitors, Statins as Antiinflammatory Agents?" Circulation 109(Suppl II):II-18-II-26.

Schröder et al., (1969) "Synthesis, Occurrence, and Action of Biologically Active Polypeptides", The Peptides, vol. II, p. 26 (and relevant passage translated to English).

Segrest et al., (1974) "A Molecular Theory of Lipid-Protein Interaction in the Plasma Lipoproteins." FEBS Lett, 38(3):247-253.

Segrest et al., (1990) "Amphipathic Helix Motif: Classes and Properties", Proteins: Structure, Function and Genetics, 8:103-117.

Segrest et al., (1992) "The Amphipathic Helix in the Exchangeable Apolipoproteins: A Review of Secondary Structure and Function", J Lipid Research 33:141-166.

Segrest et al., (1994) "Amphipathic α Helix: A Multifunctional Structural Motif in Plasma Apolipoproteins", Adv Prot Chem, 45:303-369.

Segrest et al., (2000) "Structure and function of apolipoprotein A-I and high-density lipoprotein", Current Opin Lipidol, 11:105-115.

Senior, Kathryn (Sep. 25, 1999) "New options developed for needle-free drug delivery", (Statistical Data Included), Lancet, 2 pages http://www.findarticles.com/cf 0/m0833/9184_354/55914723/print.jhtml on Jan. 28, 2001.

Shah et al., (1998) "Effects of Recombinant Apolipoprotein A-I$_{Milano}$ on Aortic Atherosclerosis in Apolipoprotein E-Deficient Mice", Circulation, 97(8):780-785.

Shah et al., (2001) " High-Dose Recombinant Apolipoprotein A-I $_{Milano}$ Mobilizes Tissue Cholesterol and Rapidly Reduces Plaque Lipid and Macrophage Content in Apolipoprotein E-Deficient Mice: Potential Implications for Acute Plaque Stabilization", Circulation, 103:3047-3050.

Shih et al., (2000) "Combined Serum Paraoxonase/Apolipoprotein E Knockout Mice Exhibit Increased Lipoprotein Oxidation and Atherosclerosis", J Biol Chem, 275(23):17527-17535.

Shih et al., (1999) "Minimally modified low-density lipoprotein induces monocyte adhesion to endothelial connecting segment-1 by activating β1 integrin", J Clin Invest, 103(5):613-625.

Shishehbor et al., (2003) "Association of Nitrotyrosine Levels with Cardiovascular Disease and Modulation by Statin Therapy", JAMA, 289(13):1675-1680.

Silkensen et al., (1999) "Identification of clusterin sequences mediating renal tubular cell interactions", J. Peptide Res.,54:449-547.

Singh et al., (2000) "Innate Defences Against Viraemia", Rev Med Virol, 10:395-403.

Sonntag et al. (1997) "Decreases in Cerebral Microvasculature with Age Are Associated with the Decline in Growth Hormone and Insulin-Like Growth Factor 1*", Endocrinology 138(8):3515-3520.

Sorescu et al., (2001) "NAD(P)H oxidases and their relevance to atherosclerosis", Trends Cardiovas Med, 11(3-4):124-131.

Spieker et al., (2002) "High-Density Lipoprotein Restores Endothelial Function in Hypercholesterolemic Men", Circulation, 105:1399-1402.

Sprecher et al., (1993) "The Low HDL Cholesterol/ High Triglyceride Trait", Arterioscler Thromb, 13:495-504.

Springer TA, (1990) "Adhesion receptors of the immune system", Nature, 346:425-434.

Srinivas et al., (1990) "Antiviral Effects of Apolipoprotein A-I and Its Synthetic Amphipathic Peptide Analogs", Virology, 176:48-57.

Stannard et al., (2001) "Inability of plasma high-density lipoproteins to inhibit cell adhesion molecule expression in human coronary artery endothelial cells", Atherosclerosis, 154:31-38.

Starlix MC-Amino Acid Fact Sheet (2002) 4 pages http://starlix.com/media_center/content/pp./amino.htm on Dec. 10, 2002.

Su and Amidon, (1995) "Investigation into the intestinal metabolism of [D-Ala$^1$] peptide T amide: implication for oral drug delivery", Biochim et Biophys, 1245: 62-68.

Sugatani et al., (1996) "High-density lipoprotein inhibits the synthesis of platelet-activating factor in human vascular endothelial cells", *J Lipid Mediators Cell Signal*, 13:73-88.

Sumitra et al. (Aug. 2001) "Experimental myocardial necrosis in rats: Role of arjunolic acid on platelet aggregation, coagulation and antioxidant status", *Mol and Cell Biochem*, 224:135-142.

Suresh (Oct. 1992) "Alterations in human gingival glycosaminoglycan pattern in inflammation and in phenytoin induced overgrowth", *Mol Cell Biochem*, 115(2):149-154.

Tan et al., (1997) "A novel, highly efficient peptide-HLA class I binding assay using unfolded heavy chain molecules; identification of HIV-1 derived peptides that bind to HLA-A* 0201 and HLA-A* 0301", *J Immunol Meth*, 205:201-209.

The Merck Index (1996) *An Encyclopedia of Chemicals, Drugs, and Biological*, pp. 1121-1128.

The Wall Street Journal (Jan. 13, 2000) "Emisphere technologies develops oral Heparin".

Thomas, Eric C. (1999) "Brain macrophages: on the role of pericytes and perivascular cells", *Brain Res Rev*, 31:42-57.

Tian et al. (2002) "Structure-affinity relationships in the gp41 ELDKWA epitope for the HIV-1 neutralizing monoclonal antibody $2F_5$: effects of side-chain and backbone modifications and conformational constraints", *J. Peptide Res*. 59:264-276.

Toledo et al. (2004) "Functional independence of a peptide with the sequence of human apolipoprotein A-I central region", *Archives of Biochemistry and Biophysics*, 428(2):188-197.

Toyoda et al. (1997) "Effect of Aging on Regulation of Brain Stem Circulation During Hypotension", *J. Cerebral Blood Flow & Metab.*, 17(6): 680-685.

Tsai et al., (1998) "D-Serine Added to Antipsychotics for the Treatment of Schizophrenia", *Biol. Psychiatry*, 44:1081-1089.

Tsao et al., (2001) "Hibernation-induction peptide and cell death: [D-Ala$^2$, D-Leu$^5$] enkephalin blocks Bax-related apoptotic processes", *European Journal of Pharmacology* 428:149-151.

Tsimikas et al., (2001) "Measuring Circulating Oxidized Low-Density Lipoprotein to Evaluate Coronary Risk", *Circulation* 103:1930-1932.

Tward et al., (2002) "Decreased Atherosclerotic Lesion Formation in Human Serum Paraoxonase Transgenic Mice", *Circulation* 106:484-490.

Van Lenten et al., (1995) "Anti-inflammatory HDL Becomes Pro-inflammatory during the Acute Phase Response. Loss of Protective Effect of HDL against LDL Oxidation in Aortic Wall Cell Cocultures", *J Clin Invest*, 96:2758-2767.

Van Lenten et al., (2002) "Influenza Infection Promotes Macrophage Traffic into Arteries of Mice that is Prevented by D-4F, an Apolipoprotein A-I Mimetic Peptide", *Circulation*, 106:1127-1132.

Van Lenten et al., (2001) "High-Density Lipoprotein Loses its Anti-Inflammatory Properties During Acute Influenza A Infection", *Circulation* 103:2283-2288.

Van Lenten et al., (Sep. 2001) "Acute Influenza A Infection Promotes Increased Macrophage Infiltration into the Artery Wall that is Prevented by Apolipoprotein A-I", *Supplement to Circulation*, 104(12):11-97, 470, Abstract.

Venkatachalapathi et al., (1993) "Effect of End Group Blockage on the. Properties of a Class A Amphipathic Helical Peptide", *Proteins: Structure, Function, and Genetics*, 15:349-359.

Venkatesan et al. (Dec. 31, 1993) "Angiotensin I converting enzyme activity in adriamycin induced nephrosis in rats", *Toxicology*, 85(2-3):137-48.

Venugopal et al., (2002) "Demonstration That C-Reactive Protein Decreases eNOS Expression and Bioactivity in Human Aortic Endothelial Cells", *Circulation*,106:1439-1441.

Vinters et al. (1996) "Brain Parenchymal and Microvascular Amyloid in Alzheimer's Disease", *Brain Pathol*, 6(2):179-195.

Vinters et al. (1998) "Secondary microvascular degeneration in amyloid angiopathy of patients with hereditary cerebral hemorrhage with amyloidosis, Dutch type (HCHWA-D)", *Acta Neuropathol*, 95:235-244.

Vishwanath et al. (Oct. 1997) "Fate of *Mycobacterium tuberculosis* inside rat peritoneal macrophages in vitro", *Mol Cell Biochem*, 175(1-2):169-75.

Vovenko, Eugene (1999) "Distribution of oxygen tension on the surface of arterioles, capillaries and venules of brain cortex and in tissue in normoxia; an experimental study on rats", *Eur J Physiol*, 437:617-623.

Walpola et al., (1995) "Expression of ICAM-1 and VCAM-1 and Monocyte Adherence in Arteries Exposed to Altered Shear Stress", *Arterioscler Thromb Vasc Biol*, 15:2-10.

Watson et al., (1995) "Protective Effect of High Density Lipoprotein Associated Paraoxonase Inhibition of the Biological Activity of Minimally Oxidized Low Density Lipoprotein", *J Clin Invest*, 96:2882-2891.

Watson et al., (1995) "Effect of Platelet Activating Factor-Acetylhydrolase on the Formation and Action of Minimally Oxidized Low Density Lipoprotein", *J Clin Invest*, 95:774-782.

Wei et al. (1998) "Antioxidants Inhibit ATP-Sensitive Potassium Channels in Cerebral Arterioles", *Stroke*, 29:817-823.

Wilson et al., (1988) "High Density Lipoprotein Cholesterol and Mortality: The Framingham Heart Study", *Arteriosclerosis*, 8:737-741.

Wool et al. (2008) "Apolipoprotein A-1 mimetic peptide helix number and helix linker influence potentially anti-atherogenic properties", *Journal of Lipid Research*, 49:1268-1283.

Wool et al. (2009) "An apoA-I mimetic peptide containing a proline residue has greater in vivo HDL binding and anti-inflammatory ability than the 4F peptide", *Journal of Lipid Research*, vol. 1 [downloaded from www.jlr.org at UCLA Biomedical Lib/Serials on May 12, 2009] 43 pages.

Wu et al. (1992) "Inhibition Effects of KRDS, a Peptide Derived from Lactotransferrin, on Platelet Function and Arterial Thrombus Formation in Dogs", *Haemostasis*, 22:1-6.

Xia et al., (1999) "High Density Lipoproteins (HDL) Interrupt the Sphingosine Kinase Signaling Pathway. A Possible Mechanism for Protection Against Atherosclerosis by HDL", *J Biol Chem*, 274:33143-33147.

Yakubu et al. (1997) "Role of lysophosphatidic acid in endothlin-1- and hematomainduced alteration of cerebral microcirculation", *Am. J. Physiol.*, 273(2 pt 2): R703-9.

Yamashita et al., (2000) "Molecular mechanisms, lipoprotein abnormalities and atherogenicity of hyperalphalipoproteinemia", *Atherosclerosis*, 152:271-285.

Yan et al., (2004) "PLTP deficiency improves the anti-inflammatory properties of HDL and reduces the ability of LDL to induce monocyte chemotactic activity", *J Lipid Res*, 45:1852-1858.

Yancey et al., (1995) "Efflux of Cellular Cholesterol and Phospholipid to Lipid-Free Apolipoproteins and Class A Amphipathic Peptides", *Biochemistry*, 34:7955-7965.

Yip K-P et al., (1997) "An Arg-Gly-Asp peptide stimulates constriction in rat afferent arteriole", *Am J Physiol Renal Physiol*, 273:768-776.

Yui et al., (1998) "Serum Prostacyclin Stabilizing Factor Is Identical to Apolipoprotein A-I (Apo A-I). A novel function of Apo A-I", *J. Clin. Invest*, 82:803-807.

Zeiher et al., (1994) "Atherosclerosis/Coronary Heart Disease: Coronary Atherosclerotic Wall Thickening and Vascular Reactivity in Humans Elevated High-Density Lipoprotein Levels Ameliorate Abnormal Vasoconstriction in Early Atherosclerosis", *Circulation*, 89(6):2525-2532.

Zhang and Olsson (1997) "The angiopathy of subcortical arteriosclerotic encephalopathy (Binswanger's disease): immunohistochemical studies using markers for components of extracellular matrix, smooth muscle actin and endothelial cells", *Acta Neuropathol*, 93:219-224.

Zhang et al., (2002) "Myeloperoxidase Functions as a Major Enzymatic Catalyst for Initiation of Lipid Peroxidation at Sites of Inflammation", *J Biol Chem*, 277(48):46116-46122.

Zhang et al., (2002) "Lack of inhibitory effect of HDL on TNFα-induced adhesion molecule expression in human aortic endothelial cells", *Atherosclerosis*, 165:241-249.

Zhao et al., (2002) "Selective Interleukin-12 Synthesis Defect in 12/15-Lipoxygenase-deficient Macrophages Associated with Reduced Atherosclerosis in a Mouse Model of Familial Hypercholesterolemia", *J Biol Chem*, 277(38):35350-35356.

Chinese Office Action (Notification of Reexamination) dated Mar. 20, 2012 issued in CN 200610100669.3.

European Office Action dated Feb. 9, 2012 issued in EP 10 00 2402.5-2401.
Brazilian Written Opinion dated Apr. 12, 2012 issued in BR 0517148-2.
Canadian Office Action dated Jul. 16, 2012 issued in CA 2,595,067.
European Extended Search Report dated Aug. 8, 2012 issued in EP 05 853 364.7.
Japanese Office Action dated Apr. 2, 2012 issued in JP 2007-544634.
Mexican Office Action dated Feb. 23, 2012 issued in MX/a/2007/006750.
Mexican Second Office Action dated Jun. 14, 2012 issued in MX/a/2007/006750.
Philippines Office Action dated Jul. 4, 2012 issued in PH 1-2007-501171.
Vietnamese Office Action dated Dec. 30, 2011 issued in VN 1-2007-01344.
Chinese Second Office Action dated Dec. 16, 2011 issued in CN200680023011.5.
Eurasian Opinion as to patentability dated Feb. 27, 2012 issued in EA 200900786/28.
Egyptian Office Action dated Dec. 7, 2011 issued in EG 1169/2007.
European Examination Report dated Jun. 4, 2012 issued in EP 06 750 791.3-2403.
Japanese Office Action dated Dec. 14, 2011 issued in JP 2008-508931.
Japanese Final Rejection dated Jul. 13, 2012 issued in JP 2008-508931.
Philippines Office Action dated Jul. 19, 2012 issued in PH 1-2007-502394.
US Notice of Allowance and Examiner-Initiated Interview Summary dated Apr. 12, 2012 issued in U.S. Appl. No. 12/478,593.

Buga et al. (Oct. 1, 2005) "D-4F, an apoA-1 mimetic peptide, reduces brain arteriolar wall thickening in LDL receptor null mice fed a western diet and improves spatial memory", *Circulation, Lippincott Williams & Wilkins*, US, 112(17)Suppl. S:U234 , 2 pp.
Buga et al., (2006) "D-4F decreases brain arteriole inflammation and improves cognitive performance in LDL receptor-null mice on a Western diet", *Journal of Lipid Research*, [Downloaded from www.jir.org at UCLA Biomedical Lib/Serials on Oct. 3, 2006] 47:2148-2160.
Gupta et al., (Jun. 14, 2005) "Apolipoprotein E mimetic Peptide dramatically lowers plasma cholesterol and restores endothelial function in watanabe heritable hyperlipidemic rabbits", *Circulation, Lippincott Williams & Wilkins*, US, 111(23):3112-3118.
Ou et al., (Mar. 1, 2003) "4F, an apo A-I mimetic peptide preserves acetylcholine-induced vasodilation of carotid arterioles in sickle cell disease mice", *FASEB Journal, Fed. Of American Soc. for Experimental Biology*, US, 17(4-5):258.12, 1 page.
Ou et al., (Mar. 1, 2003) "An apo A-I mimetic peptide preserves vasodilation in hypercholesterolemic mice", *FASEB Journal, Fed. Of American Soc. for Experimental Biology*, US, 17(4-5):341.15, 1 page.
Ou et al., (May 13, 2003) "L-4F, an apolipoprotein A-I mimetic, dramatically improves vasodilation in hypercholesterolemia and sickle cell disease", *Circulation, Lippincott Williams & Wilkins*, US, 107(18):2337-2341.
Ou et al., (Oct. 28, 2003) "D-4F restores endothelium- and eNOS-dependent vasodilation and reduces vessel wall thickness in hypercholesterolemia", *Circulation, Lippincott Williams & Wilkins*, US, 108(17)Suppl:IV-281, 2 pp.
Ou et al., (Oct. 19, 2004) "L-4F dramatically improve endothelium-dependent vasodilation under lipoprotein oxidative stress", Zhonghua Zhongliu Zazhi-*Chinese Journal of Oncology*, Zhonghua Yixuehui, Beijing, CN, 32(10)911-914.

```
                         SEQUENCE LISTING

<160> NUMBER OF SEQ ID NOS: 106

<210> SEQ ID NO 1
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 1

Asp Trp Leu Lys Ala Phe Tyr Asp Lys Val Ala Glu Lys Leu Lys Glu
1               5                   10                  15

Ala Phe

<210> SEQ ID NO 2
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 2

Asp Trp Leu Lys Ala Phe Tyr Asp Lys Val Ala Glu Lys Leu Lys Glu
1               5                   10                  15

Ala Phe

<210> SEQ ID NO 3
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 3

Asp Trp Phe Lys Ala Phe Tyr Asp Lys Val Ala Glu Lys Leu Lys Glu
1               5                   10                  15

Ala Phe

<210> SEQ ID NO 4
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 4
```

Asp Trp Leu Lys Ala Phe Tyr Asp Lys Val Ala Glu Lys Phe Lys Glu
1               5                   10                  15

Ala Phe

<210> SEQ ID NO 5
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 5

Asp Trp Phe Lys Ala Phe Tyr Asp Lys Val Ala Glu Lys Phe Lys Glu
1               5                   10                  15

Ala Phe

<210> SEQ ID NO 6
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 6

Asp Trp Leu Lys Ala Phe Tyr Asp Lys Val Phe Glu Lys Phe Lys Glu
1               5                   10                  15

Phe Phe

<210> SEQ ID NO 7
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 7

Asp Trp Leu Lys Ala Phe Tyr Asp Lys Phe Phe Glu Lys Phe Lys Glu
1               5                   10                  15

Phe Phe

<210> SEQ ID NO 8
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 8

Asp Trp Phe Lys Ala Phe Tyr Asp Lys Phe Phe Glu Lys Phe Lys Glu
1               5                   10                  15

Phe Phe

<210> SEQ ID NO 9
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 9

Asp Trp Leu Lys Ala Phe Tyr Asp Lys Val Ala Glu Lys Leu Lys Glu
1               5                   10                  15

Phe Phe

<210> SEQ ID NO 10
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 10

Asp Trp Leu Lys Ala Phe Tyr Asp Lys Val Phe Glu Lys Phe Lys Glu
1               5                   10                  15

Ala Phe

<210> SEQ ID NO 11
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 11

Asp Trp Leu Lys Ala Phe Tyr Asp Lys Val Phe Glu Lys Leu Lys Glu
1               5                   10                  15

Phe Phe

<210> SEQ ID NO 12
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 12

Asp Trp Leu Lys Ala Phe Tyr Asp Lys Val Ala Glu Lys Phe Lys Glu
1               5                   10                  15

Phe Phe

<210> SEQ ID NO 13
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 13

Asp Trp Leu Lys Ala Phe Tyr Asp Lys Val Phe Glu Lys Phe Lys Glu
1               5                   10                  15

Phe Phe

<210> SEQ ID NO 14
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 14

Glu Trp Leu Lys Leu Phe Tyr Glu Lys Val Leu Glu Lys Phe Lys Glu
1               5                   10                  15

Ala Phe

<210> SEQ ID NO 15
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 15

Glu Trp Leu Lys Ala Phe Tyr Asp Lys Val Ala Glu Lys Phe Lys Glu
1               5                   10                  15

Ala Phe

<210> SEQ ID NO 16
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 16

Glu Trp Leu Lys Ala Phe Tyr Asp Lys Val Ala Glu Lys Leu Lys Glu
1               5                   10                  15

Phe Phe

<210> SEQ ID NO 17
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 17

Glu Trp Leu Lys Ala Phe Tyr Asp Lys Val Phe Glu Lys Phe Lys Glu
1               5                   10                  15

Ala Phe

<210> SEQ ID NO 18
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 18

Glu Trp Leu Lys Ala Phe Tyr Asp Lys Val Phe Glu Lys Leu Lys Glu
1               5                   10                  15

Phe Phe

<210> SEQ ID NO 19
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 19

```
Glu Trp Leu Lys Ala Phe Tyr Asp Lys Val Ala Glu Lys Phe Lys Glu
1               5                   10                  15

Phe Phe

<210> SEQ ID NO 20
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 20

Glu Trp Leu Lys Ala Phe Tyr Asp Lys Val Phe Glu Lys Phe Lys Glu
1               5                   10                  15

Phe Phe

<210> SEQ ID NO 21
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 21

Ala Phe Tyr Asp Lys Val Ala Glu Lys Leu Lys Glu Ala Phe
1               5                   10

<210> SEQ ID NO 22
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 22

Ala Phe Tyr Asp Lys Val Ala Glu Lys Phe Lys Glu Ala Phe
1               5                   10

<210> SEQ ID NO 23
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 23

Ala Phe Tyr Asp Lys Val Ala Glu Lys Phe Lys Glu Ala Phe
1               5                   10

<210> SEQ ID NO 24
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 24

Ala Phe Tyr Asp Lys Phe Phe Glu Lys Phe Lys Glu Phe Phe
1               5                   10

<210> SEQ ID NO 25
<211> LENGTH: 14
```

```
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 25

Ala Phe Tyr Asp Lys Phe Phe Glu Lys Phe Lys Glu Phe Phe
1               5                   10

<210> SEQ ID NO 26
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 26

Ala Phe Tyr Asp Lys Val Ala Glu Lys Phe Lys Glu Ala Phe
1               5                   10

<210> SEQ ID NO 27
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 27

Ala Phe Tyr Asp Lys Val Ala Glu Lys Leu Lys Glu Phe Phe
1               5                   10

<210> SEQ ID NO 28
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 28

Ala Phe Tyr Asp Lys Val Phe Glu Lys Phe Lys Glu Ala Phe
1               5                   10

<210> SEQ ID NO 29
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 29

Ala Phe Tyr Asp Lys Val Phe Glu Lys Leu Lys Glu Phe Phe
1               5                   10

<210> SEQ ID NO 30
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 30

Ala Phe Tyr Asp Lys Val Ala Glu Lys Phe Lys Glu Phe Phe
1               5                   10
```

<210> SEQ ID NO 31
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 31

Lys Ala Phe Tyr Asp Lys Val Phe Glu Lys Phe Lys Glu Phe
1               5                   10

<210> SEQ ID NO 32
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 32

Leu Phe Tyr Glu Lys Val Leu Glu Lys Phe Lys Glu Ala Phe
1               5                   10

<210> SEQ ID NO 33
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 33

Ala Phe Tyr Asp Lys Val Ala Glu Lys Phe Lys Glu Ala Phe
1               5                   10

<210> SEQ ID NO 34
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 34

Ala Phe Tyr Asp Lys Val Ala Glu Lys Leu Lys Glu Phe Phe
1               5                   10

<210> SEQ ID NO 35
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 35

Ala Phe Tyr Asp Lys Val Phe Glu Lys Phe Lys Glu Ala Phe
1               5                   10

<210> SEQ ID NO 36
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

```
<400> SEQUENCE: 36

Ala Phe Tyr Asp Lys Val Phe Glu Lys Leu Lys Glu Phe Phe
1               5                   10

<210> SEQ ID NO 37
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 37

Ala Phe Tyr Asp Lys Val Ala Glu Lys Phe Lys Glu Phe Phe
1               5                   10

<210> SEQ ID NO 38
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 38

Ala Phe Tyr Asp Lys Val Phe Glu Lys Phe Lys Glu Phe Phe
1               5                   10

<210> SEQ ID NO 39
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 39

Asp Trp Leu Lys Ala Leu Tyr Asp Lys Val Ala Glu Lys Leu Lys Glu
1               5                   10                  15

Ala Leu

<210> SEQ ID NO 40
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 40

Asp Trp Phe Lys Ala Phe Tyr Glu Lys Val Ala Glu Lys Leu Lys Glu
1               5                   10                  15

Phe Phe

<210> SEQ ID NO 41
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 41

Asp Trp Phe Lys Ala Phe Tyr Glu Lys Phe Phe Glu Lys Phe Lys Glu
1               5                   10                  15

Phe Phe
```

```
<210> SEQ ID NO 42
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 42

Glu Trp Leu Lys Ala Leu Tyr Glu Lys Val Ala Glu Lys Leu Lys Glu
1               5                   10                  15

Ala Leu

<210> SEQ ID NO 43
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 43

Glu Trp Leu Lys Ala Phe Tyr Glu Lys Val Ala Glu Lys Leu Lys Glu
1               5                   10                  15

Ala Phe

<210> SEQ ID NO 44
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 44

Glu Trp Phe Lys Ala Phe Tyr Glu Lys Val Ala Glu Lys Leu Lys Glu
1               5                   10                  15

Phe Phe

<210> SEQ ID NO 45
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 45

Glu Trp Leu Lys Ala Phe Tyr Glu Lys Val Phe Glu Lys Phe Lys Glu
1               5                   10                  15

Phe Phe

<210> SEQ ID NO 46
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 46

Glu Trp Leu Lys Ala Phe Tyr Glu Lys Phe Phe Glu Lys Phe Lys Glu
1               5                   10                  15

Phe Phe
```

<210> SEQ ID NO 47
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 47

Glu Trp Phe Lys Ala Phe Tyr Glu Lys Phe Phe Glu Lys Phe Lys Glu
1               5                   10                  15

Phe Phe

<210> SEQ ID NO 48
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 48

Asp Phe Leu Lys Ala Trp Tyr Asp Lys Val Ala Glu Lys Leu Lys Glu
1               5                   10                  15

Ala Trp

<210> SEQ ID NO 49
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 49

Glu Phe Leu Lys Ala Trp Tyr Glu Lys Val Ala Glu Lys Leu Lys Glu
1               5                   10                  15

Ala Trp

<210> SEQ ID NO 50
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 50

Asp Phe Trp Lys Ala Trp Tyr Asp Lys Val Ala Glu Lys Leu Lys Glu
1               5                   10                  15

Trp Trp

<210> SEQ ID NO 51
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 51

Glu Phe Trp Lys Ala Trp Tyr Glu Lys Val Ala Glu Lys Leu Lys Glu
1               5                   10                  15

Trp Trp

```
<210> SEQ ID NO 52
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 52

Asp Lys Leu Lys Ala Phe Tyr Asp Lys Val Phe Glu Trp Ala Lys Glu
1               5                   10                  15

Ala Phe

<210> SEQ ID NO 53
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 53

Asp Lys Trp Lys Ala Val Tyr Asp Lys Phe Ala Glu Ala Phe Lys Glu
1               5                   10                  15

Phe Leu

<210> SEQ ID NO 54
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 54

Glu Lys Leu Lys Ala Phe Tyr Glu Lys Val Phe Glu Trp Ala Lys Glu
1               5                   10                  15

Ala Phe

<210> SEQ ID NO 55
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 55

Glu Lys Trp Lys Ala Val Tyr Glu Lys Phe Ala Glu Ala Phe Lys Glu
1               5                   10                  15

Phe Leu

<210> SEQ ID NO 56
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 56

Asp Trp Leu Lys Ala Phe Val Asp Lys Phe Ala Glu Lys Phe Lys Glu
1               5                   10                  15

Ala Tyr
```

```
<210> SEQ ID NO 57
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 57

Glu Lys Trp Lys Ala Val Tyr Glu Lys Phe Ala Glu Ala Phe Lys Glu
1               5                   10                  15

Phe Leu

<210> SEQ ID NO 58
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 58

Asp Trp Leu Lys Ala Phe Val Tyr Asp Lys Val Phe Lys Leu Lys Glu
1               5                   10                  15

Phe Phe

<210> SEQ ID NO 59
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 59

Glu Trp Leu Lys Ala Phe Val Tyr Glu Lys Val Phe Lys Leu Lys Glu
1               5                   10                  15

Phe Phe

<210> SEQ ID NO 60
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 60

Asp Trp Leu Arg Ala Phe Tyr Asp Lys Val Ala Glu Lys Leu Lys Glu
1               5                   10                  15

Ala Phe

<210> SEQ ID NO 61
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 61

Glu Trp Leu Arg Ala Phe Tyr Glu Lys Val Ala Glu Lys Leu Lys Glu
1               5                   10                  15

Ala Phe
```

<210> SEQ ID NO 62
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 62

Asp Trp Leu Lys Ala Phe Tyr Asp Arg Val Ala Glu Lys Leu Lys Glu
1               5                   10                  15

Ala Phe

<210> SEQ ID NO 63
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 63

Glu Trp Leu Lys Ala Phe Tyr Glu Arg Val Ala Glu Lys Leu Lys Glu
1               5                   10                  15

Ala Phe

<210> SEQ ID NO 64
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 64

Asp Trp Leu Lys Ala Phe Tyr Asp Lys Val Ala Glu Arg Leu Lys Glu
1               5                   10                  15

Ala Phe

<210> SEQ ID NO 65
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 65

Glu Trp Leu Lys Ala Phe Tyr Glu Lys Val Ala Glu Arg Leu Lys Glu
1               5                   10                  15

Ala Phe

<210> SEQ ID NO 66
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 66

Asp Trp Leu Lys Ala Phe Tyr Asp Lys Val Ala Glu Lys Leu Arg Glu
1               5                   10                  15

Ala Phe

-continued

<210> SEQ ID NO 67
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 67

Glu Trp Leu Lys Ala Phe Tyr Glu Lys Val Ala Glu Lys Leu Arg Glu
1               5                   10                  15
Ala Phe

<210> SEQ ID NO 68
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 68

Asp Trp Leu Lys Ala Phe Tyr Asp Arg Val Ala Glu Arg Leu Lys Glu
1               5                   10                  15
Ala Phe

<210> SEQ ID NO 69
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 69

Glu Trp Leu Lys Ala Phe Tyr Glu Arg Val Ala Glu Arg Leu Lys Glu
1               5                   10                  15
Ala Phe

<210> SEQ ID NO 70
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 70

Asp Trp Leu Arg Ala Phe Tyr Asp Lys Val Ala Glu Lys Leu Arg Glu
1               5                   10                  15
Ala Phe

<210> SEQ ID NO 71
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 71

Glu Trp Leu Arg Ala Phe Tyr Glu Lys Val Ala Glu Lys Leu Arg Glu
1               5                   10                  15
Ala Phe

```
<210> SEQ ID NO 72
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 72

Asp Trp Leu Arg Ala Phe Tyr Asp Arg Val Ala Glu Lys Leu Lys Glu
1               5                   10                  15

Ala Phe

<210> SEQ ID NO 73
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 73

Glu Trp Leu Arg Ala Phe Tyr Glu Arg Val Ala Glu Lys Leu Lys Glu
1               5                   10                  15

Ala Phe

<210> SEQ ID NO 74
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 74

Asp Trp Leu Lys Ala Phe Tyr Asp Lys Val Ala Glu Arg Leu Arg Glu
1               5                   10                  15

Ala Phe

<210> SEQ ID NO 75
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 75

Glu Trp Leu Lys Ala Phe Tyr Glu Lys Val Ala Glu Arg Leu Arg Glu
1               5                   10                  15

Ala Phe

<210> SEQ ID NO 76
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 76

Asp Trp Leu Arg Ala Phe Tyr Asp Lys Val Ala Glu Arg Leu Lys Glu
1               5                   10                  15

Ala Phe
```

```
<210> SEQ ID NO 77
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 77

Glu Trp Leu Arg Ala Phe Tyr Glu Lys Val Ala Glu Arg Leu Lys Glu
1               5                   10                  15

Ala Phe

<210> SEQ ID NO 78
<211> LENGTH: 37
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 78

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Leu Lys Glu Ala Phe
        35

<210> SEQ ID NO 79
<211> LENGTH: 37
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 79

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
                20                  25                  30

Leu Lys Glu Phe Phe
        35

<210> SEQ ID NO 80
<211> LENGTH: 37
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 80

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
                20                  25                  30

Leu Lys Glu Ala Phe
        35

<210> SEQ ID NO 81
<211> LENGTH: 37
```

```
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 81

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
            20                  25                  30

Leu Lys Glu Ala Phe
        35

<210> SEQ ID NO 82
<211> LENGTH: 37
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 82

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
            20                  25                  30

Phe Lys Glu Phe Leu
        35

<210> SEQ ID NO 83
<211> LENGTH: 37
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 83

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
        35

<210> SEQ ID NO 84
<211> LENGTH: 37
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 84

Asp Trp Leu Lys Ala Phe Val Tyr Asp Lys Val Phe Lys Leu Lys Glu
1               5                   10                  15

Phe Phe Pro Asp Trp Leu Lys Ala Phe Val Tyr Asp Lys Val Phe Lys
            20                  25                  30

Leu Lys Glu Phe Phe
        35

<210> SEQ ID NO 85
<211> LENGTH: 37
```

```
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 85

Asp Trp Leu Lys Ala Phe Tyr Asp Lys Phe Ala Glu Lys Phe Lys Glu
1               5                   10                  15

Phe Phe Pro Asp Trp Leu Lys Ala Phe Tyr Asp Lys Phe Ala Glu Lys
            20                  25                  30

Phe Lys Glu Phe Phe
        35

<210> SEQ ID NO 86
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 86

Glu Trp Phe Lys Ala Phe Tyr Glu Lys Val Ala Glu Lys Phe Lys Glu
1               5                   10                  15

Ala Phe

<210> SEQ ID NO 87
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 87

Asp Trp Phe Lys Ala Phe Tyr Asp Lys Val Ala Glu Lys Phe
1               5                   10

<210> SEQ ID NO 88
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 88

Phe Lys Ala Phe Tyr Asp Lys Val Ala Glu Lys Phe Lys Glu
1               5                   10

<210> SEQ ID NO 89
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 89

Phe Lys Ala Phe Tyr Glu Lys Val Ala Glu Lys Phe Lys Glu
1               5                   10

<210> SEQ ID NO 90
<211> LENGTH: 17
<212> TYPE: PRT
<213> ORGANISM: Artificial
```

```
<220> FEATURE:
<223> OTHER INFORMATION: Synthetic peptide can be "D" or "L" form,
      protected or unprotected.

<400> SEQUENCE: 90

Asn Met Ala Phe Lys Ala Phe Tyr Asp Lys Val Ala Glu Lys Phe Lys
1               5                   10                  15

Glu

<210> SEQ ID NO 91
<211> LENGTH: 17
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 91

Asn Met Ala Phe Lys Ala Phe Tyr Glu Lys Val Ala Glu Lys Phe Lys
1               5                   10                  15

Glu

<210> SEQ ID NO 92
<211> LENGTH: 21
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 92

Asn Met Ala Asp Trp Phe Lys Ala Phe Tyr Asp Lys Val Ala Glu Lys
1               5                   10                  15

Phe Lys Glu Ala Phe
            20

<210> SEQ ID NO 93
<211> LENGTH: 21
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 93

Asn Met Ala Glu Trp Phe Lys Ala Phe Tyr Glu Lys Val Ala Glu Lys
1               5                   10                  15

Phe Lys Glu Ala Phe
            20

<210> SEQ ID NO 94
<211> LENGTH: 17
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 94

Asn Met Ala Ala Phe Tyr Asp Lys Val Ala Glu Lys Phe Lys Glu Ala
1               5                   10                  15

Phe

<210> SEQ ID NO 95
<211> LENGTH: 17
```

```
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 95

Asn Met Ala Asp Trp Phe Lys Ala Phe Tyr Asp Lys Val Ala Glu Lys
1               5                   10                  15
Phe

<210> SEQ ID NO 96
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 96

Asp Trp Leu Lys Ala Phe Tyr Asp Lys Val Phe Glu Lys Phe Lys Glu
1               5                   10                  15
Phe Phe

<210> SEQ ID NO 97
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 97

Glu Trp Leu Lys Ala Phe Tyr Glu Lys Val Phe Glu Lys Phe Lys Glu
1               5                   10                  15
Phe Phe

<210> SEQ ID NO 98
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 98

Ala Phe Tyr Asp Lys Val Phe Glu Lys Phe Lys Glu Phe Phe
1               5                   10

<210> SEQ ID NO 99
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 99

Ala Phe Tyr Glu Lys Val Phe Glu Lys Phe Lys Glu Phe Phe
1               5                   10

<210> SEQ ID NO 100
<211> LENGTH: 14
<212> TYPE: PRT
<213> ORGANISM: Artificial
<220> FEATURE:
<223> OTHER INFORMATION: Synthetic peptide can be "D" or "L" form,
```

-continued

```
      protected or unprotected.

<400> SEQUENCE: 100

Asp Trp Leu Lys Ala Phe Tyr Asp Lys Val Phe Glu Lys Phe
1               5                   10

<210> SEQ ID NO 101
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 101

Glu Trp Leu Lys Ala Phe Tyr Glu Lys Val Phe Glu Lys Phe
1               5                   10

<210> SEQ ID NO 102
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 102

Leu Lys Ala Phe Tyr Asp Lys Val Phe Glu Lys Phe Lys Glu
1               5                   10

<210> SEQ ID NO 103
<211> LENGTH: 14
<212> TYPE: PRT
<213> ORGANISM: Artificial
<220> FEATURE:
<223> OTHER INFORMATION: Synthetic peptide can be "D" or "L" form,
      protected or unprotected.

<400> SEQUENCE: 103

Leu Lys Ala Phe Tyr Glu Lys Val Phe Glu Lys Phe Lys Glu
1               5                   10

<210> SEQ ID NO 104
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.
<220> FEATURE:
<221> NAME/KEY: misc_feature
<222> LOCATION: (1)..(1)
<223> OTHER INFORMATION: Xaa is aspartic or glutamic acid or homologues
      or analogues thereof
<220> FEATURE:
<221> NAME/KEY: misc_feature
<222> LOCATION: (2)..(3)
<223> OTHER INFORMATION: Xaa is tryptophan, phenylalanine, alanine,
      leucine, tyrosine, isoleucine, valine or a-naphthylalanine, or
      homologues or analogues thereof
<220> FEATURE:
<221> NAME/KEY: misc_feature
<222> LOCATION: (4)..(4)
<223> OTHER INFORMATION: Xaa is lysine or arginine
<220> FEATURE:
<221> NAME/KEY: misc_feature
<222> LOCATION: (5)..(5)
<223> OTHER INFORMATION: Xaa is serine, threonine, alanine, glycine,
      histidine, or homologues or analogues thereof.
<220> FEATURE:
<221> NAME/KEY: misc_feature
<222> LOCATION: (6)..(7)
```

```
<223> OTHER INFORMATION: Xaa is tryptophan, phenylalanine, alanine,
      leucine, tyrosine, isoleucine, valine or a-naphthylalanine, or
      homologues or analogues thereof
<220> FEATURE:
<221> NAME/KEY: misc_feature
<222> LOCATION: (8)..(8)
<223> OTHER INFORMATION: Xaa is aspartic or glutamic acid or homologues
      or analogues thereof
<220> FEATURE:
<221> NAME/KEY: misc_feature
<222> LOCATION: (9)..(9)
<223> OTHER INFORMATION: Xaa is lysine or arginine
<220> FEATURE:
<221> NAME/KEY: misc_feature
<222> LOCATION: (10)..(11)
<223> OTHER INFORMATION: Xaa is tryptophan, phenylalanine, alanine,
      leucine, tyrosine, isoleucine, valine or a-naphthylalanine, or
      homologues or analogues thereof
<220> FEATURE:
<221> NAME/KEY: misc_feature
<222> LOCATION: (12)..(12)
<223> OTHER INFORMATION: Xaa is aspartic or glutamic acid or homologues
      or analogues thereof
<220> FEATURE:
<221> NAME/KEY: misc_feature
<222> LOCATION: (13)..(13)
<223> OTHER INFORMATION: Xaa is lysine or arginine
<220> FEATURE:
<221> NAME/KEY: misc_feature
<222> LOCATION: (14)..(14)
<223> OTHER INFORMATION: Xaa is tryptophan, phenylalanine, alanine,
      leucine, tyrosine, isoleucine, valine or a-naphthylalanine, or
      homologues or analogues thereof
<220> FEATURE:
<221> NAME/KEY: misc_feature
<222> LOCATION: (15)..(15)
<223> OTHER INFORMATION: Xaa is lysine or arginine
<220> FEATURE:
<221> NAME/KEY: misc_feature
<222> LOCATION: (16)..(16)
<223> OTHER INFORMATION: Xaa is aspartic or glutamic acid or homologues
      or analogues thereof
<220> FEATURE:
<221> NAME/KEY: misc_feature
<222> LOCATION: (17)..(18)
<223> OTHER INFORMATION: Xaa is tryptophan, phenylalanine, alanine,
      leucine, tyrosine, isoleucine, valine or a-naphthylalanine, or
      homologues or analogues thereof

<400> SEQUENCE: 104

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 105
<211> LENGTH: 18
<212> TYPE: PRT
<213> ORGANISM: Artificial
<220> FEATURE:
<223> OTHER INFORMATION: Synthetic peptide can be "D" or "L" form,
      protected or unprotected.
<220> FEATURE:
<221> NAME/KEY: misc_feature
<222> LOCATION: (1)..(1)
<223> OTHER INFORMATION: Xaa is Pro (P), Ala (A), Gly (G), Asn (N),
      Gln (Q) or D-Pro (p);
<220> FEATURE:
<221> NAME/KEY: misc_feature
<222> LOCATION: (2)..(2)
<223> OTHER INFORMATION: Xaa is an aliphatic amino acid
<220> FEATURE:
<221> NAME/KEY: misc_feature
<222> LOCATION: (3)..(3)
<223> OTHER INFORMATION: Xaa is an aliphatic amino acid
<220> FEATURE:
<221> NAME/KEY: misc_feature
<222> LOCATION: (4)..(4)
```

```
<223> OTHER INFORMATION: Xaa is an acidic amino acid
<220> FEATURE:
<221> NAME/KEY: misc_feature
<222> LOCATION: (5)..(6)
<223> OTHER INFORMATION: Xaa is Leu (L) or Phe (F);
<220> FEATURE:
<221> NAME/KEY: misc_feature
<222> LOCATION: (7)..(7)
<223> OTHER INFORMATION: Xaa is a basic amino acid
<220> FEATURE:
<221> NAME/KEY: misc_feature
<222> LOCATION: (8)..(8)
<223> OTHER INFORMATION: Xaa is an acidic amino acid
<220> FEATURE:
<221> NAME/KEY: misc_feature
<222> LOCATION: (9)..(9)
<223> OTHER INFORMATION: Xaa is Leu (L) or Trp (W);
<220> FEATURE:
<221> NAME/KEY: misc_feature
<222> LOCATION: (9)..(10)
<223> OTHER INFORMATION: Xaa is Leu (L) or Trp (W);
<220> FEATURE:
<221> NAME/KEY: misc_feature
<222> LOCATION: (11)..(11)
<223> OTHER INFORMATION: Xaa is an acidic amino acid or Asn (N)
<220> FEATURE:
<221> NAME/KEY: misc_feature
<222> LOCATION: (12)..(12)
<223> OTHER INFORMATION: Xaa is an acidic amino acid
<220> FEATURE:
<221> NAME/KEY: misc_feature
<222> LOCATION: (13)..(13)
<223> OTHER INFORMATION: Xaa is Leu (L), Trp (W) or Phe (F);
<220> FEATURE:
<221> NAME/KEY: misc_feature
<222> LOCATION: (14)..(14)
<223> OTHER INFORMATION: Xaa is a basic amino acid or Leu (L);
<220> FEATURE:
<221> NAME/KEY: misc_feature
<222> LOCATION: (15)..(15)
<223> OTHER INFORMATION: Xaa is Gln (Q) or Asn (N);
<220> FEATURE:
<221> NAME/KEY: misc_feature
<222> LOCATION: (16)..(16)
<223> OTHER INFORMATION: Xaa is a basic amino acid;
<220> FEATURE:
<221> NAME/KEY: misc_feature
<222> LOCATION: (18)..(18)
<223> OTHER INFORMATION: Xaa is a basic amino acid;

<400> SEQUENCE: 105

Xaa Xaa Leu Xaa Xaa Xaa Xaa Xaa Xaa Xaa Xaa Xaa Xaa Xaa Xaa Xaa
1               5                   10                  15

Leu Xaa

<210> SEQ ID NO 106
<211> LENGTH: 7
<212> TYPE: PRT
<213> ORGANISM: Artificial
<220> FEATURE:
<223> OTHER INFORMATION: Peptide linker.

<400> SEQUENCE: 106

Gly Gly Gly Gly Ser Ser Ser
1               5
```

ORALLY ADMINISTERED PEPTIDES SYNERGIZE STATIN ACTIVITY

CROSS-REFERENCE TO RELATED APPLICATIONS

This application is a continuation of U.S. Ser. No. 11/830,687, filed on Jul. 30, 2007, which is a continuation of U.S. Ser. No. 11/431,412, filed on May 9, 2006, now U.S. Pat. No. 7,531,514, which is a continuation of U.S. Ser. No. 10/423,830, filed on Apr. 25, 2003, now U.S. Pat. No. 7,199,102, which is a continuation-in-part of Ser. No. 10/273,386, filed on Oct. 16, 2002, now U.S. Pat. No. 7,166,578, which is a continuation-in-part of Ser. No. 10/187,215, filed on Jun. 28, 2002, now U.S. Pat. No. 7,144,862, which is a continuation-in-part of Ser. No. 09/896,841, filed on Jun. 29, 2001, now U.S. Pat. No. 6,933,279, which is a continuation-in-part of U.S. Ser. No. 09/645,454, filed on Aug. 24, 2000, now U.S. Pat. No. 6,664,230, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant Nos. HL30568 and HL34343 awarded by the United States Public Health Service and National Heart, Lung, and Blood Institute. The Government of the United States of America has certain rights in this invention.

FIELD OF THE INVENTION

This invention relates to the field of atherosclerosis. In particular, this invention pertains to the identification of a class of peptides that are orally administrable and that ameliorate one or more symptoms of atherosclerosis.

BACKGROUND OF THE INVENTION

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of rate-limiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include the amount and type of fat (saturated and polyunsaturated fatty acids), the amount of cholesterol, the amount and type of fiber, and perhaps the amounts of vitamins such as vitamin C and D and minerals such as calcium.

Epidemiological studies show an inverse correlation of high density lipoprotein (HDL) and apolipoprotein (apo) A-I levels with the occurrence of atherosclerotic events (Wilson et al. (1988) *Arteriosclerosis* 8: 737-741). Injection of HDL into rabbits fed an atherogenic diet has been shown to inhibit atherosclerotic lesion formation (Badimon et al. (1990) *J. Clin. Invest.* 85: 1234-1241).

Human apo A-I has been a subject of intense study because of its anti-atherogenic properties. Exchangeable apolipoproteins, including apo A-I, possess lipid-associating domains (Brouillette and Anantharamaiah (1995) *Biochim. Biophys. Acta* 1256:103-129; Segrest et al. (1974) *FEBS Lett.* 38: 247-253). Apo A-I has been postulated to possess eight tandem repeating 22mer sequences, most of which have the potential to form class A amphipathic helical structures (Segrest et al. (1974) *FEBS Lett.* 38: 247-253). Characteristics of the class A amphipathic helix include the presence of positively charged residues at the polar-nonpolar interface and negatively charged residues at the center of the polar face (Segrest et al. (1974) *FEBS Lett.* 38: 247-253; Segrest et al. (1990) *Proteins: Structure, Function, and Genetics* 8: 103-117). Apo A-I has been shown to strongly associate with phospholipids to form complexes and to promote cholesterol efflux from cholesterol-enriched cells. The delivery and maintenance of serum levels of apo A-I to effectively mitigate one or more symptoms of atherosclerosis has heretofore proven elusive.

SUMMARY OF THE INVENTION

This invention provides novel peptides administration of which mitigates one or more symptoms of atherosclerosis. In particular, it was a discovery of this invention that peptides comprising a class A amphipathic helix when formulated with "D" amino acid residue(s) and/or having protected amino and carboxyl termini can be orally administered to an organism, are readily taken up and delivered to the serum, and are effective to mitigate one or more symptoms of atherosclerosis. In certain embodiments, the peptides can be formulated with all "L" amino acid residues and are still effective, particular when administered by routes other than oral administration.

The peptides of this invention are typically effective to stimulate the formation and cycling of pre-beta high density lipoprotein-like particles and/or to promote lipid transport and detoxification.

The peptides described herein are also effective for preventing the onset or inhibiting or eliminating one or more symptoms of osteoporosis.

It was also a surprising discovery that the peptides can be used to enhance (e.g. synergistically enhance) the activity of statins thereby permitting the effective use of statins at lower dosages and/or cause the statins to be significantly more anti-inflammatory at any given dose.

Thus, in one embodiment, this invention provides a peptide that ameliorates one or more symptoms of atherosclerosis where the peptide comprises a peptide or a concatamer of a peptide that ranges in length from about 10 to about 30 amino acids, that comprises at least one class A amphipathic helix; that protects a phospholipid against oxidation by an oxidizing agent; and that is not the D-18A peptide and/or is not a peptide disclosed in WO 97/36927, and/or U.S. Pat. No. 6,037,323, and/or U.S. Pat. No. 4,643,988. In certain embodiments, the peptide is at least 10 amino acids in length. In certain embodiments, the peptide is about 40 or fewer amino acids in length. In certain embodiments, the peptide comprises all "L" amino acids while in certain other embodiments, the peptide comprises at least one "D" amino acid residue. In certain embodiments, all enantiomeric amino acids comprising the peptide are "D" amino acids. The peptide can, optionally, further comprises a protecting group (e.g. a protecting group coupled to the amino and/or to the carboxyl terminus). Suitable protecting groups include, but are not limited to, acetyl (Ac), amide, a 3 to 20 carbon alkyl group, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-Butyl (tBu), and trifluoroacetyl (TFA). In certain embodiments, the peptide further comprises a first protecting group coupled to the amino terminus and a second protecting group coupled to the carboxyl terminus. The peptide can be mixed with a with a pharmacologically acceptable excipient (e.g., a pharmacologically acceptable excipient suitable for oral administration to a mammal). In certain embodiments, the comprises a sequence selected from the group consisting of D-W-L-K-A-F-Y-D-K-V-A-E-K-L-K-E-A-F- (SEQ ID NO:2), D-W-F-K-A-F-Y-D-K-V-A-E-K-L-K-E-A-F- (SEQ ID NO:3), D-W-L-K-A-F-Y-D-K-V-A-E-K-F-K-E-A-F- (SEQ ID NO:4), D-W-F-K-A-F-Y-D-K-V-A-E-K-F-K-E-A-F- (SEQ ID NO:5), D-W-L-K-A-F-Y-D-K-V-F-E-K-F-K-E-F- (SEQ ID NO:6), D-W-L-K-A-F-Y-D-K-F-F-E-K-F-K-E-F-F- (SEQ ID NO:7), D-W-F-K-A-F-Y-D-K-F-F-E-K-F-K-E-F-F- (SEQ ID NO:8), D-W-L-K-A-F-Y-D-K-V-A-E-K-L-K-E-F-F- (SEQ ID NO:9), D-W-L-K-A-F-Y-D-K-V-F-E-K-F-K-E-A-F- (SEQ ID NO:10), D-W-L-K-A-F-Y-D-K-V-F-E-K-L-K-E-F-F- (SEQ ID NO:11), D-W-L-K-A-F-Y-D-K-V-A-E-K-F-K-E-F-F- (SEQ ID NO:12), D-W-L-K-A-F-Y-D-K-V-F-E-K-F-K-E-F-F- (SEQ ID NO:13), E-W-L-K-L-F-Y-E-K-V-L-E-K-F-K-E-A-F- (SEQ ID NO:14), E-W-L-K-A-F-Y-D-K-V-A-E-K-F-K-E-A-F- (SEQ ID NO:15), E-W-L-K-A-F-Y-D-K-V-A-E-K-L-K-E-F-F- (SEQ ID NO:16), E-W-L-K-A-F-Y-D-K-V-F-E-K-F-K-E-A-F- (SEQ ID NO:17), E-W-L-K-A-F-Y-D-K-V-F-E-K-L-K-E-F-F- (SEQ ID NO:18), E-W-L-K-A-F-Y-D-K-V-A-E-K-F-K-E-F-F- (SEQ ID NO:19), E-W-L-K-A-F-Y-D-K-V-F-E-K-F-K-E-F-F- (SEQ ID NO:20), A-F-Y-D-K-V-A-E-K-L-K-E-A-F- (SEQ ID NO:21), A-F-Y-D-K-V-A-E-K-F-K-E-A-F- (SEQ ID NO:22), A-F-Y-D-K-V-A-E-K-F-K-E-A-F- (SEQ ID NO:23), A-F-Y-D-K-F-F-E-K-F-K-E-F-F- (SEQ ID NO:24), A-F-Y-D-K-F-F-E-K-F-K-E-F-F- (SEQ ID NO:25), A-F-Y-D-K-V-A-E-K-F-K-E-A-F- (SEQ ID NO:26), A-F-Y-D-K-V-F-E-K-L-K-E-F-F- (SEQ ID NO:27), A-F-Y-D-K-V-F-E-K-F-K-E-A-F- (SEQ ID NO:28), A-F-Y-D-K-V-F-E-K-L-K-E-F-F- (SEQ ID NO:29), A-F-Y-D-K-V-A-E-K-F-K-E-F-F- (SEQ ID NO:30), K-A-F-Y-D-K-V-F-E-K-F-K-E-F- (SEQ ID NO:31), L-F-Y-E-K-V-L-E-K-F-K-E-A-F- (SEQ ID NO:32), A-F-Y-D-K-V-A-E-K-F-K-E-A-F- (SEQ ID NO:33), A-F-Y-D-K-V-A-E-K-L-K-E-F-F- (SEQ ID NO:34), A-F-Y-D-K-V-F-E-K-F-K-E-A-F- (SEQ ID NO:35), A-F-Y-D-K-V-F-E-K-L-K-E-F-F- (SEQ ID NO:36), A-F-Y-D-K-V-A-E-K-F-K-E-F-F- (SEQ ID NO:37), A-F-Y-D-K-V-F-E-K-F-K-E-F-F- (SEQ ID NO:38), D-W-L-K-A-L-Y-D-K-V-A-E-K-L-K-E-A-L- (SEQ ID NO:39), D-W-F-K-A-F-Y-E-K-V-A-E-K-L-K-E-F-F- (SEQ ID NO:40), D-W-F-K-A-F-Y-E-K-F-F-E-K-F-K-E-F-F- (SEQ ID NO:41), E-W-L-K-A-L-Y-E-K-V-A-E-K-L-K-E-A-L- (SEQ ID NO:42), E-W-L-K-A-F-Y-E-K-V-A-E-K-L-K-E-A-F- (SEQ ID NO:43), E-W-F-K-A-F-Y-E-K-V-A-E-K-L-K-E-F-F- (SEQ ID NO:44), E-W-L-K-A-F-Y-E-K-V-F-E-K-F-K-E-F-F- (SEQ ID NO:45), E-W-L-K-A-F-Y-E-K-F-F-E-K-F-K-E-F-F- (SEQ ID NO:46), E-W-F-K-A-F-Y-E-K-F-F-E-K-F-K-E-F-F- (SEQ ID NO:47), D-F-L-K-A-W-Y-D-K-V-A-E-K-L-K-E-A-W- (SEQ ID NO:48), E-F-L-K-A-W-Y-E-K-V-A-E-K-L-K-E-A-W- (SEQ ID NO:49), D-F-W-K-A-W-Y-D-K-V-A-E-K-L-K-E-W-W- (SEQ ID NO:50), E-F-W-K-A-W-Y-E-K-V-A-E-K-L-K-E-W-W- (SEQ ID NO:51), D-K-L-K-A-F-Y-D-K-V-F-E-W-A-K-E-A-F- (SEQ ID NO:52), D-K-W-K-A-V-Y-D-K-F-A-E-A-F-K-E-F-L- (SEQ ID NO:53), E-K-L-K-A-F-Y-E-K-V-F-E-W-A-K-E-A-F- (SEQ ID NO:54), E-K-W-K-A-V-Y-E-K-F-A-E-A-F-K-E-F-L- (SEQ ID NO:55), D-W-L-K-A-F-V-D-K-F-A-E-K-F-K-E-A-Y- (SEQ ID NO:56), E-K-W-K-A-V-Y-E-K-F-A-E-A-F-K-E-F-L- (SEQ ID NO:57), D-W-L-K-A-F-V-Y-D-K-V-F-K-L-K-E-F-F- (SEQ ID NO:58), E-W-L-K-A-F-V-Y-E-K-V-F-K-L-K-E-F-F- (SEQ ID NO:59), D-W-L-R-A-F-Y-D-K-V-A-E-K-L-K-E-A-F- (SEQ ID NO:60), E-W-L-R-A-F-Y-E-K-V-A-E-K-L-K-E-A-F- (SEQ ID NO:61), D-W-L-K-A-F-Y-D-R-V-A-E-K-L-K-E-A-F- (SEQ ID NO:62), E-W-L-K-A-F-Y-E-R-V-A-E-K-L-K-E-A-F- (SEQ ID NO:63), D-W-L-K-A-F-Y-D-K-V-A-E-R-L-K-E-A-F- (SEQ ID NO:64), E-W-L-K-A-F-Y-E-K-V-A-E-R-L-K-E-A-F- (SEQ ID NO:65), D-W-L-K-A-F-Y-D-K-V-A-E-K-L-R-E-A-F- (SEQ ID NO:66), E-W-L-K-A-F-Y-E-K-V-A-E-K-L-R-E-A-F- (SEQ ID NO:67), D-W-L-K-A-F-Y-D-R-V-A-E-R-L-K-E-A-F- (SEQ ID NO:68), E-W-L-K-A-F-Y-E-R-V-A-E-R-L-K-E-A-F- (SEQ ID NO:69), D-W-L-R-A-F-Y-D-K-V-A-E-K-L-R-E-A-F- (SEQ ID NO:70), E-W-L-R-A-F-Y-E-K-V-A-E-K-L-R-E-A-F- (SEQ ID NO:71), D-W-L-R-A-F-Y-D-R-V-A-E-K-L-K-E-A-F- (SEQ ID NO:72), E-W-L-R-A-F-Y-E-R-V-A-E-K-L-K-E-A-F- (SEQ ID NO:73), D-W-L-K-A-F-Y-D-K-V-A-E-R-L-R-E-A-F- (SEQ ID NO:74), E-W-L-K-A-F-Y-E-K-V-A-E-R-L-R-E-A-F- (SEQ ID NO:75), D-W-L-R-A-F-Y-D-K-V-A-E-R-L-K-E-A-F- (SEQ ID NO:76), E-W-L-R-A-F-Y-E-K-V-A-E-R-L-K-E-A-F- (SEQ ID NO:77), D-W-L-K-A-F-Y-D-K-V-A-E-K-L-K-E-A-F-P-D-W-L-K-A-F-Y-D-K-V-A-E-K-L-K-E-A-F (SEQ ID NO:78), D-W-L-K-A-F-Y-D-K-V-A-E-K-L-K-E-F-F-P-D-W-L-K-A-F-Y-D-K-V-A-E-K-L-K-E-F-F (SEQ ID NO:79), D-W-F-K-A-F-Y-D-K-V-A-E-K-L-K-E-A-F-P-D-W-F-K-A-F-Y-D-K-V-A-E-K-L-K-E-A-F (SEQ ID NO:80), D-K-L-K-A-F-Y-D-K-V-F-E-W-A-K-E-A-F-P-D-K-L-K-A-F-Y-D-K-V-F-E-W-L-K-E-A-F (SEQ ID NO:81), D-K-W-K-A-V-Y-D-K-F-A-E-A-F-K-E-F-L-P-D-K-W-K-A-V-Y-D-K-F-A-E-A-F-K-E-F-L (SEQ ID NO:82), D-W-F-K-A-F-Y-D-K-V-A-E-K-F-K-E-A-F-P-D-W-F-K-A-F-Y-D-K-V-A-E-K-F-K-E-A-F (SEQ ID NO:83), D-W-L-K-A-F-V-Y-D-K-V-F-K-L-K-E-F-F-P-D-W-L-K-A-F-V-Y-D-K-V-F-K-L-K-E-F-F (SEQ ID NO:84), D-W-L-K-A-F-Y-D-K-F-A-E-K-F-K-E-F-F-P-D-W-L-K-A-F-Y-D-K-F-A-E-K-F-K-E-F-F (SEQ ID NO:85), E-W-F-K-A-F-Y-E-K-V-A-E-K-F-K-E-A-F (SEQ ID NO:86), D-W-F-K-A-F-Y-D-K-V-A-E-K-F (SEQ ID NO:87), F-K-A-F-Y-D-K-V-A-E-K-F-K-E (SEQ ID NO:88), F-K-A-F-Y-E-K-V-A-E-K-F-K-E (SEQ ID NO:89), F-K-A-F-Y-D-K-V-A-E-K-F-K-E (SEQ ID NO:90), F-K-A-F-Y-E-K-V-A-E-K-F-K-E (SEQ ID NO:91), D-W-F-K-A-F-Y-D-K-V-A-E-K-F-K-E-A-F (SEQ ID NO:92), E-W-F-K-A-F-Y-E-K-V-A-E-K-F-K-E-A-F (SEQ ID NO:93), A-F-Y-D-K-V-A-E-K-F-K-E-A-F (SEQ ID NO:94), D-W-F-K-A-F-Y-D-K-V-A-E-K-F (SEQ ID NO:95), D-W-L-K-A-F-Y-D-K-V-F-E-K-F-K-E-F-F (SEQ ID NO:96), E-W-L-K-A-F-Y-E-K-V-F-E-K-F-K-E-F-F (SEQ ID NO:97), A-F-Y-D-K-V-F-E-K-F-K-E-F-F (SEQ ID NO:98), A-F-Y-E-K-V-F-E-K-F-K-E-F-F (SEQ ID NO:99), D-W-L-K-A-F-Y-D-K-V-F-E-K-F (SEQ ID NO:100), E-W-L-K-A-F-Y-E-K-V-F-E-K-F (SEQ ID NO:101), L-K-A-F-Y-D-K-V-F-E-K-F-K-E (SEQ ID NO:102), and L-K-A-F-Y-E-K-V-F-E-K-F-K-E (SEQ ID NO:103). In certain embodiments, the foregoing peptides comprise all "L" amino acids. In certain embodiments, the foregoing peptides comprise at least one "D" amino acid, more typically a plurality of "D" amino acids. In certain embodiments, at least half of the enantiomeric amino acids are "D" amino acids, and in certain embodiments, all of the enantiomeric amino acids are "D" amino acids.

In certain embodiments, the peptide further comprises a protecting group coupled to the amino and/or to the carboxyl terminus. Thus, for example, the peptide can comprise a protecting group coupled to the amino terminal where the amino terminal protecting group is a protecting group selected from the group consisting of a benzoyl group, an acetyl, a propionyl, a carbobenzoxy, a propyl, a butyl, a pentyl, a hexyl, an N-methyl anthranilyl, and a 3 to 20 carbon alkyl and/or the peptide comprises a protecting group coupled to the carboxyl terminal where the carboxyl terminal protecting group is an amide.

The oxidizing agent can be an agent such as hydrogen peroxide, 13(S)-HPODE, 15(S)-HPETE, HPODE, HPETE, HODE, HETE, and the like. In certain embodiments, the phospholipid is selected from the group consisting of 1-palmitoyl-2-arachidonoyl-sn-glycero-3-phosphorylcholine (PAPC), 1-stearoyl-2-arachidonoyl-sn-glycero-3-phosphorylcholine (SAPC)), 1-stearoyl-2-arachidonyl-sn-glycero-3-phosphorylethanolamine (SAPE).

The peptide can be provided as a pharmaceutical formulation, e.g. combined with a pharmaceutically acceptable excipient. The peptide can be provided as a unit dosage formulation. In certain embodiments, the peptide can be formulated as a time release formulation (e.g., in a "time-release" matrix, microencapsulated, etc.).

In another embodiment, this invention provides a method of enhancing the activity of a statin in a mammal. The method typically involves coadministering with the statin an effective amount of one or more of the peptides described herein. In certain embodiments the statin include, but is not limited to one or more statins selected from the group consisting of cerivastatin, atorvastatin, simvastatin, pravastatin, fluvastatin, lovastatin, rosuvastatin, and pitavastatin. The peptide can be administered before, simultaneously with, or after administration of the statin(s). In certain embodiments, the peptide and/or the statin are administered as a unit dosage formulation. The administration of the peptide and/or the statin can be by a route including, but not limited to of oral administration, nasal administration, rectal administration, intraperitoneal injection, intravascular injection, subcutaneous injection, transcutaneous administration, intramuscular injection, and the like. In certain embodiments, the is a mammal diagnosed as having one or more symptoms of atherosclerosis. In certain embodiments, the mammal is a mammal diagnosed as at risk for stroke or atherosclerosis. The mammal can be a human or a non-human mammal.

In still another embodiment, this invention provides a method of mitigating one or more symptoms associated with atherosclerosis in a mammal. The method typically involves administering to the mammal an effective amount of one or more statins (e.g., cerivastatin, atorvastatin, simvastatin, pravastatin, fluvastatin, lovastatin, rosuvastatin, pitavastatin, etc.); and an effective amount of one or more peptides described herein, where the effective amount of the statin is lower than the effective amount of a statin administered without the peptide. In certain embodiments, the effective amount of the peptide is lower than the effective amount of the peptide administered without the statin. The peptide(s) can be administered before, simultaneously with, or after the statin(s). The peptide and/or the statin can be administered as a unit dosage formulation. The peptide(s) and/or statin(s) can be administered by a route including, but not limited to oral administration, nasal administration, rectal administration, intraperitoneal injection, intravascular injection, subcutaneous injection, transcutaneous administration, inhalation administration, and intramuscular injection. In certain embodiments, the mammal is a human or non-human mammal diagnosed as having one or more symptoms of atherosclerosis and/or at risk for stroke and/or atherosclerosis.

This invention also provides a pharmaceutical formulation. The formulation typically comprises a pharmaceutically acceptable excipient and one or more of the peptides described herein. Another pharmaceutical formulation typically comprises one or more statins (e.g., cerivastatin, atorvastatin, simvastatin, pravastatin, fluvastatin, lovastatin, rosuvastatin, pitavastatin, etc.) and one or more peptides as described herein. In certain embodiments, the peptide and/or said statin are present in an effective dose. In certain embodiments, the effective amount of the statin is lower than the effective amount of the statin administered without the peptide(s) and/or the effective amount of the peptide(s) is lower than the effective amount of the peptide(s) administered without the statin(s). In various embodiments, the statin(s) and/or the peptide(s) are in a time release formulation (e.g. a time release matrix, a microencapsulated formulation, and the like). The pharmaceutical formulation can be a unit dosage formulation, e.g., for oral administration. In certain embodiments, the formulation is formulated for administration by a route selected from the group consisting of oral administration, nasal administration, rectal administration, intraperitoneal injection, intravascular injection, subcutaneous injection, transcutaneous administration, inhalation administration, and intramuscular injection. The formulation can, optionally, further comprises one or more phospholipids (e.g. a phospholipid as described in U.S. Ser. No. 09/994,227).

In another embodiment, this invention provides a method of reducing or inhibiting one or more symptoms of osteoporosis in a mammal. The method typically involves administering to the mammal one or more peptides as described herein, where the peptide is administered in a concentration sufficient to reduce or eliminate one or more symptoms of osteoporosis. In certain embodiments, the peptide is administered in a concentration sufficient to reduce or eliminate decalcification of a bone. In certain embodiments, the peptide is administered in a concentration sufficient to induce recalcification of a bone. The peptide(s) can be mixed with a pharmacologically acceptable excipient, e.g. as described herein.

In certain embodiments, the methods and/or peptides of this invention exclude any one or more peptides disclosed in WO 97/36927, and/or U.S. Pat. No. 6,037,323, and/or U.S. Pat. No. 4,643,988 and/or in Garber et al. (1992) *Arteriosclerosis and Thrombosis,* 12: 886-894. In certain embodiments this invention excludes any one or more peptides disclosed in U.S. Pat. No. 4,643,988 and/or in Garber et al (1992) that were synthesized with all enantiomeric amino acids being L amino acids or synthesized with D amino acids where the peptides possess blocking groups. In certain embodiments, this invention excludes peptides having the formula $A_1$-$B_1$-$B_2$-$C_1$-D-$B_3$-$B_4$-$A_2$-$C_2$-$B_5$-$B_6$-$A_3$-$C_3$-$B_7$-$C_4$-$A_4$-$B_8$-$B_9$ (SEQ ID NO:104) wherein $A_1$, $A_2$, $A_3$ and $A_4$ are independently aspartic acid or glutamic acid, or homologues or analogues thereof; $B_1$, $B_2$, $B_3$, $B_4$, $B_5$, $B_6$, $B_7$, $B_8$ and $B_9$ are independently tryptophan, phenylalanine, alanine, leucine, tyrosine, isoleucine, valine or α-naphthylalanine, or homologues or analogues thereof; $C_1$, $C_2$, $C_3$ and $C_4$ are independently lysine or arginine, and D is serine, threonine, alanine, glycine, histidine, or homologues or analogues thereof; provided that, when $A_1$ and $A_2$ are aspartic acid, $A_3$ and $A_4$ are glutamic acid, $B_2$ and $B_9$ are leucine, $B_3$ and $B_7$ are phenylalanine, $B_4$ is tyrosine, $B_5$ is valine, $B_6$, $B_8$, and D are alanine, and $C_1$, $C_2$, $C_3$ and $C_4$ are lysine, $B_1$ is not tryptophan.

In certain embodiments, this invention excludes any one or more peptides in WO 97/36927 and/or D variants thereof. Particular embodiments exclude one or more of the following: apoprotein A, apoprotein A-1, apoprotein A-2, apoprotein A4, apoprotein B, apoprotein B-48, apoprotein B-100, apoprotein C, apoprotein C-1, apoprotein C-2, apoprotein C-3, apoprotein D, apoprotein E as described in WO 97/36927.

In certain embodiments, also excluded are any one or more peptides disclosed in U.S. Pat. No. 6,037,323 and/or D variants thereof. Particular embodiments exclude apo A-I agonist compounds comprising (i) an 18 to 22-residue peptide or peptide analogue that forms an amphipathic .alpha.-helix in the presence of lipids and that comprises the formula: $Z_1$-$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$Z_2$ (SEQ ID NO:105), where $X_1$ is Pro (P), Ala (A), Gly (G), Asn (N), Gln (Q) or D-Pro (p); $X_2$ is an aliphatic amino acid; $X_3$ is Leu (L); $X_4$ is an acidic amino acid; $X_5$ is Leu (L) or Phe (F); $X_6$ is Leu (L) or Phe (F); $X_7$ is a basic amino acid; $X_8$ is an acidic amino acid; $X_9$ is Leu (L) or Trp (W); $X_{10}$ is Leu (L) or Trp (W); $X_{11}$ is an acidic amino acid or Asn (N); $X_{12}$ is an acidic amino acid; $X_{13}$ is Leu (L), Trp (W) or Phe (F); $X_{14}$ is a basic amino acid or Leu (L); $X_{12}$ is Gln (Q) or Asn (N); $X_{16}$ is a basic amino acid; $X_{17}$ is Leu (L); $X_{18}$ is a basic amino acid; $Z_1$ is $H_2N$— or RC(O)NH—; $Z_2$ is —C(O)NRR, —C(O)OR or —C(O)OH or a salt thereof; each R is independently —H, $(C_1$-$C_6)$alkyl, $(C_1$-$C_6)$alkenyl, $(C_1$-$C_6)$alkynyl, $(C_5$-$C_{20})$aryl, $(C_6$-$C_{26})$alkaryl, 5-20 membered heteroaryl or 6-26 membered alkheteroaryl or a 1 to 4-residue peptide or peptide analogue in which one or more bonds between residues 1-7 are independently a substituted amide, an isostere of an amide or an amide mimetic; and each "-" between residues $X_1$ through $X_{18}$ independently designates an amide linkage, a substituted amide linkage, an isostere of an amide or an amide mimetic; or (ii) an altered form of formula (I) in which at least one of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$ or $X_{18}$ is conservatively substituted with another residue, and/or D variants thereof.

Definitions

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., Segrest et al. (1990) *Proteins: Structure, Function, and Genetics* 8: 103-117).

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like. "Ameliorating one or more symptoms of atherosclerosis" can also refer to improving blood flow to vascular beds affected by atherosclerosis.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art.

The term "protecting group" refers to a chemical group that, when attached to a functional group in an amino acid (e.g. a side chain, an alpha amino group, an alpha carboxyl group, etc.) blocks or masks the properties of that functional group. Preferred amino-terminal protecting groups include, but are not limited to acetyl, or amino groups. Other amino-terminal protecting groups include, but are not limited to alkyl chains as in fatty acids, propionyl, formyl and others. Preferred carboxyl terminal protecting groups include, but are not limited to groups that form amides or esters.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g. hydrogen peroxide, 13-(S)-HPODE, 15-(S)-HPETE, HPODE, HPETE, HODE, HETE, etc.).

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g. apo A-I, paraoxonase, platelet activating factor acetylhydrolase, etc.) that reduce oxidized lipids (e.g. in low density lipoproteins) or that protect oxidized lipids from oxidation by oxidizing agents.

The term "Group II HDL" refers to an HDL that offers reduced activity or no activity in protecting lipids from oxidation or in repairing (e.g. reducing) oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g. apo A-I, paraoxonase, platelet activating factor acetylhydrolase, etc.) that display such activity.

The term "human apo A-I peptide" refers to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g. cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g. at least at the 85%, preferably at least at the 90%, more preferably at least at the 95%, and most preferably at least at the 98% or 99% confidence level). The absence of a detectable change can also refer to assays in which oxidized phospholipid level changes, but not as much as in the absence of the protein(s) described herein or with reference to other positive or negative controls.

The following abbreviations are used herein: PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane E$_2$)-sn-glycero-3-phsophocholine; ChC18:2: cholesteryl linoleate; ChC18:2-OOH: cholesteryl linoleate hydroperoxide; DMPC: 1,2-ditetradecanoyl-rac-glycerol-3-phosphocholine; PON: paraoxonase; HPF: Standardized high power field; PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane E$_2$)-sn-glycero-3-phosphocholine; PON: paraoxonase; BL/6: C57BL/6J; C3H: C3H/HeJ.

The term "conservative substitution" is used in reference to proteins or peptides to reflect amino acid substitutions that do not substantially alter the activity (specificity (e.g. for lipoproteins)) or binding affinity (e.g. for lipids or lipoproteins)) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA*, 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al. (1990) *J. Mol. Biol.* 215: 403-410. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA,* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "D-18A peptide" refers to a peptide having the sequence: D-W-L-K-A-F-Y-D-K-V-A-E-K-L-K-E-A-F (SEQ ID NO: 1) where all of the enantiomeric amino acids are D form amino acids.

The term "coadministering" or "concurrent administration", when used, for example with respect to a peptide of this invention and another active agent (e.g. a statin), refers to administration of the peptide and the active agent such that both can simultaneously achieve a physiological effect. The two agents, however, need not be administered together. In certain embodiments, administration of one agent can precede administration of the other, however, such coadministering typically results in both agents being simultaneously present in the body (e.g. in the plasma) at a significant fraction (e.g. 20% or greater, preferably 30% or 40% or greater, more preferably 50% or 60% or greater, most preferably 70% or 80% or 90% or greater) of their maximum serum concentration for any given dose.

The term "detoxify" when used with respect to lipids, LDL, or HDL refers the removal of some or all oxidizing lipids and/or oxidized lipids. Thus, for example, the uptake of all or some HPODE and/or HPETE (both hydroperoxides on fatty acids) will prevent or reduce entrance of these peroxides into LDLs and thus prevent or reduce LDL oxidation.

The term "pre-beta high density lipoprotein-like particles" typically refers to cholesterol containing particles that also contain apoA-I and which are smaller and relatively lipid-poor compared to the lipid:protein ratio in the majority of HDL particles. When plasma is separated by FPLC, these "pre-beta high density lipoprotein-like particles" are found in the FPLC fractions containing particles smaller than those in the main HDL peak and are located to the right of HDL in an FPLC chromatogram as shown in the accompanying FIGS. 5 and 8.

The phrase "reverse lipid transport and detoxification" refers to the removal of lipids including cholesterol, other sterols including oxidized sterols, phospholipids, oxidizing agents, and oxidized phospholipids from tissues such as arteries and transport out of these peripheral tissues to organs where they can be detoxified and excreted such as excretion by the liver into bile and excretion by the kidneys into urine. Detoxification also refers to preventing the formation and/or destroying oxidized phospholipids as explained herein.

The term "biological sample" as used herein refers to any sample obtained from a living organism or from an organism that has died. Examples of biological samples include body fluids, tissue specimens, cells and cell lines taken from an organism (e.g. a human or non-human mammal).

BRIEF DESCRIPTION OF THE DRAWINGS

FIG. 4A shows a solvent blank, FIG. 4B shows standards for D-4F (top) and D-5F (bottom), and FIG. 4C shows the results of analysis of pooled FPLC fractions 35-37 for D-4F in the top panel with the internal standard D-5F in the bottom panel.

DETAILED DESCRIPTION

Figure 1:
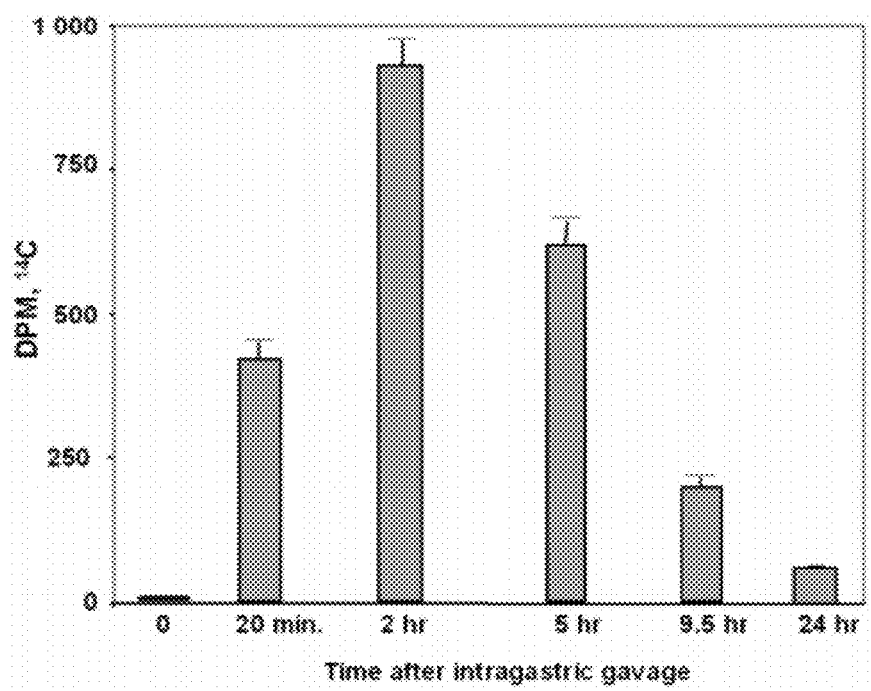
FIG. 1 illustrates the detection of $^{14}$C-D-4F in mouse plasma. 22 μg of $^{14}$C-D-4F, 140,000 DPM in 100 μl of water was administered to 4 month old female apoE null mice by stomach tube. Blood samples were obtained at each time point (n=4 mice per time point) and plasma $^{14}$C-radioactivity determined in 1.0 ml of plasma.

This invention pertains to the discovery that synthetic peptides designed to mimic the class A amphipathic helical motif (Segrest et al. (1990) Proteins: Structure, Function, and Genetics 8: 103-117) are able to associate with phospholipids and exhibit many biological properties similar to human apo-A-I. In particular, it was a discovery of this invention that when such peptides are formulated using D amino acids, the peptides show dramatically elevated serum half-lives and, particularly when the amino and/or carboxy termini are blocked, can even be orally administered.

It was also a surprising discovery that these peptides can stimulate the formation and cycling of pre-beta high density lipoprotein-like particles. In addition, the peptides are capable of enhancing/synergizing the effect of statins allowing statins to be administered as significantly lower dosages or to be significantly more anti-inflammatory at any given dose. It was also discovered that the peptides described herein can inhibit and/or prevent and/or treat one or more symptoms of osteoporosis.

Moreover, it was a surprising discovery of this invention that such D-form peptides retain the biological activity of the corresponding L-form peptide. In vivo animal studies using such D-form peptides showed effective oral delivery, elevated serum half-life, and the ability to mitigate or prevent/inhibit one or more symptoms of atherosclerosis.

I. Stimulating the Formation and Cycling of Pre-Beta High Density Lipoprotein-Like Particles.

Reverse cholesterol transport is considered to be important in preventing the build up of lipids that predisposes to atherosclerosis (Shah et al. (2001) Circulation, 103: 3047-3050.) Many have believed the lipid of consequence is cholesterol. Our laboratory has shown that the key lipids are oxidized phospholipids that initiate the inflammatory response in atherosclerosis (Navab et al. (2001) Arterioscler Thromb Vasc Biol., 21(4): 481-488; Van Lenten et al. (001) Trends Cardiovasc Med, 11: 155-161; Navab M et al. (2001) Circulation, 104: 2386-2387).

This inflammatory response is also likely responsible for plaque erosion or rupture that leads to heart attack and stroke. HDL-cholesterol levels are inversely correlated with risk for heart attack and stroke (Downs et al. (1998) JAMA 279: 1615-1622; Gordon et al. (1977) Am J Med., 62: 707-714; Castelli et al. (1986) JAMA, 256: 2835-2838).

Pre-beta HDL is generally considered to be the most active HDL fraction in promoting reverse cholesterol transport (e.g., picking up cholesterol from peripheral tissues such as arteries and carrying it to the liver for excretion into the bile; see, Fielding and Fielding (2001) Biochim Biophys Acta, 1533(3): 175-189). However, levels of pre-beta HDL can be increased because of a failure of the pre-beta HDL to be cycled into mature alpha-migrating HDL e.g. LCAT deficiency or inhibition (O'Connor et al. (1998) J Lipid Res, 39: 670-678). High levels of pre-beta HDL have been reported in coronary artery disease patients (Miida et al. (1996) Clin Chem., 42: 1992-1995).

Moreover, men have been found to have higher levels of pre-beta HDL than women but the risk of men for coronary heart disease is greater than for women (O'Connor et al. (1998) J Lipid Res., 39: 670-678). Thus, static measurements of pre-beta HDL levels themselves are not necessarily predictive of risk for coronary artery disease. The cycling, however, of cholesterol through pre-beta HDL into mature HDL is universally considered to be protective against atherosclerosis (Fielding and Fielding (2001) Biochim Biophys Acta, 1533 (3): 175-189). Moreover, we have demonstrated that the removal of oxidized lipids from artery wall cells through this pathway protects against LDL oxidation.

As described herein in Example 1, despite relatively low absorption rates when orally administered, the peptides of this invention (e.g. D-4F) were highly active.

In studies of Apo-E null mice orally administered D-4F, we determined that 20 min after absorption from the intestine, D-4F forms small pre-beta HDL-like particles that contain relatively high amounts of apoA-I and paraoxonase. Indeed, estimating the amount of apoA-I in these pre-beta HDL-like particles from Western blots and comparing the amount of apoA-I to the amount of D-4F in these particles (determined by radioactivity or LC-MRM) suggests that as D-4F is absorbed from the intestine, it acts as a catalyst causing the formation of these pre-beta HDL-like particles. This small amount of intestinally derived D-4F appears to recruit amounts of apoA-I, paraoxonase, and cholesterol into these particles that are orders of magnitude more than the amount of D-4F.

Thus, following absorption, D-4F rapidly recruits relatively large amounts of apoA-I and paraoxonase to form pre-beta HDL-like particles which are very likely the most potent particles for both promoting reverse cholesterol transport and for destroying biologically active oxidized lipids. We believe that the formation of these particles and their subsequent rapid incorporation into mature HDL likely explains the dramatic reduction in atherosclerosis that we observed in LDL receptor null mice on a Western diet and in apoE-null mice on a chow diet independent of changes in plasma cholesterol or HDL-cholesterol.

Thus, in one embodiment, this invention provides methods of stimulating the formation and cycling of pre-beta high density lipoprotein-like particles by administration of one or more peptides as described herein. The peptides can thereby promote lipid transport and detoxification.

II. Synergizing the Activity of Statins.

Figure 9:
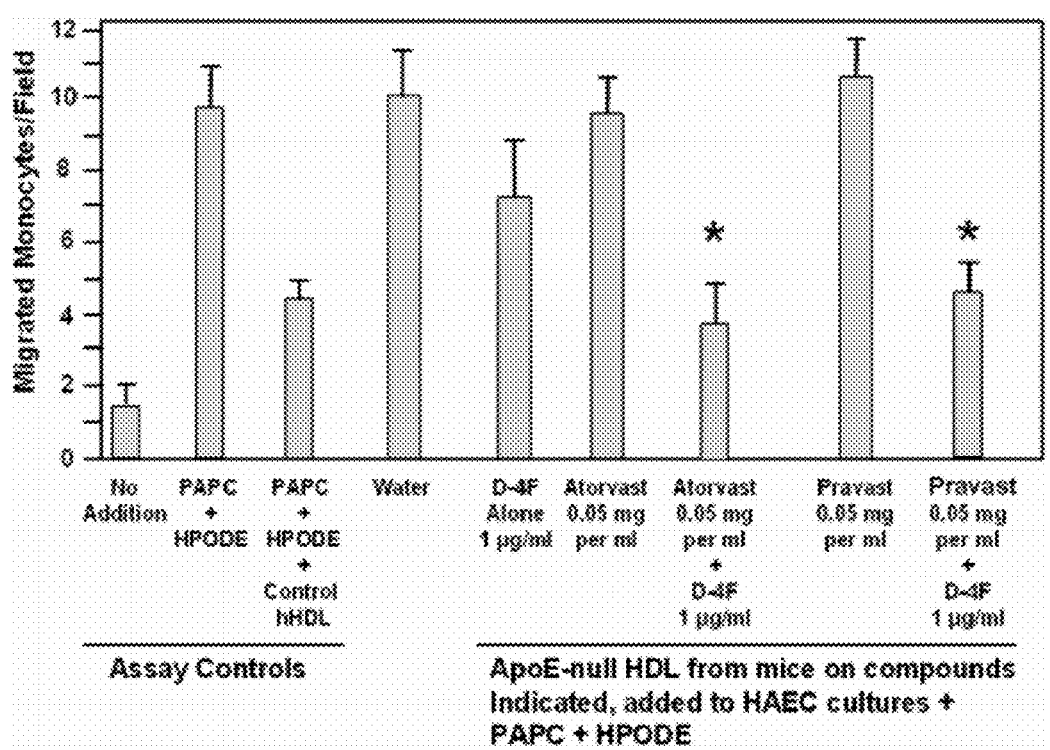
FIG. 9 illustrates the synergy between statins and D-4F in restoring HDL protective capacity. ApoE null female mice three months old on a chow diet were given drinking water alone (Water), or drinking water containing 1 μg/ml of D-4F, or 0.05 mg/ml of Atorvastatin, or 0.05 mg/ml of Pravastatin, or 1 μg/ml of D-4F together with 0.05 mg/ml of Atorvastatin, or 1 μg/ml of D-4F together with 0.05 mg/ml of Pravastatin. After 24 hours the mice were bled and their HDL was tested in a human artery wall coculture model. Twenty μg of 1-palmitoyl-2-arachidonyl-sn-glycero-3-phosphorylcholine (PAPC) was added together with 1 μg/ml of hydroperoxye-icosatetraenoic acid (HPODE) to cocultures of human artery wall cells as described previously (Navab et al. (2001) J Lipid Res., 42: 1308-1317). Human HDL (h, HDL) was added at 350 μg/ml cholesterol or no addition was made to the cocultures (No Addition), or mouse HDL isolated by FPLC from the mice given drinking water alone (Water) or the additions shown on the X-axis were added to the cocultures at 50 μg/ml HDL-cholesterol. After 8 hours of incubation, supernatants were collected and assayed for monocyte chemotactic activity using standard neuroprobe chambers. The data are mean±SD of the number of migrated monocytes in 9 fields, for triplicate samples from each of two separate experiments. Asterisks indicate statistically significant difference at the level of p<0.05 between the values for the individual compounds as compared to those for the combination.

As demonstrated in Example 2, adding a low dosage of D-4F (1 μg/ml) to the drinking water of apoE null mice for 24 hours did not significantly improve HDL function (see, e.g., FIG. 9). FIG. 9 also shows that adding 0.05 mg/ml of atorvastatin or pravastatin alone to the drinking water of the apoE null mice for 24 hours did not improve HDL function. However, when D-4F 1 μg/ml was added to the drinking water together with 0.05 mg/ml of atorvastatin or pravastatin there was a significant improvement in HDL function (see, e.g., FIG. 9). Indeed the pro-inflammatory apoE null HDL became as anti-inflammatory as 350 μg/ml of normal human HDL (h, HDL).

Thus, doses of D-4F alone, or statins alone, which by themselves had no effect on HDL function when given together acted synergistically. When D-4F and a statin were given together to apo E null mice, their pro-inflammatory HDL at 50 μg/ml of HDL-cholesterol became as effective as normal human HDL at 350 μg/ml of HDL-cholesterol in preventing the inflammatory response induced by the action of HPODE oxidizing PAPC in cocultures of human artery wall cells.

Thus, in certain embodiments this invention provides methods for enhancing the activity of statins. The methods generally involve administering one or more peptides as described herein concurrently with one or more statins. The D-4F or other similar peptides as described herein achieve synergistic action between the statin and the orally peptide(s) to ameliorate atherosclerosis. In this context statins can be administered at significantly lower dosages thereby avoiding various harmful side effects (e.g. muscle wasting) associated with high dosage statin use and/or the anti-inflammatory properties of statins at any given dose are significantly enhanced.

III. Inhibiting/Treating Osteoporosis.

Vascular calcification and osteoporosis often co-exist in the same subjects (Ouchi et al. (1993) *Ann NY Acad Sci.*, 676: 297-307; Boukhris and Becker ('1972) *JAMA*, 219: 1307-1311; Banks et al. (1994) *Eur J Clin Invest.*, 24: 813-817; Laroche et al. (1994) *Clin Rheumatol.*, 13: 611-614; Broulik and Kapitola (1993) *Endocr Regul.*, 27: 57-60; Frye et al. (1992) Bone Mine., 19: 185-194; Barengolts et al. (1998) *Calcif Tissue Int.*, 62: 209-213; Burnett and Vasikaran (2002) *Ann Clin Biochem.*, 39: 203-210. Parhami et al. (Parhami et al. (1997) *Arterioscl Thromb Vasc Biol.*, 17: 680-687) demonstrated that mildly oxidized LDL (MM-LDL) and the biologically active lipids in MM-LDL [i.e. oxidized 1-palmitoyl-2-arachidonoyl-sn-glycero-3-phosphorylcholine) (Ox-PAPC)], as well as the isoprostane, 8-iso prostaglandin $E_2$, but not the unoxidized phospholipid (PAPC) or isoprostane 8-iso progstaglandin $F_{2\alpha}$ induced alkaline phosphatase activity and osteoblastic differentiation of calcifying vascular cells (CVCs) in vitro, but inhibited the differentiation of MC3T3-E1 bone cells.

The osteon resembles the artery wall in that the osteon is centered on an endothelial cell-lined lumen surrounded by a subendothelial space containing matrix and fibroblast-like cells, which is in turn surrounded by preosteoblasts and osteoblasts occupying a position analogous to smooth muscle cells in the artery wall (Id.). Trabecular bone osteoblasts also interface with bone marrow subendothelial spaces (Id.). Parhami et al. postulated that lipoproteins could cross the endothelium of bone arteries and be deposited in the subendothelial space where they could undergo oxidation as in coronary arteries (Id.). Based on their in vitro data they predicted that LDL oxidation in the subendothelial space of bone arteries and in bone marrow would lead to reduced osteoblastic differentiation and mineralization which would contribute to osteoporosis (Id.). Their hypothesis further predicted that LDL levels would be positively correlated with osteoporosis as they are with coronary calcification (Pohle et al. (2001) *Circulation*, 104: 1927-1932) but HDL levels would be negatively correlated with osteoporosis (Parhami et al. (1997) *Arterioscl Thromb Vasc Biol.*, 17: 680-687).

In vitro, the osteoblastic differentiation of the marrow stromal cell line M2-10B4 was inhibited by MM-LDL but not native LDL (Parhami et al. (1999) *J Bone Miner Res.*, 14: 2067-2078). When marrow stromal cells from atherosclerosis susceptible C57BL/6 (BL6) mice fed a low fat chow diet were cultured there was robust osteogenic differentiation (Id.). In contrast, when the marrow stromal cells taken from the mice after a high fat, atherogenic diet were cultured they did not undergo osteogenic differentiation (Id.). This observation is particularly important since it provides a possible explanation for the decreased osteogenic potential of marrow stromal cells in the development of osteoporosis (Nuttall and Gimble (2000) *Bone*, 27: 177-184). In vivo the decrease in osteogenic potential is accompanied by an increase in adipogenesis in osteoporotic bone (Id.).

It was found that adding D-4F to the drinking water of apoE null mice for 6 weeks dramatically increased trabecular bone mineral density (Example 3).

The data indicate that osteoporosis can be regarded as an "atherosclerosis of bone". It appears to be a result of the action of oxidized lipids. HDL destroys these oxidized lipids and promotes osteoblastic differentiation. The data illustrated in Example 3 indicate that administering peptide(s) of this invention to a mammal (e.g. in the drinking water of apoE null mice) dramatically increases trabecular bone in just a matter of weeks.

This indicates that the peptides described herein are useful for mitigation one or more symptoms of atherosclerosis (e.g. for inhibiting decalcification) or for inducing recalcification of osteoporotic bone. The peptides are also useful as prophylactics to prevent the onset of symptom(s) of osteoporosis in a mammal (e.g. a patient at risk for osteoporosis).

IV. Mitigation of a Symptom of Atherosclerosis.

We discovered that normal HDL inhibits three steps in the formation of mildly oxidized LDL. In those studies (see, copending application U.S. Ser. No. 09/541,468, filed on Mar. 31, 2000) we demonstrated that treating human LDL in vitro with apo A-I or an apo A-I mimetic peptide (37pA) removed seeding molecules from the LDL that included HPODE and HPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures.

Figure 2:
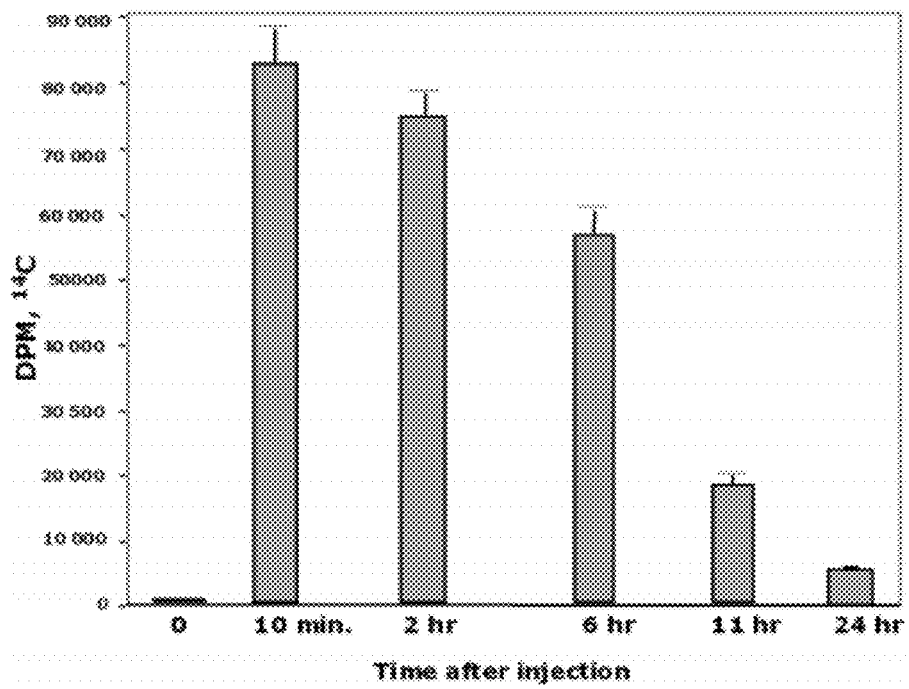
FIG. 2 illustrates the blood concentration of D-4F. Twenty-two μg of $^{14}$C-D-4F, 140,000 DPM in 100 μl of water was administered to 4-month-old female apoE null mice via tail vein injection (n=4 mice for each time point). Blood samples were obtained at the indicated time points and $^{14}$C-radioactivity in 1.0 ml of plasma was determined.
Figure 3:
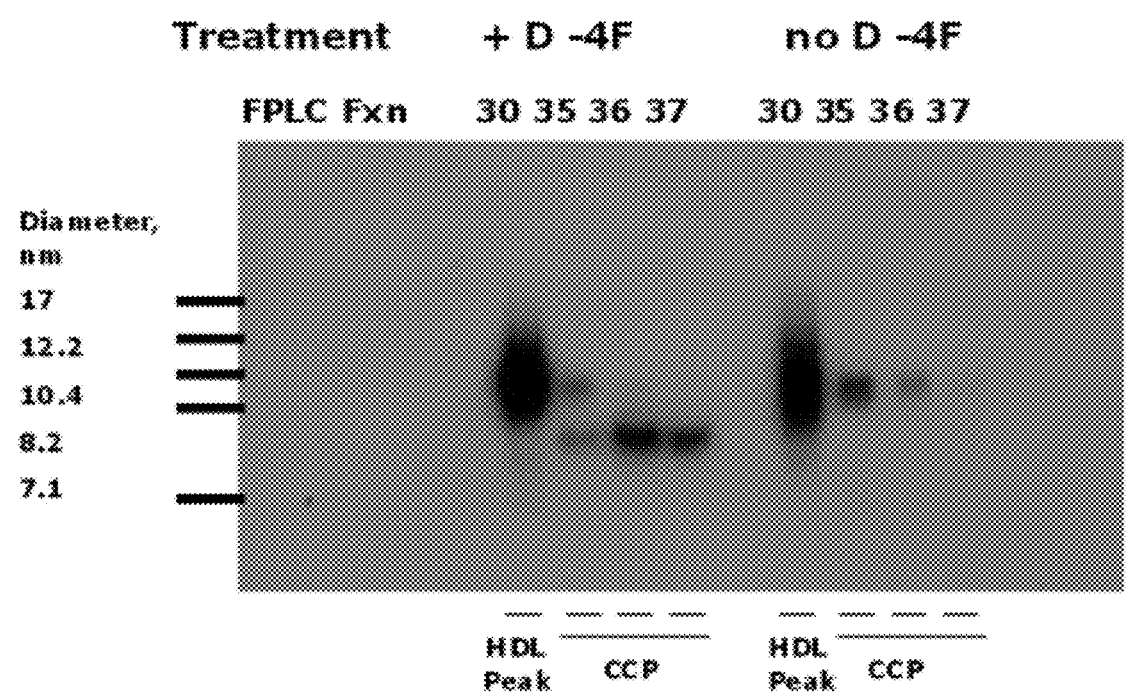
FIG. 3 shows the results from a Western blot for mouse apoA-I. ApoE null mice were given 500 μg D-4F (+D-4F) or not given (no D-4F) by stomach tube 20 min prior to being bled. Plasma was separated by FPLC and fractions 30, 35, 36, and 37 were analyzed by native-PAGE and Western blotting using antisera to mouse apoA-I. The diameter of the particles is shown on the left. (FPLC Fxn=FPLC fraction number; HDL Peak=fraction 30; CCP=fractions 35 to 37).
Figure 4A:
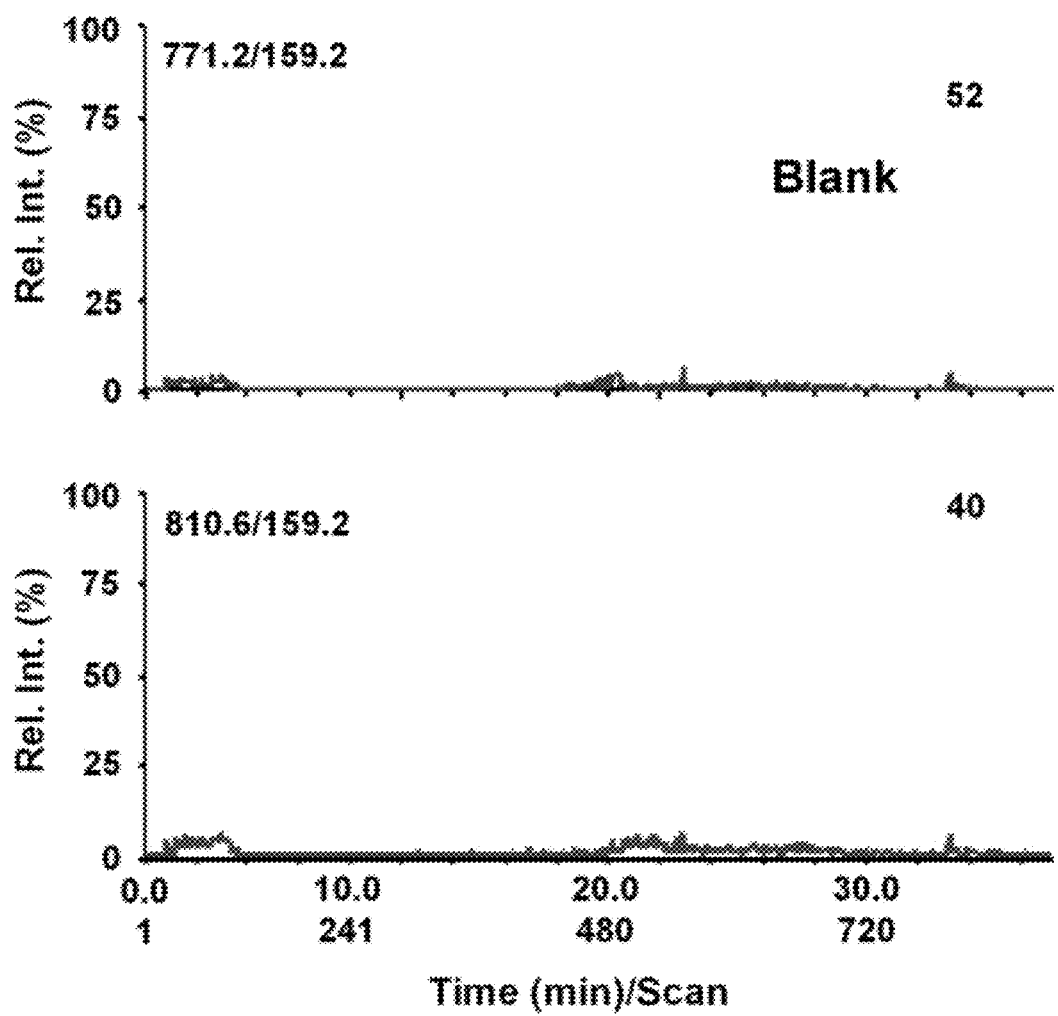
FIGS. 4A, 4B, and 4C show the results of an LC-MRM analysis. Twenty min after instilling 500 μg D-4F into the stomachs of apoE null mice, the mice were bled and their plasma was fractionated by FPLC and the fractions analyzed by LC-MRM after adding D-5F as an internal standard.
Figure 4B:
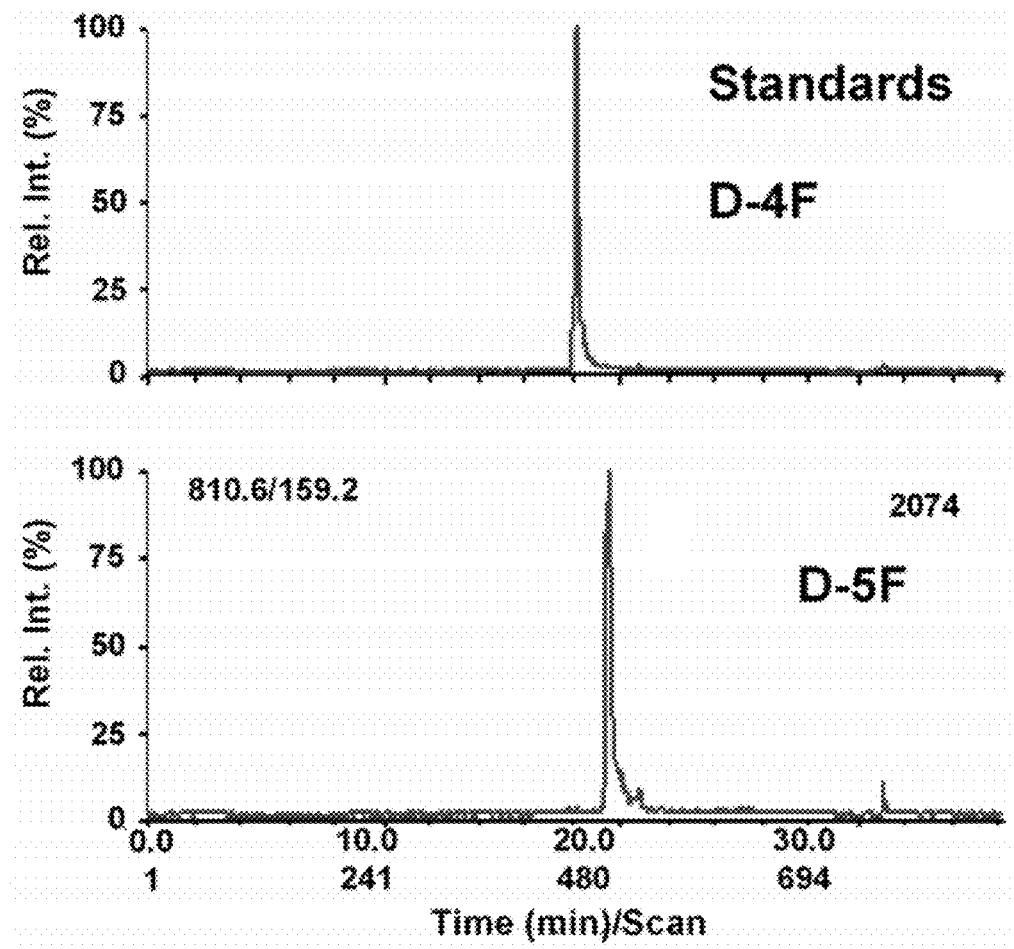
Figure 4C:
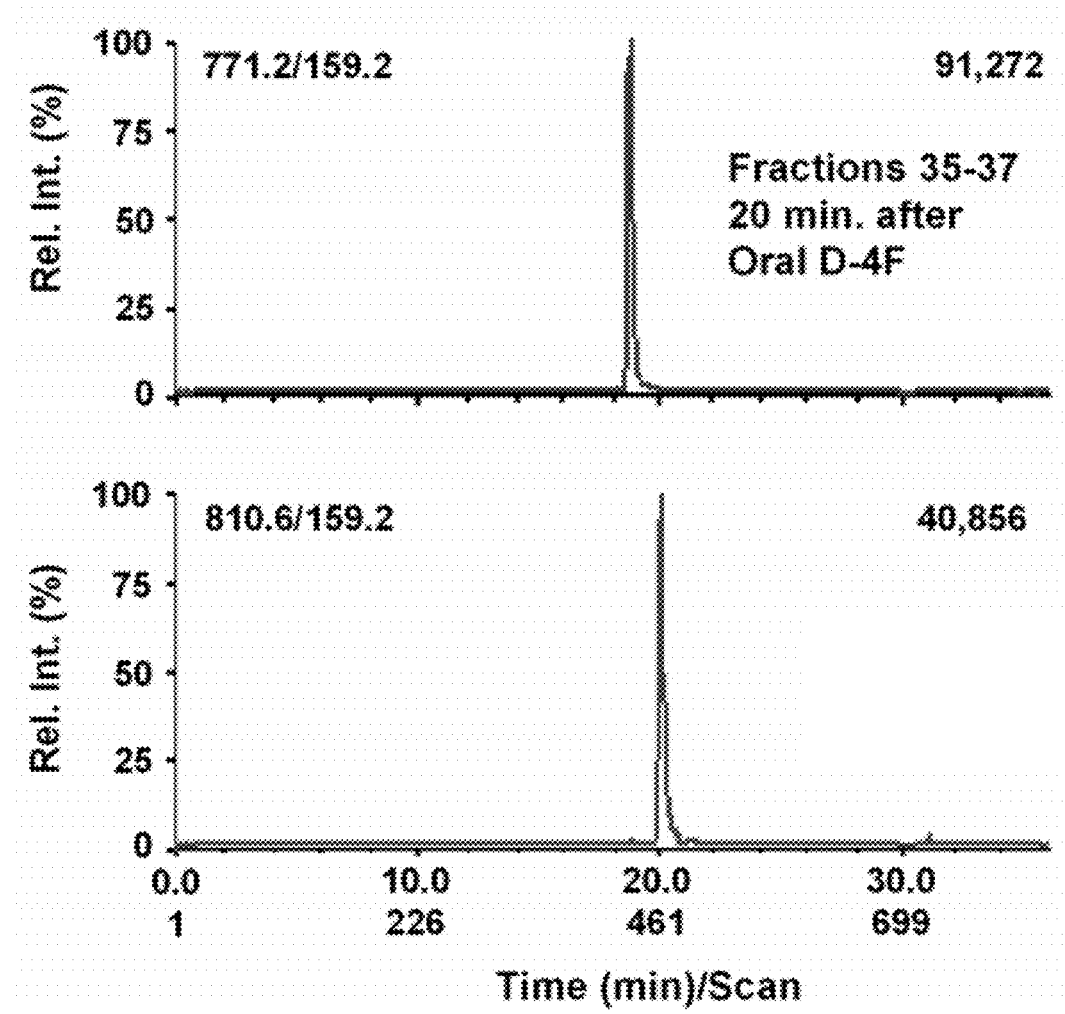

The protective function of the D peptides of this invention is illustrated in the parent applications (Ser. No. 09/645,454, filed Aug. 24, 2000, Ser. No. 09/896,841, filed Jun. 29, 2001, and WO 02/15923 (PCT/US01/26497), filed Jun. 29, 2001, see, e.g., FIGS. 1-5 in WO 02/15923. FIG. 1, panels A, B, C, and D in WO 02/15923 show the association of $^{14}$C-D-5F with blood components in an ApoE null mouse. It is also demonstrated that HDL from mice that were fed an atherogenic diet and injected with PBS failed to inhibit the oxidation of human LDL and failed to inhibit LDL-induced monocyte chemotactic activity in human artery wall cocultures. In contrast, HDL from mice fed an atherogenic diet and injected daily with peptides described herein was as effective in inhibiting human LDL oxidation and preventing LDL-induced monocyte chemotactic activity in the cocultures as was normal human HDL (FIGS. 2A and 2B in WO 02/15923). In addition, LDL taken from mice fed the atherogenic diet and injected daily with PBS was more readily oxidized and more readily induced monocyte chemotactic activity than LDL taken from mice fed the same diet but injected with 20 μg daily of peptide 5F. The D peptide did not appear to be immunogenic (FIG. 4 in WO 02/15923).

Figure 5:
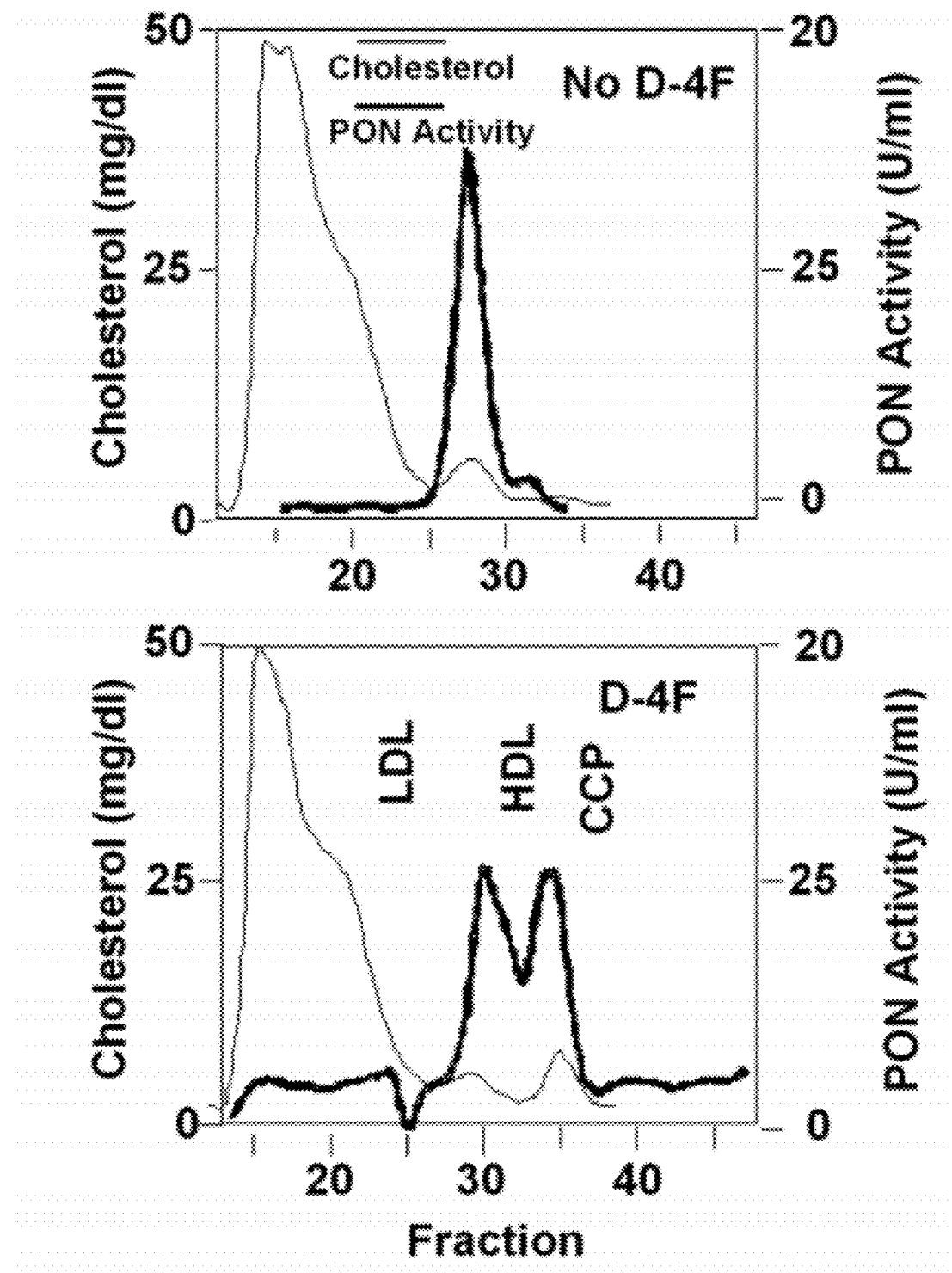
FIG. 5 illustrates cholesterol and paraoxonase Activity. Twenty min after instilling saline (No D-4F, top panel) or 500 μg D-4F (+D-4F, bottom panel) into the stomachs of apoE null mice, the mice were bled and their plasma fractionated by FPLC and cholesterol (thin black line) and paraoxonase (PON) activity (thick black line) determined in the fractions. The bottom panel shows the fractions with cholesterol containing particles (CCP) that appeared to the right of HDL after D-4F. As shown in the bottom panel, the CCP fractions also contained PON activity after D-4F.

The in vitro responses of human artery wall cells to HDL and LDL from mice fed the atherogenic diet and injected with a peptide according to this invention are consistent with the protective action shown by such peptides in vivo. Despite, similar levels of total cholesterol, LDL-cholesterol, IDL+ VLDL-cholesterol, and lower HDL-cholesterol as a percent of total cholesterol, the animals fed the atherogenic diet and injected with the peptide had significantly lower lesion scores (FIG. 5 in WO 02/15923). The peptides of this invention thus prevented progression of atherosclerotic lesions in mice fed an atherogenic diet.

Thus, in one embodiment, this invention provides methods for ameliorating and/or preventing one or more symptoms of atherosclerosis.

VI. Mitigation of a Symptom of Atheroscloerosis Associated with an Acute Inflammatory Response.

The peptides of this invention are also useful in a number of contexts. For example, we have observed that cardiovascular complications (e.g. atherosclerosis, stroke, etc.) frequently accompany or follow the onset of an acute phase inflammatory response. Such an acute state inflammatory response is often associated with a recurrent inflammatory disease (e.g., leprosy, tuberculosis, systemic lupus erythematosus, and rheumatoid arthritis), a viral infection (e.g. influenza), a bacterial infection, a fungal infection, an organ transplant, a wound or other trauma, an implanted prosthesis, a biofilm, and the like.

It was a surprising discovery of this invention that administration of one or more of the peptides described herein, can reduce or prevent the formation of oxidized phospholipids during or following an acute phase response and thereby mitigate or eliminate cardiovascular complications associated with such a condition.

Thus, for example, we have demonstrated that a consequence of influenza infection is the diminution in paraoxonase and platelet activating acetylhydrolase activity in the HDL. Without being bound by a particular theory, we believe that, as a result of the loss of these HDL enzymatic activities and also as a result of the association of pro-oxidant proteins with HDL during the acute phase response, HDL is no longer able to prevent LDL oxidation and was no longer able to prevent the LDL-induced production of monocyte chemotactic activity by endothelial cells.

We observed that in a subject injected with very low dosages of the polypeptides of this invention (e.g. 20 micrograms for mice) daily after infection with the influenza A virus paraoxonase levels did not fall and the biologically active oxidized phospholipids were not generated beyond background. This indicates that D-4F (and/or other peptides of this invention) can be administered (e.g. orally or by injection) to patients with known coronary artery disease during influenza infection or other events that can generate an acute phase inflammatory response (e.g. due to viral infection, bacterial infection, trauma, transplant, various autoimmune conditions, etc.) and thus we can prevent by this short term treatment the increased incidence of heart attack and stroke associated with pathologies that generate such inflammatory states.

Thus, in certain embodiments, this invention contemplates administering one or more of the peptides of this invention to a subject at risk for, or incurring, an acute inflammatory response and/or at risk for or incurring a symptom of atherosclerosis.

Thus, for example, a person having or at risk for coronary disease may prophylactically be administered a polypeptide of this invention during flu season. A person (or animal) subject to a recurrent inflammatory condition, e.g. rheumatoid arthritis, various autoimmune diseases, etc., can be treated with a polypeptide of this invention to mitigate or prevent the development of atherosclerosis or stroke. A person (or animal) subject to trauma, e.g. acute injury, tissue transplant, etc. can be treated with a polypeptide of this invention to mitigate the development of atherosclerosis or stroke.

In certain instances such methods will entail a diagnosis of the occurrence or risk of an acute inflammatory response. The acute inflammatory response typically involves alterations in metabolism and gene regulation in the liver. It is a dynamic homeostatic process that involves all of the major systems of the body, in addition to the immune, cardiovascular and central nervous system. Normally, the acute phase response lasts only a few days; however, in cases of chronic or recurring inflammation, an aberrant continuation of some aspects of the acute phase response may contribute to the underlying tissue damage that accompanies the disease, and may also lead to further complications, for example cardiovascular diseases or protein deposition diseases such as amyloidosis.

An important aspect of the acute phase response is the radically altered biosynthetic profile of the liver. Under normal circumstances, the liver synthesizes a characteristic range of plasma proteins at steady state concentrations. Many of these proteins have important functions and higher plasma levels of these acute phase reactants (APRs) or acute phase proteins (APPs) are required during the acute phase response following an inflammatory stimulus. Although most APRs are synthesized by hepatocytes, some are produced by other cell types, including monocytes, endothelial cells, fibroblasts and adipocytes. Most APRs are induced between 50% and several-fold over normal levels. In contrast, the major APRs can increase to 1000-fold over normal levels. This group includes serum amyloid A (SAA) and either C-reactive protein (CRP) in humans or its homologue in mice, serum amyloid P component (SAP). So-called negative APRs are decreased in plasma concentration during the acute phase response to allow an increase in the capacity of the liver to synthesize the induced APRs.

In certain embodiments, the acute phase response, or risk therefore is evaluated by measuring one or more APPs. Measuring such markers is well known to those of skill in the art, and commercial companies exist that provide such measurement (e.g. AGP measured by Cardiotech Services, Louisville, Ky.).

VII. Mitigation of a Symptom or Condition Associated with Coronary Calcification and Osteoporosis.

We have also identified oxidized lipids as a cause of coronary calcification and osteoporosis. Moreover, without being bound to a particularly theory, we believe the same mechanisms are involved in the pathogenesis of calcific aortic stenosis.

Thus, in certain embodiments, this invention contemplates the use of the peptides described herein to inhibit or prevent a symptom of a disease such as polymyalgia rheumatica, polyarteritis nodosa, scleroderma, lupus erythematosus, idiopathic pulmonary fibrosis, chronic obstructive pulmonary disease, Alzheimer's Disease, AIDS, coronary calcification, calcific aortic stenosis, osteoporosis, and the like.

V. Peptide Administration.

The methods of this invention typically involve administering to an organism, preferably a mammal, more preferably a human one or more of the peptides of this invention (or mimetics of such peptides). The peptide(s) can be administered, as described herein, according to any of a number of standard methods including, but not limited to injection, suppository, nasal spray, time-release implant, transdermal patch, and the like. In one particularly preferred embodiment, the peptide(s) are administered orally (e.g. as a syrup, capsule, or tablet).

The methods can involve the administration of a single peptide of this invention or the administration of two or more different peptides. The peptides can be provided as monomers or in dimeric, oligomeric or polymeric forms. In certain embodiments, the multimeric forms may comprise associated monomers (e.g. ionically or hydrophobically linked) while certain other multimeric forms comprise covalently linked monomers (directly linked or through a linker).

While the invention is described with respect to use in humans, it is also suitable for animal, e.g. veterinary use. Thus preferred organisms include, but are not limited to humans, non-human primates, canines, equines, felines, porcines, ungulates, largomorphs, and the like.

The methods of this invention are not limited to humans or non-human animals showing one or more symptom(s) of atherosclerosis (e.g. hypertension, plaque formation and rupture, reduction in clinical events such as heart attack, angina, or stroke, high levels of plasma cholesterol, high levels of low density lipoprotein, high levels of very low density lipoprotein, or inflammatory proteins such as CRP, etc.), but are useful in a prophylactic context. Thus, the peptides of this invention (or mimetics thereof) may be administered to organisms to prevent the onset/development of one or more symptoms of atherosclerosis. Particularly preferred subjects in this context are subjects showing one or more risk factors for atherosclerosis (e.g. family history, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

The peptides of this invention can also be administered to stimulate the formation and cycling of pre-beta high density lipoprotein-like particles and/or to promote reverse lipid transport and detoxification.

The peptides are also useful for administration with statins where they enhance (e.g., synergize) the activity of the statin and permit the statin(s) to be administered at lower dosages and/or the anti-inflammatory properties of statins at any given dose are significantly enhanced.

In addition, the peptides can be administered to reduce or eliminate one or more symptoms of osteoporosis and/or to prevent/inhibit the onset of one or more symptoms of osteoporosis.

VIII. Preferred Peptides and Their Preparation.

Preferred Peptides.

It was a discovery of this invention that peptides comprising a class A amphipathic helix ("class A peptides"), are capable of mitigating one or more symptoms of atherosclerosis. Class A peptides are characterized by formation of an $\alpha$-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) Meth. Enzymol., 128: 626-668). It is noted that the fourth exon of apo A-I, when folded into 3.667 residues/turn produces a class A amphipathic helical structure.

One particularly preferred class A peptide, designated 18A (see, 1, and also Anantharamaiah (1986) Meth. Enzymol., 128: 626-668) was modified as described herein to produce peptides orally administratable and highly effective at inhibiting or preventing one or more symptoms of atherosclerosis. Without being bound by a particular theory, it is believed that the peptides of this invention act in vivo may by picking up seeding molecule(s) that mitigate oxidation of LDL.

We determined that increasing the number of Phe residues on the hydrophobic face of 18A would theoretically increase lipid affinity as determined by the computation described by Palgunachari et al. (1996) Arteriosclerosis, Thrombosis, & Vascular Biology 16: 328-338. Theoretically, a systematic substitution of residues in the nonpolar face of 18A with Phe could yield six peptides. Peptides with an additional 2, 3 and 4 Phe would have theoretical lipid affinity ($\lambda$) values of 13, 14 and 15 units, respectively. However, the $\lambda$ values jumped four units if the additional Phe were increased from 4 to 5 (to 19$\lambda$ units). Increasing to 6 or 7 Phe would produce a less dramatic increase (to 20 and 21$\lambda$ units, respectively). Therefore, we chose 5 additional Phe (and hence the peptides designation as 5F). In one particularly preferred embodiment, the 5F peptide was blocked in that the amino terminal residue was acetylated and the carboxyl terminal residue was amidated.

The new class A peptide analog, 5F, inhibited lesion development in atherosclerosis-susceptible mice. The new peptide analog, 5F, was compared with mouse apo A-I (MoA-I) for efficacy in inhibiting diet-induced atherosclerosis in these mice using peptide dosages based on the study by Levine et al. (Levine et al. (1993) Proc. Natl. Acad. Sci. USA 90:12040-12044).

A number of other class A peptides were also produced and showed varying, but significant degrees of efficacy in mitigating one or more symptoms of atherosclerosis. A number of such peptides are illustrated in Table 1.

TABLE 1

Preferred peptides for use in this invention.

| Peptide Name | Amino Acid Sequence | SEQ ID NO. |
|---|---|---|
| 18A | D-W-L-K-A-F-Y-D-K-V-A-E-K-L-K-E-A-F | 1 |
| 2F | Ac-D-W-L-K-A-F-Y-D-K-V-A-E-K-L-K-E-A-F-NH$_2$ | 2 |

TABLE 1-continued

Preferred peptides for use in this invention.

| Peptide Name | Amino Acid Sequence | SEQ ID NO. |
|---|---|---|
| 3F | Ac-D-W-F-K-A-F-Y-D-K-V-A-E-K-L-K-E-A-F-NH$_2$ | 3 |
| 3F14 | Ac-D-W-L-K-A-F-Y-D-K-V-A-E-K-F-K-E-A-F-NH$_2$ | 4 |
| 4F | Ac-D-W-F-K-A-F-Y-D-K-V-A-E-K-F-K-E-A-F-NH$_2$ | 5 |
| 5F | Ac-D-W-L-K-A-F-Y-D-K-V-F-E-K-F-K-E-F-F-NH$_2$ | 6 |
| 6F | Ac-D-W-L-K-A-F-Y-D-K-F-F-E-K-F-K-E-F-F-NH$_2$ | 7 |
| 7F | Ac-D-W-F-K-A-F-Y-D-K-F-F-E-K-F-K-E-F-F-NH$_2$ | 8 |
|  | Ac-D-W-L-K-A-F-Y-D-K-V-A-E-K-L-K-E-F-F-NH$_2$ | 9 |
|  | Ac-D-W-L-K-A-F-Y-D-K-V-F-E-K-F-K-E-A-F-NH$_2$ | 10 |
|  | Ac-D-W-L-K-A-F-Y-D-K-V-F-E-K-L-K-E-F-F-NH$_2$ | 11 |
|  | Ac-D-W-L-K-A-F-Y-D-K-V-A-E-K-F-K-E-F-F-NH$_2$ | 12 |
|  | Ac-D-W-L-K-A-F-Y-D-K-V-F-E-K-F-K-E-F-F-NH$_2$ | 13 |
|  | Ac-E-W-L-K-L-F-Y-E-K-V-L-E-K-F-K-E-A-F-NH$_2$ | 14 |
|  | Ac-E-W-L-K-A-F-Y-D-K-V-A-E-K-F-K-E-A-F-NH$_2$ | 15 |
|  | Ac-E-W-L-K-A-F-Y-D-K-V-A-E-K-L-K-E-F-F-NH$_2$ | 16 |
|  | Ac-E-W-L-K-A-F-Y-D-K-V-A-E-K-F-K-E-A-F-NH$_2$ | 17 |
|  | Ac-E-W-L-K-A-F-Y-D-K-V-F-E-K-L-K-E-F-F-NH$_2$ | 18 |
|  | Ac-E-W-L-K-A-F-Y-D-K-V-A-E-K-F-K-E-F-F-NH$_2$ | 19 |
|  | Ac-E-W-L-K-A-F-Y-D-K-V-F-E-K-F-K-E-F-F-NH$_2$ | 20 |
|  | AC-A-F-Y-D-K-V-A-E-K-L-K-E-A-F-NH$_2$ | 21 |
|  | Ac-A-F-Y-D-K-V-A-E-K-F-K-E-A-F-NH$_2$ | 22 |
|  | Ac-A-F-Y-D-K-V-A-E-K-F-K-E-A-F-NH$_2$ | 23 |
|  | Ac-A-F-Y-D-K-F-F-E-K-F-K-E-F-F-NH$_2$ | 24 |
|  | Ac-A-F-Y-D-K-F-F-E-K-F-K-E-F-F-NH$_2$ | 25 |
|  | Ac-A-F-Y-D-K-V-A-E-K-F-K-E-A-F-NH$_2$ | 26 |
|  | Ac-A-F-Y-D-K-V-A-E-K-L-K-E-F-F-NH$_2$ | 27 |
|  | Ac-A-F-Y-D-K-V-A-E-K-F-K-E-A-F-NH$_2$ | 28 |
|  | Ac-A-F-Y-D-K-V-F-E-K-L-K-E-F-F-NH$_2$ | 29 |
|  | Ac-A-F-Y-D-K-V-F-E-K-F-K-E-F-F-NH$_2$ | 30 |
|  | Ac-K-A-F-Y-D-K-V-F-E-K-F-K-E-F-NH$_2$ | 31 |
|  | Ac-L-F-Y-E-K-V-L-E-K-F-K-E-A-F-NH$_2$ | 32 |
|  | Ac-A-F-Y-D-K-V-A-E-K-F-K-E-A-F-NH$_2$ | 33 |
|  | Ac-A-F-Y-D-K-V-A-E-K-L-K-E-F-F-NH$_2$ | 34 |
|  | Ac-A-F-Y-D-K-V-F-E-K-F-K-E-A-F-NH$_2$ | 35 |
|  | Ac-A-F-Y-D-K-V-F-E-K-L-K-E-F-F-NH$_2$ | 36 |
|  | Ac-A-F-Y-D-K-V-A-E-K-F-K-E-F-F-NH$_2$ | 37 |
|  | Ac-A-F-Y-D-K-V-F-E-K-F-K-E-F-F-NH$_2$ | 38 |
|  | Ac-D-W-L-K-A-L-Y-D-K-V-A-E-K-L-K-E-A-L-NH$_2$ | 39 |
|  | Ac-D-W-F-K-A-F-Y-E-K-V-A-E-K-L-K-E-F-F-NH$_2$ | 40 |
|  | Ac-D-W-F-K-A-F-Y-D-K-F-F-E-K-F-K-E-F-F-NH$_2$ | 41 |
|  | Ac-E-W-L-K-A-L-Y-E-K-V-A-E-K-L-K-E-A-L-NH$_2$ | 42 |
|  | Ac-E-W-L-K-A-F-Y-D-K-V-A-E-K-L-K-E-A-F-NH$_2$ | 43 |
|  | Ac-E-W-F-K-A-F-Y-D-K-V-A-E-K-L-K-E-F-F-NH$_2$ | 44 |
|  | Ac-E-W-L-K-A-F-Y-D-K-V-F-E-K-F-K-E-F-F-NH$_2$ | 45 |
|  | Ac-E-W-L-K-A-F-Y-D-K-F-F-E-K-F-K-E-F-F-NH$_2$ | 46 |
|  | Ac-E-W-F-K-A-F-Y-D-K-F-F-E-K-F-K-E-F-F-NH$_2$ | 47 |
|  | Ac-D-F-L-K-A-W-Y-D-K-V-A-E-K-L-K-E-A-W-NH$_2$ | 48 |
|  | Ac-E-F-L-K-A-W-Y-E-K-V-A-E-K-L-K-E-A-W-NH$_2$ | 49 |
|  | Ac-D-F-W-K-A-W-Y-D-K-V-A-E-K-L-K-E-W-W-NH$_2$ | 50 |
|  | Ac-E-F-W-K-A-W-Y-E-K-V-A-E-K-L-K-E-W-W-NH$_2$ | 51 |
|  | Ac-D-K-L-K-A-F-Y-D-K-V-F-E-W-A-K-E-A-F-NH$_2$ | 52 |
|  | Ac-D-K-W-K-A-V-Y-D-K-F-A-E-A-F-K-E-F-L-NH$_2$ | 53 |
|  | Ac-E-K-L-K-A-F-Y-E-K-V-F-E-W-A-K-E-A-F-NH$_2$ | 54 |
|  | Ac-E-K-W-K-A-V-Y-E-K-F-A-E-A-F-K-E-F-L-NH$_2$ | 55 |
|  | Ac-D-W-L-K-A-F-V-D-K-F-A-E-K-F-K-E-A-Y-NH$_2$ | 56 |
|  | Ac-E-K-W-K-A-V-Y-E-K-F-A-E-A-F-K-E-F-L-NH$_2$ | 57 |

TABLE 1-continued

Preferred peptides for use in this invention.

| Peptide Name | Amino Acid Sequence | SEQ ID NO. |
|---|---|---|
| | Ac-D-W-L-K-A-F-V-Y-D-K-V-F-K-L-K-E-F-F-NH$_2$ | 58 |
| | Ac-E-W-L-K-A-F-V-Y-E-K-V-F-K-L-K-E-F-F-NH$_2$ | 59 |
| | Ac-D-W-L-R-A-F-Y-D-K-V-A-E-K-L-K-E-A-F-NH$_2$ | 60 |
| | Ac-E-W-L-R-A-F-Y-E-K-V-A-E-K-L-K-E-A-F-NH$_2$ | 61 |
| | Ac-D-W-L-K-A-F-Y-D-R-V-A-E-K-L-K-E-A-F-NH$_2$ | 62 |
| | Ac-E-W-L-K-A-F-Y-E-R-V-A-E-K-L-K-E-A-F-NH$_2$ | 63 |
| | Ac-D-W-L-K-A-F-Y-D-K-V-A-E-R-L-K-E-A-F-NH$_2$ | 64 |
| | Ac-E-W-L-K-A-F-Y-E-K-V-A-E-R-L-K-E-A-F-NH$_2$ | 65 |
| | Ac-D-W-L-K-A-F-Y-D-K-V-A-E-K-L-R-E-A-F-NH$_2$ | 66 |
| | Ac-E-W-L-K-A-F-Y-E-K-V-A-E-K-L-R-E-A-F-NH$_2$ | 67 |
| | Ac-D-W-L-K-A-F-Y-D-R-V-A-E-R-L-K-E-A-F-NH$_2$ | 68 |
| | Ac-E-W-L-K-A-F-Y-E-R-V-A-E-R-L-K-E-A-F-NH$_2$ | 69 |
| | Ac-D-W-L-R-A-F-Y-D-K-V-A-E-K-L-R-E-A-F-NH$_2$ | 70 |
| | Ac-E-W-L-R-A-F-Y-E-K-V-A-E-K-L-R-E-A-F-NH$_2$ | 71 |
| | Ac-D-W-L-R-A-F-Y-D-R-V-A-E-K-L-K-E-A-F-NH$_2$ | 72 |
| | Ac-E-W-L-R-A-F-Y-E-R-V-A-E-K-L-K-E-A-F-NH$_2$ | 73 |
| | Ac-D-W-L-K-A-F-Y-D-K-V-A-E-R-L-R-E-A-F-NH$_2$ | 74 |
| | Ac-E-W-L-K-A-F-Y-E-K-V-A-E-R-L-R-E-A-F-NH$_2$ | 75 |
| | Ac-D-W-L-R-A-F-Y-D-K-V-A-E-R-L-K-E-A-F-NH$_2$ | 76 |
| | Ac-E-W-L-R-A-F-Y-E-K-V-A-E-R-L-K-E-A-F-NH$_2$ | 77 |
| | D-W-L-K-A-F-Y-D-K-V-A-E-K-L-K-E-A-F-P-<br>D-W-L-K-A-F-Y-D-K-V-A-E-K-L-K-E-A-F | 78 |
| | D-W-L-K-A-F-Y-D-K-V-A-E-K-L-K-E-F-F-P-<br>D-W-L-K-A-F-Y-D-K-V-A-E-K-L-K-E-F-F | 79 |
| | D-W-F-K-A-F-Y-D-K-V-A-E-K-L-K-E-A-F-P-<br>D-W-F-K-A-F-Y-D-K-V-A-E-K-L-K-E-A-F | 80 |
| | D-K-L-K-A-F-Y-D-K-V-F-E-W-A-K-E-A-F-P-<br>D-K-L-K-A-F-Y-D-K-V-F-E-W-L-K-E-A-F | 81 |
| | D-K-W-K-A-V-Y-D-K-F-A-E-A-F-K-E-F-L-P-<br>D-K-W-K-A-V-Y-D-K-F-A-E-A-F-K-E-F-L | 82 |
| | D-W-F-K-A-F-Y-D-K-V-A-E-K-F-K-E-A-F-P-<br>D-W-F-K-A-F-Y-D-K-V-A-E-K-F-K-E-A-F | 83 |
| | D-W-L-K-A-F-V-Y-D-K-V-F-K-L-K-E-F-F-P-<br>D-W-L-K-A-F-V-Y-D-K-V-F-K-L-K-E-F-F | 84 |
| | D-W-L-K-A-F-Y-D-K-F-A-E-K-F-K-E-F-F-P-<br>D-W-L-K-A-F-Y-D-K-F-A-E-K-F-K-E-F-F | 85 |
| | Ac-E-W-F-K-A-F-Y-E-K-V-A-E-K-F-K-E-A-F-NH$_2$ | 86 |
| | Ac-D-W-F-K-A-F-Y-D-K-V-A-E-K-F-NH$_2$ | 87 |
| | Ac-F-K-A-F-Y-D-K-V-A-E-K-F-K-E-NH$_2$ | 88 |
| | Ac-F-K-A-F-Y-E-K-V-A-E-K-F-K-E-NH$_2$ | 89 |
| | NMA-F-K-A-F-Y-D-K-V-A-E-K-F-K-E-NH$_2$ | 90 |
| | NMA-F-K-A-F-Y-E-K-V-A-E-K-F-K-E-NH$_2$ | 91 |
| | NMA-D-W-F-K-A-F-Y-D-K-V-A-E-K-F-K-E-A-F-NH$_2$ | 92 |
| | NMA-E-W-F-K-A-F-Y-E-K-V-A-E-K-F-K-E-A-F-NH$_2$ | 93 |
| | NMA-A-F-Y-D-K-V-A-E-K-F-K-E-A-F-NH$_2$ | 94 |
| | NMA-D-W-F-K-A-F-Y-D-K-V-A-E-K-F-NH$_2$ | 95 |
| | Ac-D-W-L-K-A-F-Y-D-K-V-F-E-K-F-K-E-F-F-NH$_2$ | 96 |
| | NMA-D-W-L-K-A-F-Y-D-K-V-F-E-K-F-K-E-F-F-NH$_2$ | 96 |
| | Ac-E-W-L-K-A-F-Y-E-K-V-F-E-K-F-K-E-F-F-NH$_2$ | 97 |
| | NMA-E-W-L-K-A-F-Y-E-K-V-F-E-K-F-K-E-F-F-NH$_2$ | 97 |
| | Ac-A-F-Y-D-K-V-F-E-K-F-K-E-F-F-NH$_2$ | 98 |
| | NMA-A-F-Y-D-K-V-F-E-K-F-K-E-F-F-NH$_2$ | 98 |
| | Ac-A-F-Y-E-K-V-F-E-K-F-K-E-F-F-NH$_2$ | 99 |
| | NMA-A-F-Y-E-K-V-F-E-K-F-K-E-F-F-NH$_2$ | 99 |
| | Ac-D-W-L-K-A-F-Y-D-K-V-F-E-K-F-NH$_2$ | 100 |
| | NMA-D-W-L-K-A-F-Y-D-K-V-F-E-K-F-NH$_2$ | 100 |
| | Ac-E-W-L-K-A-F-Y-E-K-V-F-E-K-F-NH$_2$ | 101 |
| | NMA-E-W-L-K-A-F-Y-E-K-V-F-E-K-F-NH$_2$ | 101 |
| | Ac-L-K-A-F-Y-D-K-V-F-E-K-F-K-E-NH$_2$ | 102 |
| | NMA -L-K-A-F-Y-D-K-V-F-E-K-F-K-E-NH$_2$ | 102 |
| | Ac-L-K-A-F-Y-E-K-V-F-E-K-F-K-E-NH$_2$ | 103 |
| | NMA-L-K-A-F-Y-E-K-V-F-E-K-F-K-E-NH$_2$ | 103 |

[1]Linkers are underlined.
NMA is N-Methyl Anthranilyl.

In certain preferred embodiments, the peptides include variations of 4F or D-4F where one or both aspartic acids (D) are replaced by glutamic acid (E). Also contemplated are peptides (e.g. 4F or D-4F) where 1, 2, 3, or 4 amino acids are deleted from the carboxyl terminus and/or 1, 2, 3, or 4 amino acids are deleted from the carboxyl terminus and/or one or both aspartic acids (D) are replaced by glutamic acid (E). In any of the peptides described herein, the N-terminus can be blocked and labeled using a mantyl moiety (e.g. N-methylanthranilyl).

While various peptides of 1, are illustrated with an acetyl group or an N-methylanthranilyl group protecting the amino terminus and an amide group protecting the carboxyl terminus, any of these protecting groups may be eliminated and/or substituted with another protecting group as described herein. In particularly preferred embodiments, the peptides comprise one or more D-form amino acids as described herein. In certain embodiments, every amino acid (e.g. every enantiomeric amino acid) of the peptides of Table 1 is a D-form amino acid.

It is also noted that 1 is not fully inclusive. Using the teaching provided herein, other suitable peptides can routinely be produced (e.g. by conservative or semi-conservative substitutions (e.g. D replaced by E), extensions, deletions, and the like). Thus, for example, one embodiment utilizes truncations of any one or more of peptides identified by SEQ ID Nos:2-20 and 39-85. Thus, for example, SEQ ID NO: 21 illustrates a peptide comprising 14 amino acids from the C-terminus of 18A comprising one or more D amino acids, while SEQ ID NOS:22-38 illustrate other truncations. Longer peptides are also suitable. Such longer peptides may entirely form a class A amphipathic helix, or the class A amphipathic helix (helices) may form one or more domains of the peptide. In addition, this invention contemplates multimeric versions of the peptides. Thus, for example, the peptides illustrated in 1 can be coupled together (directly or through a linker (e.g. a carbon linker, or one or more amino acids) with one or more intervening amino acids). Illustrative polymeric peptides include 18A-Pro-18A and the peptides of SEQ ID NOs:79-85 preferably comprising one or more D amino acids, more preferably with every amino acid a D amino acid as described herein and/or having one or both termini protected.

It was a surprising discovery of this invention that, when the class A peptides (e.g. as illustrated in 1) incorporated D amino acids they retained their activity and, but could be administered orally. Moreover this oral administration resulted in relatively efficient uptake and significant serum half-life thereby providing an efficacious method of mitigating one or more symptoms of atherosclerosis.

Using the teaching provided herein, one of skill can routinely modify the illustrated class A peptides to produce other suitable class A peptides of this invention. For example, routine conservative or semi-conservative substitutions (e.g. E for D) can be made of the existing amino acids. The effect of various substitutions on lipid affinity of the resulting peptide can be predicted using the computational method described by Palgunachari et al. (1996) *Arteriosclerosis, Thrombosis, & Vascular Biology* 16: 328-338. The peptides can be lengthened or shortened as long as the class A α-helix structure is preserved. In addition, substitutions can be made to render the resulting peptide more similar to peptide(s) endogenously produced by the subject species.

In certain embodiments, the peptides of this invention comprise "D" forms of the peptides described in U.S. Pat. No. 4,643,988, more preferably "D" forms having one or both termini coupled to protecting groups. Such peptides include peptides having the formula $A_1$-$B_1$-$B_2$-$C_1$-D-$B_3$-$B_4$-$A_2$-$C_2$-$B_5$-$B_6$-$A_3$-$C_3$-$B_7$-$C_4$-$A_4$-$B_8$-$B_9$ (SEQ ID NO: 104) wherein $A_1$, $A_2$, $A_3$ and $A_4$ are independently aspartic acid or glutamic acid, or homologues or analogues thereof; $B_1$, $B_2$, $B_3$, $B_4$, $B_5$, $B_6$, $B_7$, $B_8$ and $B_9$ are independently tryptophan, phenylalanine, alanine, leucine, tyrosine, isoleucine, valine or α-naphthylalanine, or homologues or analogues thereof; $C_1$, $C_2$, $C_3$ and $C_4$ are independently lysine or arginine, and D is serine, threonine, alanine, glycine, histidine, or homologues or analogues thereof; provided that, when $A_1$ and $A_2$ are aspartic acid, $A_3$ and $A_4$ are glutamic acid, $B_2$ and $B_9$ are leucine, $B_3$ and $B_7$ are phenylalanine, $B_4$ is tyrosine, $B_5$ is valine, $B_6$, $B_8$, and D are alanine, and $C_1$, $C_2$, $C_3$ and $C_4$ are lysine, $B_1$ is not Tryptophan, where at one enantiomeric amino acid is a "D" form amino acids. Preferably at least 50% of the enantiomeric amino acids are "D" form, more preferably at least 80% of the enantiomeric amino acids are "D" form, and most preferably at least 90% or even all of the enantiomeric amino acids are "D" form amino acids.

While, in preferred embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

In addition to the class A peptides described herein, peptidomimetics are also contemplated herein. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) *Adv. Drug Res.* 15: 29; Veber and Freidinger (1985) *TINS* p. 392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (i.e., 5F described herein), but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —CH(OH)$CH_2$—, —$CH_2SO$—, etc. by methods known in the art and further described in the following references: Spatola (1983) p. 267 in *Chemistry and Biochemistry of Amino Acids, Peptides, and Proteins*, B. Weinstein, eds., Marcel Dekker, New York; Spatola (1983) *Vega Data* 1(3) *Peptide Backbone Modifications*. (general review); Morley (1980) *Trends Pharm Sci* pp. 463-468 (general review); Hudson et al. (1979) *Int J Pept Prot Res* 14:177-185 (—$CH_2NH$—, $CH_2CH_2$—); Spatola et al. (1986) *Life Sci* 38:1243-1249 (—$CH_2$—S); Hann, (1982) *J Chem Soc Perkin Trans* I 307-314 (—CH—CH—, cis and trans); Almquist et al. (1980) *J Med Chem.* 23:1392-1398 (—$COCH_2$—); Jennings-White et al. (1982) *Tetrahedron Lett.* 23:2533 (—$COCH_2$—); Szelke, M. et al., European Appln. EP 45665 (1982) CA: 97:39405 (1982) (—CH(OH)CH2-); Holladay et al. (1983) *Tetrahedron Lett* 24:4401-4404 (—C(OH)$CH_2$—); and Hruby (1982) *Life Sci.*, 31:189-199 (—$CH_2$—S—)).

A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circularly permutations of the peptides described herein or constrained peptides (including cyclized peptides) comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide.

Peptide Preparation.

The peptides used in this invention can be chemically synthesized using standard chemical peptide synthesis techniques or, particularly where the peptide does not comprise "D" amino acid residues, the peptide can readily be recombinantly expressed. Where the "D" polypeptides are recombinantly expressed, a host organism (e.g. bacteria, plant, fungal cells, etc.) can be cultured in an environment where one or more of the amino acids is provided to the organism exclusively in a D form. Recombinantly expressed peptides in such a system then incorporate those D amino acids.

In certain embodiments, D amino acids can be incorporated in recombinantly expressed peptides using modified amino acyl-tRNA synthetases that recognize D-amino acids.

In certain preferred embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis; pp*. 3-284 in *The Peptides: Analysis, Synthesis, Biology. Vol.* 2: *Special Methods in PeptideSynthesis, Part A*.; Merrifield et al. (1963) *J. Am. Chem. Soc.,* 85: 2149-2156, and Stewart et al. (1984) *Solid Phase Peptide Synthesis,* 2nd ed. Pierce Chem. Co., Rockford, Ill.

In one embodiment, the peptides are synthesized by the solid phase peptide synthesis procedure using a benzhyderylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are describe in a miniprint supplement accompanying Anantharamaiah et al. (1985) *J. Biol. Chem.,* 260(16): 10248-10255.

It is noted that in the chemical synthesis of peptides, particularly peptides comprising D amino acids, the synthesis usually produces a number of truncated peptides in addition to the desired full-length product. The purification process (e.g. HPLC) typically results in the loss of a significant amount of the full-length product.

It was a discovery of this invention that, particularly in the synthesis of a D peptide (e.g. D-4), in order to prevent loss in purifying the longest form one can dialyze and use the mixture and thereby eliminate the last HPLC purification. Such a mixture loses about 50% of the potency of the highly purified product (e.g. per wt of protein product), but the mixture contains about 6 times more peptide and thus greater total activity.

D-Form Amino Acids.

D-amino acids can be incorporated at one or more positions in the peptide simply by using a D-form derivatized amino acid residue in the chemical synthesis. D-form residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form amino acids can be completely omitted or incorporated at any position in the peptide as desired. Thus, for example, in certain embodiments, the peptide can comprise a single D-amino acid, while in other embodiments, the peptide comprises at least two, generally at least three, more generally at least four, most generally at least five, preferably at least six, more preferably at least seven and most preferably at least eight D amino acids. In particularly preferred embodiments, essentially every other (enantiomeric) amino acid is a D-form amino acid. In certain embodiments at least 90%, preferably at least 90%, more preferably at least 95% of the enantiomeric amino acids are D-form amino acids. In one particularly preferred embodiment, essentially every enantiomeric amino acid is a D-form amino acid.

Protecting Groups.

In certain embodiments, the one or more R-groups on the constituent amino acids and/or the terminal amino acids are blocked with a protecting group. Without being bound by a particular theory, it was a discovery of this invention that blockage, particularly of the amino and/or carboxyl termini of the subject peptides of this invention greatly improves oral delivery and significantly increases serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain embodiments, the blocking groups can additionally act as a detectable label (e.g. N-methyl anthranilyl).

In certain particularly preferred embodiments, the protecting groups include, but are not limited to alkyl chains as in fatty acids, propionyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3—(CH_2)_n—CO—$ where n ranges from about 1 to about 20, preferably from about 1 to about 16 or 18, more preferably from about 3 to about 13, and most preferably from about 3 to about 10.

In certain particularly preferred embodiments, the protecting groups include, but are not limited to alkyl chains as in fatty acids, propionyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3—(CH_2)_n—CO—$ where n ranges from about 3 to about 20, preferably from about 3 to about 16, more preferably from about 3 to about 13, and most preferably from about 3 to about 10.

Other protecting groups include, but are not limited to N-methyl anthranilyl, Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis, 2nd ed.*, John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

IX. Enhancing Peptide Uptake.

It was also a surprising discovery of this invention that when an all L amino acid peptide (e.g. otherwise having the sequence of the peptides of this invention) is administered in conjunction with the D-form (i.e. a peptide of this invention) the uptake of the D-form peptide is increased. Thus, in certain embodiments, this invention contemplates the use of combinations of D-form and L-form peptides in the methods of this invention. The D-form peptide and the L-form peptide can have different amino acid sequences, however, in preferred embodiments, they both have amino acid sequences of peptides described herein, and in still more preferred embodiments, they have the same amino acid sequence.

It was also a discovery of this invention that concatamers of the class A amphipathic helix peptides of this invention are also effective in mitigating one or more symptoms of atherosclerosis. The monomers comprising the concatamers can be coupled directly together or joined by a linker. In certain embodiments, the linker is an amino acid linker (e.g. a proline), or a peptide linker (e.g. $Gly_4Ser_3$, SEQ ID NO:106). In certain embodiments, the concatamer is a 2 mer, more preferably a 3 mer, still more preferably a 4 mer, and most preferably 5 mer, 8 mer or 10 mer.

X. Pharmaceutical Formulations.

In order to carry out the methods of the invention, one or more peptides or peptide mimetics of this invention are administered, e.g. to an individual diagnosed as having one or more symptoms of atherosclerosis, or as being at risk for atherosclerosis. The peptides or peptide mimetics can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the peptides or mimetics are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The peptides or mimetics identified herein are useful for parenteral, topical, oral, nasal (or otherwise inhaled), rectal, or local administration, such as by aerosol or transdermally, for prophylactic and/or therapeutic treatment of atherosclerosis and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The peptides and/or peptide mimetics of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering from one or more symptoms of atherosclerosis or at risk for atherosclerosis in an amount sufficient to cure or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of peptide or mimetic can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. It will be appreciated that such dosages may be varied to optimize a therapeutic regimen in a particular subject or group of subjects.

In certain preferred embodiments, the peptides or peptide mimetics of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Sustained Release Formulations.

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) *Biotechnol. Prog.* 14: 108; Johnson et al. (1996), *Nature Med.* 2: 795; Herbert et al. (1998), *Pharmaceut. Res.* 15, 357) a dry powder composed of biodegradable polymeric microspheres containing the protein in a polymer matrix that can be compounded as a dry formulation with or without other agents.

The ProLease microsphere fabrication process was specifically designed to achieve a high protein encapsulation efficiency while maintaining protein integrity. The process consists of (i) preparation of freeze-dried protein particles from bulk protein by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the protein, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

Combined Formulations.

In certain instances, one or more peptides of this invention are administered in conjunction with one or more active agents (e.g. statins, beta blockers, ACE inhibitors, lipids, etc.). The two agents (e.g. peptide and statin) can be administered simultaneously or sequentially. When administered sequentially the two agents are administered so that both achieve a physiologically relevant concentration over a similar time period (e.g. so that both agents are active at some common time).

In certain embodiments, both agents are administered simultaneously. In such instances it can be convenient to provide both agents in a single combined formulation. This can be achieved by a variety of methods well known to those of skill in the art. For example, in a table formulation the table can comprise two layers one layer comprising, e.g. the statin(s), and the other layer comprising e.g. the peptide(s). In a time release capsule, the capsule can comprise two time release bead sets, one for the peptide(s) and one containing the statin(s).

The foregoing formulations and administration methods are intended to be illustrative and not limiting. It will be appreciated that, using the teaching provided herein, other suitable formulations and modes of administration can be readily devised.

XI. Additional Pharmacologically Active Agents.

Additional pharmacologically active agents may be delivered along with the primary active agents, e.g., the peptides of this invention. In one embodiment, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

Statins.

It was a surprising discovery that administration of one or more peptides of this invention "concurrently" with one or more statins synergistically enhances the effect of the statin(s). That is, the statins can achieve a similar efficacy at lower dosage thereby obviating potential adverse side effects (e.g. muscle wasting) associated with these drugs and/or cause the statins to be significantly more anti-inflammatory at any given dose.

The major effect of the statins is to lower LDL-cholesterol levels, and they lower LDL-cholesterol more than many other types of drugs. Statins generally inhibit an enzyme, HMG-CoA reductase, that controls the rate of cholesterol production in the body. These drugs typically lower cholesterol by slowing down the production of cholesterol and by increasing the liver's ability to remove the LDL-cholesterol already in the blood.

The large reductions in total and LDL-cholesterol produced by these drugs appears to result in large reductions in heart attacks and heart disease deaths. Thanks to their track record in these studies and their ability to lower LDL-cholesterol, statins have become the drugs most often prescribed when a person needs a cholesterol-lowering medicine. Studies using statins have reported 20 to 60 percent lower LDL-cholesterol levels in patients on these drugs. Statins also reduce elevated triglyceride levels and produce a modest increase in HDL-cholesterol. Recently it has been appreciated that statins have anti-inflammatory properties that may not be directly related to the degree of lipid lowering achieved. For example it has been found that statins decrease the plasma levels of the inflammatory marker CRP relatively independent of changes in plasma lipid levels. This anti-inflammatory activity of statins has been found to be as or more important in predicting the reduction in clinical events induced by statins than is the degree of LDL lowering.

The statins are usually given in a single dose at the evening meal or at bedtime. These medications are often given in the evening to take advantage of the fact that the body makes more cholesterol at night than during the day. When combined with the peptides described herein, the combined peptide/statin treatment regimen will also typically be given in the evening.

Suitable statins are well known to those of skill in the art. Such statins include, but are not limited to atorvastatin (Lipitor®, Pfizer), simvastatin (Zocor®, Merck0, pravastatin (Pravachol®, Bristol-Myers Squibb0, fluvastatin (Lescol®, Novartis), lovastatin (Mevacor®, Merck), rosuvastatin (Crestor®, Astra Zeneca), and Pitavastatin (Sankyo), and the like.

The combined statin/peptide dosage can be routinely optimized for each patient. Typically statins show results after several weeks, with a maximum effect in 4 to 6 weeks. Prior to combined treatment with a statin and one of the peptides described herein, the physician would obtain routine tests for starting a statin including LDL-cholesterol and HDL-cholesterol levels. Additionally, the physician would also measure the anti-inflammatory properties of the patient's HDL and determine CRP levels with a high sensitivity assay. After about 4 to 6 weeks of combined treatment, the physician would typically repeat these tests and adjust the dosage of the medications to achieve maximum lipid lowering and maximum anti-inflammatory activity.

Beta Blockers.

Suitable beta blockers include, but are not limited to cardioselective (selective beta 1 blockers), e.g., acebutolol (Sectral®), atenolol (Tenormin®), betaxolol (KERLONE®), bisoprolol (ZEBETA®), metoprolol (LOPRESSOR®), and the like. Suitable non-selective blockers (block beta 1 and beta 2 equally) include, but are not limited to carteolol (CARTROL®), nadolol (CORGARD®), penbutolol (LEVATOL®), pindolol (VISKEN®), propranolol (INDERAL®), timolol (BLOCKADREN®), labetalol (NORMODYNE®, TRANDATE®), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

ACE Inhibitors.

Suitable ace inhibitors include, but are not limited to captopril (e.g. CAPOTEN® by Squibb), benazepril (e.g., LOTENSIN® by Novartis), enalapril (e.g., VASOTEC® by Merck), fosinopril (e.g., MONOPRIL® by Bristol-Myers), lisinopril (e.g. PRINIVIL® by Merck or ZESTRIL® by Astra-Zeneca), quinapril (e.g. ACCUPRIL® by Parke-Davis), ramipril (e.g., ALTACE® by Hoechst Marion Roussel, King Pharmaceuticals), imidapril, perindopril erbumine (e.g., ACEON® by Rhone-Polenc Rorer), trandolapril (e.g., MAVIK® by Knoll Pharmaceutical), and the like. Suitable ARBS (Ace Receptor Blockers) include but are not limited to losartan (e.g. COZAAR® by Merck), irbesartan (e.g., AVAPRO® by Sanofi), candesartan (e.g., ATACAND® by Astra Merck), valsartan (e.g., DIOVAN® by Novartis), and the like.

Lipid-Based Formulations.

In certain embodiments, the peptides of this invention are administered in conjunction with one or more lipids. The lipids can be formulated as an active agent, and/or as an excipient to protect and/or enhance transport/uptake of the peptides or they can be administered separately.

Without being bound by a particular theory, it was discovered of this invention that administration (e.g. oral administration) of certain phospholipids can significantly increase HDL/LDL ratios. In addition, it is believed that certain medium-length phospholipids are transported by a process different than that involved in general lipid transport. Thus, co-administration of certain medium-length phospholipids with the peptides of this invention confer a number of advantages: They protect the phospholipids from digestion or hydrolysis, they improve peptide uptake, and they improve HDL/LDL ratios.

The lipids can be formed into liposomes that encapsulate the polypeptides of this invention and/or they can be simply complexed/admixed with the polypeptides. Methods of making liposomes and encapsulating reagents are well known to those of skill in the art (see, e.g., Martin and Papahadjopoulos (1982) *J. Biol. Chem.*, 257: 286-288; Papahadjopoulos et al. (1991) *Proc. Natl. Acad. Sci. USA*, 88: 11460-11464; Huang et al. (1992) *Cancer Res.*, 52:6774-6781; Lasic et al. (1992) *FEBS Lett.*, 312: 255-258., and the like).

Preferred phospholipids for use in these methods have fatty acids ranging from about 4 carbons to about 24 carbons in the sn-1 and sn-2 positions. In certain preferred embodiments, the fatty acids are saturated. In other preferred embodiments, the fatty acids can be unsaturated. Various preferred fatty acids are illustrated in Table 2.

TABLE 2

Preferred fatty acids in the sn-1 and/or sn-2 position of the preferred phospholipids for administration of D polypeptides.

| Carbon No. | Common Name | IUPAC Name |
|---|---|---|
| 3:0 | Propionoyl | Trianoic |
| 4:0 | Butanoyl | Tetranoic |
| 5:0 | Pentanoyl | Pentanoic |
| 6:0 | Caproyl | Hexanoic |
| 7:0 | Heptanoyl | Heptanoic |
| 8:0 | Capryloyl | Octanoic |
| 9:0 | Nonanoyl | Nonanoic |
| 10:0 | Capryl | Decanoic |
| 11:0 | Undcanoyl | Undecanoic |
| 12:0 | Lauroyl | Dodecanoic |
| 13:0 | Tridecanoyl | Tridecanoic |
| 14:0 | Myristoyl | Tetradecanoic |
| 15:0 | Pentadecanoyl | Pentadecanoic |
| 16:0 | Palmitoyl | Hexadecanoic |
| 17:0 | Heptadecanoyl | Heptadecanoic |
| 18:0 | Stearoyl | Octadecanoic |
| 19:0 | Nonadecanoyl | Nonadecanoic |
| 20:0 | Arachidoyl | Eicosanoic |
| 21:0 | Heniecosanoyl | Heniecosanoic |
| 22:0 | Behenoyl | Docosanoic |

TABLE 2-continued

Preferred fatty acids in the sn-1 and/or sn-2 position of the preferred phospholipids for administration of D polypeptides.

| Carbon No. | Common Name | IUPAC Name |
|---|---|---|
| 23:0 | Trucisanoyl | Trocosanoic |
| 24:0 | Lignoceroyl | Tetracosanoic |
| 14:1 | Myristoleoyl (9-cis) | |
| 14:1 | Myristelaidoyl (9-trans) | |
| 16:1 | Palmitoleoyl (9-cis) | |
| 16:1 | Palmitelaidoyl (9-trans) | |

The fatty acids in these positions can be the same or different. Particularly preferred phospholipids have phosphorylcholine at the sn-3 position.

XII. Kits.

In another embodiment this invention provides kits for amelioration of one or more symptoms of atherosclerosis and/or for the prophylactic treatment of a subject (human or animal) at risk for atherosclerosis and/or for stimulating the formation and cycling of pre-beta high density lipoprotein-like particles and/or for inhibiting one or more symptoms of osteoporosis. The kits preferably comprise a container containing one or more of the peptides or peptide mimetics of this invention. The peptide or peptide mimetic can be provided in a unit dosage formulation (e.g. suppository, tablet, caplet, patch, etc.) and/or may be optionally combined with one or more pharmaceutically acceptable excipients.

The kit can, optionally, further comprise one or more other agents used in the treatment of heart disease and/or atherosclerosis. Such agents include, but are not limited to, beta blockers, vasodilators, aspirin, statins, ace inhibitors or ace receptor inhibitors (ARBs) and the like, e.g. as described above.

In certain preferred embodiments, the kits additionally include a statin (e.g. cerivastatin, atorvastatin, simvastatin, pravastatin, fluvastatin, lovastatin, rosuvastatin, pitavastatin, etc.) either formulated separately or in a combined formulation with the peptide(s). Typically the dosage of a statin in such a formulation can be lower than the dosage of a statin typically prescribed without the synergistic peptide.

In addition, the kits optionally include labeling and/or instructional materials providing directions (i.e., protocols) for the practice of the methods or use of the "therapeutics" or "prophylactics" of this invention. Preferred instructional materials describe the use of one or more polypeptides of this invention to mitigate one or more symptoms of atherosclerosis and/or to prevent the onset or increase of one or more of such symptoms in an individual at risk for atherosclerosis and/or to stimulate the formation and cycling of pre-beta high density lipoprotein-like particles and/or to inhibit one or more symptoms of osteoporosis. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Lipid Transport and Detoxification by Stimulating the Formation and Cycling of Pre-Beta High Density Lipoprotein-Like Particles

The serum concentration of D-4F after oral administration was compared to that obtained by injection. FIG. 1 shows the results of administration of $^{14}$C-D-4F to apoE null mice by stomach tube. Blood samples were obtained at each time point shown in FIG. 1.

FIG. 2 demonstrates the radioactivity in plasma after the same amount of mass and radioactivity of D-4F was given to the mice by tail vein injection. The data in FIGS. 1 and 2 indicate that 2 hours after oral administration, about 1.2% of the radioactivity seen after IV injection was present in plasma. From a number of studies we have concluded that approximately 1% of an oral dose of D-4F is absorbed.

Based on the low absorption, one might think that D-4F would not be biologically active. Normal mouse plasma contains on the order of 100 mg/dl or 1 mg/ml of apoAI. Since apoE null mice have low HDL-cholesterol levels, if we assume that their apoA-I levels are only one-fifth normal, they would have about. 0.20 mg/ml of apoA-I. If we instilled 500 µg of D-4F into the stomach of a mouse and only 1% was absorbed, we would have added 5 µg of D-4F to approximately 1.5 ml of mouse plasma so we would have approximately 3.3 µg of D-4F per ml of mouse plasma. So how could 3.3 µg of D-4F per ml of mouse plasma influence lipid transport when apoE null mouse plasma already contains approximately 200 µg of apoA-I.

In other studies, 10 minutes after instilling either saline or 500 µg [$^{14}$C]-D-4F into the stomachs of apoE null mice there was no detectable D-4F in plasma. However, 20 minutes after D-4F was given, it was detected in plasma. When the plasma was fractionated by FPLC the HDL peak eluted in fraction 30 and the D-4F eluted in FPLC fractions 35 to 37 (labeled CCP in FIG. 3). In the absence of D-4F (no D-4F), fraction 35 contained some apoA-I by Western blotting, fraction 36 contained less apoA-I and fraction 37 contained almost no detectable apoA-I (FIG. 3). Moreover, in the absence of D-4F the size of the particles containing apoA-I was approximately 10.5 nm by PAGE (FIG. 3). Twenty min after giving D-4F (+D-4F), by Western blotting, fraction 35 contained some apoA-I, fraction 36 contained more apoA-I, and fraction 37 contained more apoA-I than in fraction 35, but less than in fraction 36 (FIG. 3). However after D-4F, the particles containing apoA-I in fractions 35-37 were smaller (8.5 vs 10.5 nm) (see +D-4F, CCP in FIG. 3).

By LC-MRM, 20 min after giving D-4F orally, fractions 35-37 were also seen to contain D-4F (FIG. 4). These results were also confirmed with $^{14}$C-D-4F. Additionally, after giving D-4F orally, the small particles in fractions 35-37 containing apoA-I also contained paraoxonase activity and cholesterol (FIG. 5, bottom panel). In the absence of D-4F, fractions 35-37 contained virtually no paraoxonase activity and very little if any cholesterol (FIG. 5 top panel).

The bottom panel of FIG. 5 shows the fractions with cholesterol containing particles (CCP) that appeared to the right of HDL after D-4F. As shown in the bottom panel of FIG. 5, the CCP fractions also contained paraoxonase (PON) activity after D-4F.

As indicated in FIG. 3, after giving D-4F orally and analyzing fractions 35-37 by PAGE these particles were approximately 8.5 nm in size. When these fractions were purified with preparative PAGE and examined by negative staining electron microscopy, their size was determined to be 8 to 9 nm confirming the estimation by PAGE. By 6.5 hours after giving D-4F orally, almost all of the D-4F had moved to larger lipoprotein particles with an affinity for HDL that was more than 10-fold greater than for B containing lipoproteins. Twenty min after $^{14}$C-D-4F was given by tail vein injection, there was more than 100-fold more D-4F in plasma as compared to after oral administration by stomach tube. However, the content of D-4F in FPLC fractions 35-37 was only about 2-fold greater after injection as compared to after oral administration (data not shown).

We conclude from these data that 20 min after absorption from the intestine D-4F forms small pre-beta HDL-like particles that contain relatively high amounts of apoA-I and paraoxonase. Indeed, estimating the amount of apoA-I in these pre-beta HDL-like particles from Western blots and comparing the amount of apoA-I to the amount of D-4F in these particles (determined by radioactivity or LC-MRM) suggests that as D-4F is absorbed from the intestine, it acts as a catalyst causing the formation of these pre-beta HDL-like particles. This small amount of intestinally derived D-4F somehow recruits amounts of apoA-I, paraoxonase, and cholesterol into these particles that are orders of magnitude more than the amount of D-4F.

Figure 6:
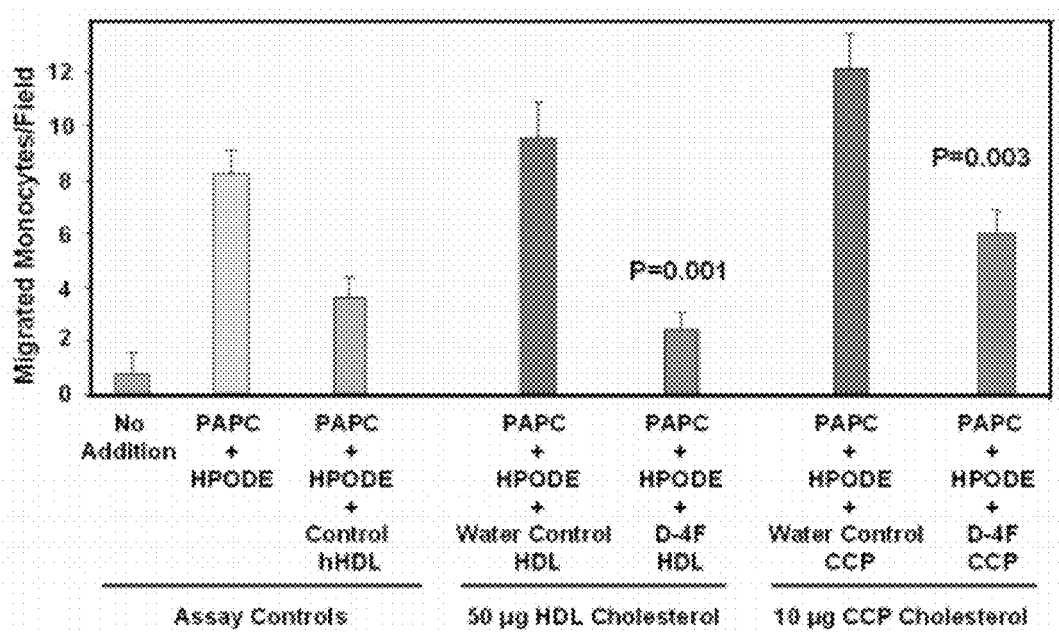
FIG. 6 illustrates the ability of the pre-beta HDL-like particles (CCP) in FIG. 5 to detoxify lipids and prevent human artery wall cells from producing an inflammatory reaction (monocyte chemotactic activity). Water or 500 g of D-4F were instilled into the stomachs of apoE null mice. Twenty minutes later the mice were bled and their plasma fractionated by FPLC. Fractions 28-30 contained HDL and fractions 35-37 contained the pre-beta HDL-like particles (CCP). Twenty μg of 1-palmitoyl-2-arachidonyl-sn-glycero-3-phosphorylcholine (PAPC) was added together with 1 μg/ml of hydroperoxyeicosatetraenoic acid (HPODE) to cocultures of human artery wall cells as described previously (Navab et al. (2001) J Lipid Res., 42: 1308-1317). Human HDL (h, HDL) was added at 350 μg/ml cholesterol or no addition was made to the cocultures (No Addition), or mouse HDL isolated by FPLC (fractions 28-30) from the mice given water alone (Water Control HDL) or D-4F (D-4F HDL) at 50 μg/ml HDL-cholesterol or the pre-beta HDL-like particle fractions (fractions 35-37) after water alone (Water Control CCP) or after D-4F (D-4F CCP) at 10 μg/ml cholesterol were added to the cocultures. After 8 hours of incubation, supernatants were collected and assayed for monocyte chemotactic activity using standard neuroprobe chambers. The data are mean±SD of the number of migrated monocytes in 9 fields, for triplicate samples.

Based on the content of apoA-I, D-4F and paraoxonase in the pre-beta HDL-like particles (CCP) generated 20 min after D-4F (FIGS. 3 to 5), one would predict that these pre-beta HDL-like particles would detoxify oxidized lipids and prevent artery wall cells from generating an inflammatory response manifested by the production of monocyte chemotactic activity. The experiments shown in FIG. 6 indicate that this was indeed the case. As shown in FIG. 6, the pre-beta HDL-like particle region (CCP) after FPLC separation of plasma from apoE null mice that did not receive D-4F promoted the oxidation of PAPC by HPODE and was pro-inflammatory. In contrast, after oral administration of D-4F to the apoE null mice, these fractions prevented the oxidation of PAPC by HPODE (detoxified the lipids) and were anti-inflammatory. Moreover, after D-4F the anti-inflammatory properties of the pre-beta HDL-like particles was similar to that achieved with a five-fold greater concentration of apoE null HDL after D-4F. As also shown in FIG. 6 apoE null HDL after D-4F achieved a degree of lipid detoxification similar to that achieved by normal human HDL without D-4F at a 7-fold greater concentration. Thus, the pre-beta HDL-like particles in the apoE null mice after D-4F were approximately 35-fold better able to detoxify the lipids and prevent the artery wall cells from producing monocyte chemotactic activity than was normal human HDL.

Figure 7:
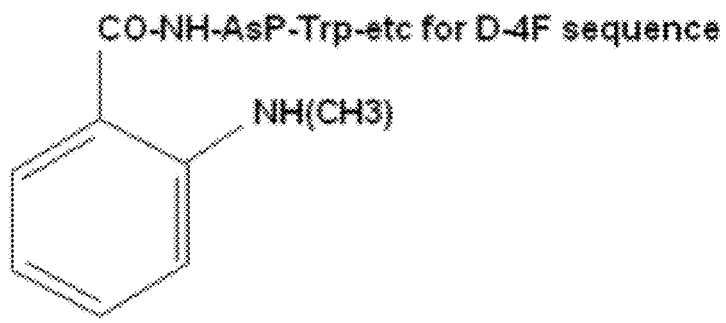
FIG. 7 illustrates the formula of N-methyl anthranilyl-D-4F. Only two terminal amino acids of the 4F polypeptide are shown.
Figure 8A:
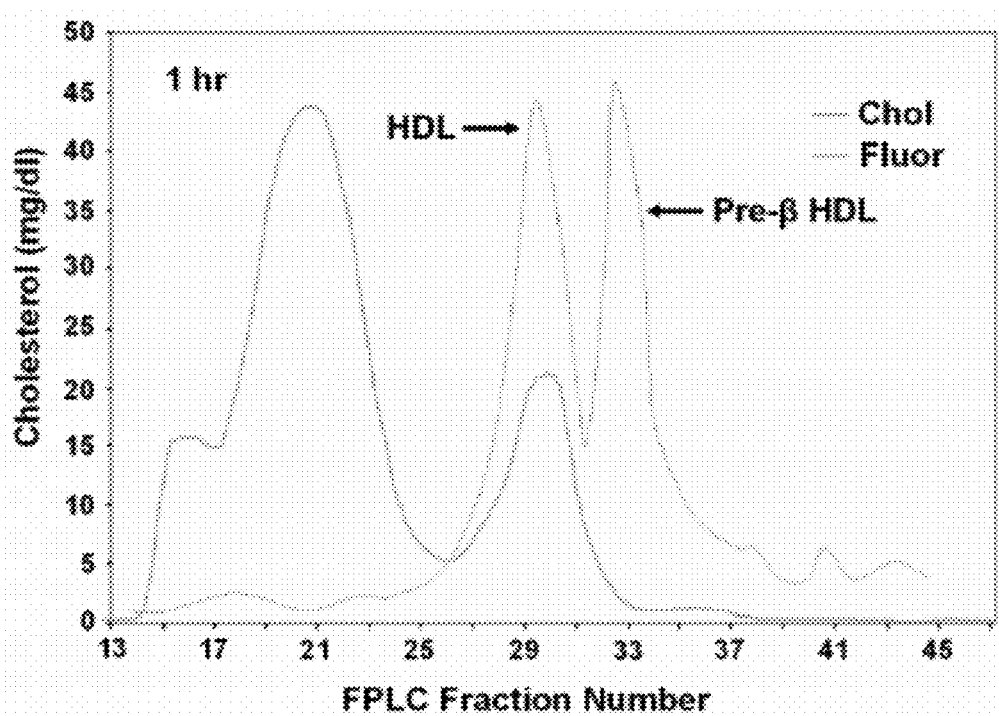
FIGS. 8A, 8B, and 8C illustrate the time course of D4F and plasma cholesterol. LDL receptor null female mice at 8 weeks of age (5 mice per group) were given by stomach tube 22 μg/mouse of N-Methyl Anthranilyl-D-4F and were then bleed 1, 2, or 8 hours later. Their plasma was fractionated by FPLC and analyzed for cholesterol and fluorescence. The 1-hour time point is shown in FIG. 8A, the 2 hour time point is shown in FIG. 8B, and the 8 hour time point is shown in FIG. 8C.
Figure 8B:
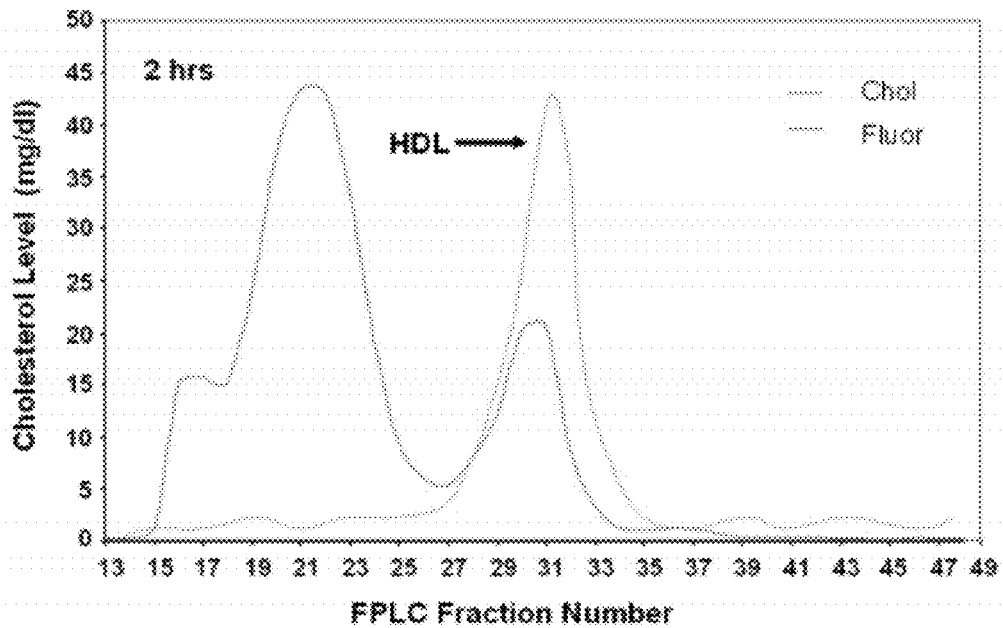
Figure 8C:
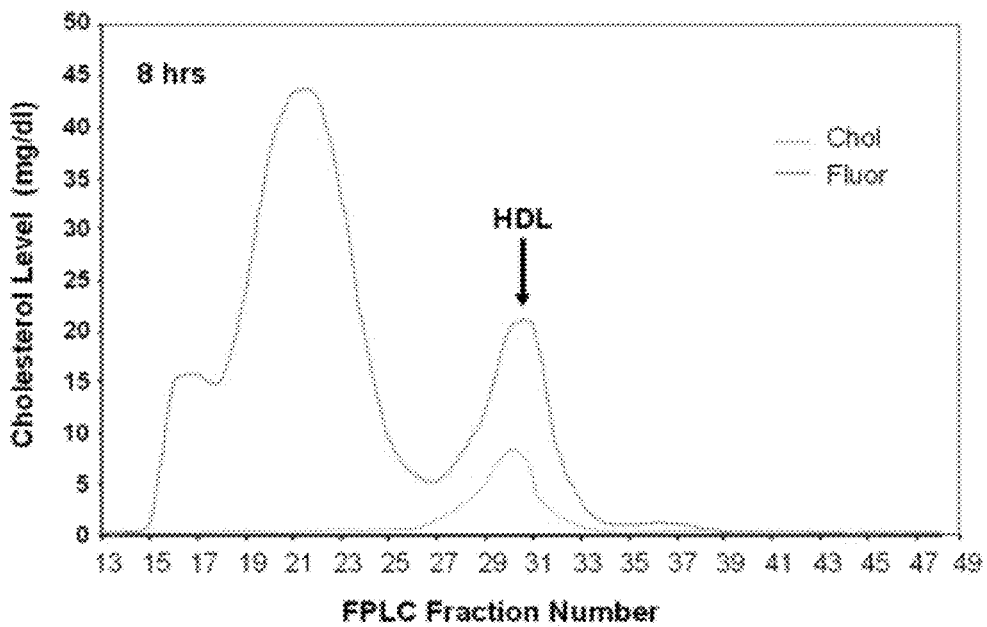

To follow the course of these particles over time we labeled D-4F with a novel fluorescent probe as shown in FIG. 7. LDL receptor null female mice at 8 weeks of age (5 mice per group) were given by stomach tube 22 µg/mouse of N-Methyl Anthranilyl-D-4F and were then bleed 1, 2, or 8 hours later. Their plasma was fractionated by FPLC and analyzed for cholesterol and fluorescence. The 1-hour time point is shown in FIG. 8A. The 2 hour time point is shown in FIG. 8B, and the 8 hour time point is shown in FIG. 8C.

Following absorption, D-4F rapidly recruits relatively large amounts of apoA-I and paraoxonase to form pre-beta HDL-like particles which are very likely the most potent particles for both promoting reverse cholesterol transport and for destroying biologically active oxidized lipids. We believe that the formation of these particles and their subsequent rapid incorporation into mature HDL likely explains the dramatic reduction in atherosclerosis that we observed in LDL receptor null mice on a Western diet and in apoE null mice on a chow diet independent of changes in plasma cholesterol or HDL-cholesterol. Based on these data, we believe the administration of peptides of this invention can promote lipid transport and "detoxification" by stimulating the formation and cycling of pre-beta high density lipoprotein-like particles.

Example 2

Synergistic Action Between Statins and Orally Administered Peptides to Ameliorate Atherosclerosis ApoE null female mice three months old on a chow diet were given drinking water alone (Water), or drinking water containing 1 µg/ml of D-4F, or 0.05 mg/ml of Atorvastatin, or 0.05 mg/ml of Pravastatin, or 1 µg/ml of D-4F together with 0.05 mg/ml of Atorvastatin, or 1 µg/ml of D-4F together with 0.05 mg/ml of Pravastatin. After 24 hours the mice were bled and their HDL was tested in a human artery wall coculture model. Twenty µg of 1-palmitoyl-2-arachidonyl-sn-glycero-3-phosphorylcholine (PAPC) was added together with 1 µg/ml of hydroperoxyeicosatetraenoic acid (HPODE) to cocultures of human artery wall cells as described previously (Navab et al. (2001) *J Lipid Res.* 42: 1308-1317). Human HDL (h, HDL) was added at 350 µg/ml cholesterol or no addition was made to the cocultures (No Addition), or mouse HDL isolated by FPLC from the mice given drinking water alone (Water) or the additions shown on the X-axis were added to the cocultures at 50 µg/ml HDL-cholesterol. After 8 hours of incubation, supernatants were collected and assayed for monocyte chemotactic activity using standard neuroprobe chambers.

The results are shown in FIG. 9. As shown in FIG. 9, adding 1 µg/ml of D-4F to the drinking water of apoE null mice for 24 hours did not significantly improve HDL function. FIG. 9 also shows that adding 0.05 mg/ml of atorvastatin or pravastatin alone to the drinking water of the apoE null mice for 24 hours did not improve HDL function. However, FIG. 9 shows that when D-4F 1 µg/ml was added to the drinking water together with 0.05 mg/ml of atorvastatin or pravastatin there was a significant improvement in HDL function. Indeed the pro-inflammatory apoE null HDL became as anti-inflammatory as 350 µg/ml of normal human HDL (h, HDL) (*=p<0.05).

Thus, doses of D-4F alone, or statins alone, which by themselves had no effect on HDL function when given together acted synergistically. When D-4F and a statin were given together to apo E null mice, their pro-inflammatory HDL at 50 µg/ml of HDL-cholesterol became as effective as normal human HDL at 350 µg/ml of HDL-cholesterol in preventing the inflammatory response induced by the action of HPODE oxidizing PAPC in cocultures of human artery wall cells.

Example 3

Use of Orally Administered Peptides to Ameliorate Osteoporosis

D-4F (Ac-D-W-F-K-A-F-Y-D-K-V-A-E-K-F-K-E-A-F-NH$_2$, SEQ ID NO: 5) at 1 mg/ml was or was not added to the drinking water of apoE null mice (8 mice per group). After 6 weeks mice were euthanized and the left femur from each mouse removed and analyzed by quantitative CT scanning to determine BMD. Scans were performed at 4 longitudinal axis positions (slices) for each femur, with 1 being most distal and 4 most proximal. Values of BMD are expressed as mean±SEM.

It was found that adding D-4F to the drinking water of apoE null mice for 6 weeks dramatically increased trabecular bone mineral density (Table 3).

TABLE 3

Effect of D-4F on bone mineral density (BMD) in mice.

| | Trabecular Bone Mineral Density (mg/cm$^3$) | | |
|---|---|---|---|
| Slice | Water | D-4F | Fold Increase |
| 1 | 3.1 ± 3 | 18 ± 4 | 5.8 |
| 2 | 1.9 ± 2 | 12 ± 6 | 6.3 |
| 3 | 1.7 ± 1 | 11 ± 6 | 6.5 |
| 4 | 7.3 ± 4 | 16 ± 6 | 2.2 |

It is interesting that bisphosphonates are particularly active on trabecular bone (Bohic et al. (2000) *Bone,* 26: 341-348; Ramamurthy et al. (2001) *Curr Med Chem.*, 8: 295-303; Rohanizadeh et al. (2000) *Calcif Tissue Int.*, 67: 330-336; Rodan (1997) *Bone* 20:1-4). Since it was determined that D-4F did not alter the lipid profile in these mice, it is likely that the beneficial effects of the peptide are due to interference with the inhibitory actions of oxidized lipids on bone. Our data cannot differentiate between an action on osteoblasts or osteoclasts but these preliminary data strongly suggest that D-4F may be an excellent agent to inhibit/prevent/treat osteoporosis.

Example 4

"L" Form Peptides are Effective

While the peptides of this invention, when synthesized from D-amino acids, were more effective when given orally than peptides comprising all L-amino acids ("L-form peptides"), the L-form peptides were also effective. This is amply illustrated in the examples provided in the priority documents of the present application (e.g. U.S. Ser. Nos. 09/645,454, 09/896,841, 10/187,215, and 10/273,386) all of which are incorporated herein by reference. For example in Example 1 on pages 46 to 57 of U.S. Ser. No. 10/187,215 (the '215 application), the specification of which is published in PCT/US01/26497 (WO 02/15923), evidence was presented that the peptide known as 5F synthesized from L-amino acids (Sequence ID No 6 in Table 1 page 27) when given by injection was cleared from the circulation of the mouse with a T$_{1/2}$ of 6.22 hours (see Table 3 on page 51), was not toxic (see page 52 and Table 4 on page 52 of the '215 application), was not antigenic (see top of page 53), and dramatically improved the ability of the mouse HDL to inhibit the oxidation of LDL and prevent LDL-induced monocyte chemotactic activity in human artery wall cell cocultures (see page 54 and FIG. 7). Additionally as shown at the bottom of page 54 and in FIG. 8 of the '215 application, the injection of the 5F peptide dramatically reduced atherosclerotic lesions in the mice.

In Example 3 of the '215 application at the bottom of page 73 and in FIG. 18 we demonstrated that incubation of 4F, 5F and 6F, all synthesized from L-amino acids dramatically reduced LDL-induced monocyte chemotactic activity in a human artery wall coculture.

In Example 5 of the '215 application, as indicated at the bottom of page 78 and in FIG. 22A, the peptide, 4F, when given by mouth to mice was more degraded when it was synthesized from L-amino acids than was the case when the peptide was synthesized from D-amino acids. However as shown in FIG. 22A some intact peptide was found in the circulation after oral administration of L-4F. Furthermore, as shown in FIG. 22B the mouse HDL was improved after oral administration of L-4F in terms of its ability to inhibit monocyte chemotactic activity when human artery wall cells were exposed to human LDL, although the improvement in HDL's anti-inflammatory properties were not as dramatic as when the peptide was synthesized from all D-amino acids.

In summary, the examples detailed in the priority documents of this application and incorporated herein by reference demonstrate that administration of the peptides of this invention were effective whether synthesized from L or D-amino acids, although the D-form peptides were more effective when given orally.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of mitigating one or more symptoms of atherosclerosis in a mammal, said method comprising administering to said mammal an effective amount of a peptide comprising the amino acid sequence D-W-L-K-A-F-Y-D-K-F-F-E-K-F-K-E-F-F (SEQ ID NO:7).

2. The method of claim 1, wherein said administering comprises administering said peptide by a route selected from the group consisting of oral administration, nasal administration, rectal administration, intraperitoneal injection, intravascular injection, subcutaneous injection, transcutaneous administration, and intramuscular injection.

3. A method of enhancing the activity of a statin in a mammal, said method comprising coadministering with said statin an effective amount of a peptide comprising the amino acid sequence D-W-L-K-A-F-Y-D-K-F-F-E-K-F-K-E-F-F (SEQ ID NO:7).

4. The method of claim 3, wherein said statin is selected from the group consisting of cerivastatin, atorvastatin, simvastatin, pravastatin, fluvastatin, lovastatin rosuvastatin, and pitavastatin.

5. A method of mitigating one or more symptoms associated with atherosclerosis in a mammal, said method comprising:
   administering to said mammal an effective amount of a statin; and
   an effective amount of a peptide comprising the amino acid sequence D-W-L-K-A-F-Y-D-K-F-F-E-K-F-K-E-F-F (SEQ ID NO:7); wherein the effective amount of the statin is lower than the effective amount of a statin administered without said peptide.

6. The method of claim 5, wherein the effective amount of the peptide is lower than the effective amount of the peptide administered without said statin.

7. The method of claim 5, wherein said statin is selected from the group consisting of cerivastatin, atorvastatin, simvastatin, pravastatin, fluvastatin, lovastatin, rosuvastatin, and pitavastatin.

8. The method according to any one of claims 1, 3, and 5, wherein said peptide is about 40 or fewer amino acids in length.

9. The method of claim 8, wherein the amino acid sequence of said peptide consists of the sequence D-W-L-K-A-F-Y-D-K-F-F-E-K-F-K-E-F-F (SEQ ID NO:7).

10. The method of claim 9, wherein said peptide consists of all "L" amino acids.

11. The method of claim 9, wherein said peptide comprises a protecting group.

12. The method of claim 9, wherein said peptide comprises a first protecting group coupled to the amino terminus and a second protecting group coupled to the carboxyl terminus.

13. The method of claim 12, wherein said first protecting group and said second protecting group are independently selected from the group consisting of acetyl (Ac), amide, a 3 to 20 carbon alkyl group, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-Butyl (tBu), and trifluoroacetyl (TFA).

14. The method of claim 12, wherein said first protecting group is selected from the group consisting of a benzoyl group, an acetyl, a propionyl, a carbobenzoxy, a propyl, a butyl, a pentyl, a hexyl, an N-methyl anthranilyl, and a 3 to 20 carbon alkyl; and
said second protecting group is an amide.

* * * * *

UNITED STATES PATENT AND TRADEMARK OFFICE
CERTIFICATE OF CORRECTION

| | |
|---|---|
| PATENT NO. | : 8,404,635 B2 |
| APPLICATION NO. | : 13/180309 |
| DATED | : March 26, 2013 |
| INVENTOR(S) | : Fogelman et al. |

It is certified that error appears in the above-identified patent and that said Letters Patent is hereby corrected as shown below:

IN THE SPECIFICATION:

1. Column 1, lines 26-30, change "This invention was made with government support under Grant Nos. HL30568 and HL34343 awarded by the United States Public Health Service and National Heart, Lung, and Blood Institute. The Government of the United States of America has certain rights in this invention." to -- This invention was made with Government support under Grant Nos. HL030568 and HL034343, awarded by the National Institutes of Health. The Government has certain rights in this invention. --.

Signed and Sealed this
Thirty-first Day of December, 2013

Margaret A. Focarino
*Commissioner for Patents of the United States Patent and Trademark Office*